US011104886B2

(12) United States Patent
Van Leeuwen et al.

(10) Patent No.: US 11,104,886 B2
(45) Date of Patent: Aug. 31, 2021

(54) KAURENOIC ACID HYDROXYLASES

(71) Applicant: DSM IP Assets B.V., Heerlen (NL)

(72) Inventors: Johannes Gustaaf Ernst Van Leeuwen, Echt (NL); Priscilla Zwartjens, Echt (NL); Viktor Marius Boer, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 16/467,087

(22) PCT Filed: Dec. 4, 2017

(86) PCT No.: PCT/EP2017/081390
§ 371 (c)(1),
(2) Date: Jun. 6, 2019

(87) PCT Pub. No.: WO2018/104238
PCT Pub. Date: Jun. 14, 2018

(65) Prior Publication Data
US 2020/0032225 A1 Jan. 30, 2020

(30) Foreign Application Priority Data

Dec. 8, 2016 (EP) .................................... 16202945

(51) Int. Cl.
*C12N 9/02* (2006.01)
*A23L 27/30* (2016.01)
*C12P 19/12* (2006.01)

(52) U.S. Cl.
CPC ............ *C12N 9/0073* (2013.01); *A23L 27/36* (2016.08); *C12P 19/12* (2013.01); *C12Y 114/13079* (2013.01); *A23V 2002/00* (2013.01)

(58) Field of Classification Search
CPC ....... C12N 9/0073; A23L 27/36; A23L 27/30; C12P 19/12; C12Y 114/13079; A23V 2002/00
See application file for complete search history.

(56) References Cited

U.S. PATENT DOCUMENTS

| | | | |
|---|---|---|---|
| 6,995,003 | B1 | 2/2006 | Nieboer et al. |
| 2004/0053412 | A1 | 3/2004 | Hartley et al. |
| 2006/0127972 | A1 | 6/2006 | Nieboer et al. |
| 2014/0303036 | A1 | 10/2014 | Roubos et al. |
| 2015/0031868 | A1 | 1/2015 | Lehmann et al. |
| 2016/0153017 | A1 | 6/2016 | Van et al. |

FOREIGN PATENT DOCUMENTS

| | | |
|---|---|---|
| EP | 0635574 A1 | 1/1995 |
| EP | 1499708 B1 | 1/2006 |
| EP | 1 897 951 A2 | 3/2008 |
| EP | 2 902 410 A1 | 8/2015 |
| WO | 98/46772 A2 | 10/1998 |
| WO | 99/60102 A2 | 11/1999 |
| WO | 00/37671 A2 | 6/2000 |
| WO | 03/062430 A1 | 7/2003 |
| WO | 2004/099381 A2 | 11/2004 |
| WO | 2006009434 A1 | 1/2006 |
| WO | 2006096130 A1 | 9/2006 |
| WO | 2012/075030 A1 | 6/2012 |
| WO | 2013/076280 A1 | 5/2013 |
| WO | 2013/110673 A1 | 8/2013 |
| WO | WO 2014048392 A1 * | 4/2014 |
| WO | 2015/007748 A1 | 1/2015 |

OTHER PUBLICATIONS

PCT International Search Report for PCT/EP2017/081390, dated Apr. 30, 2018.
Database UniProt [Online], (Oct. 29, 2014), "SubName: Full= Uncharacterized protein {EC0:0000313:EMBL:KFK27759.1};", XP002771155, retrieved from EBI accession No. UniProt:AOA087GD07 Database accession No. AOA087GD07 sequence.
Database UniProt [Online], (Apr. 29, 2015), "SubName: Full= Uncharacterized protein {EC0:0000313:Ensembl1Plants:Bo2g159140.1};" XP002771156, retrieved from EBI accession No. UniProt:AOAOD3AXTO Database accession No. AOAOD3AXTO sequence.
Humphrey, Tania V. et al., "Spatial organisation of four enzymes from Stevia rebaudiana that are involved in steviol glycoside synthesis", Plant Molecular Biology, 2006, pp. 47-62, vol. 61.
Mohamed, Amal A.A. et al., "UDP-dependent glycosyltransferases involved in the biosynthesis of steviol glycosides", Journal of Plant Physiology, 2011, pp. 1136-1141, vol. 168.
Verduyn, Cornelis et al., "Effect of Benzoic Acid on Metabolic Fluxes in Yeasts: A Continuous-Culture Study on the Regulation of Respiration and Alcoholic Fermentation", Yeast, 1992, pp. 501-517, vol. 8.
Fierro, Francisco et al., "Autonomously replicating plasmids carrying the AMA1 region in Penicillium chrysogenum", Current Genetics, 1996, pp. 482-489, vol. 29.
Fleer, R. et al., "Stable Multicopy Vectors for High-Level Secretion of Recombinant Human Serum Albumin by Kluyveromyces Yeasts", Bio/Technology, Oct. 1991, pp. 968-975, vol. 9.

(Continued)

*Primary Examiner* — Iqbal H Chowdhury
(74) *Attorney, Agent, or Firm* — McBee Moore & Vanik IP, LLC

(57) ABSTRACT

The present invention relates a polypeptide having kaurenoic acid 13-hydroxylase activity, which polypeptide comprises an amino acid sequence which, when aligned with a kaurenoic acid 13-hydroxylase comprising the sequence set out in SEQ ID NO: 1 or SEQ ID NO: 3, comprises at least one substitution of an amino acid corresponding to any of amino acids at positions 136, 248, 336 or 403, said positions being defined with reference to SEQ ID NO: 1 or SEQ ID NO: 3 and wherein the polypeptide has one or more modified properties as compared with a reference polypeptide having kaurenoic acid 13-hydroxylase activity. A polypeptide of the invention may be used in a recombinant host for the production of steviol or a steviol glycoside.

8 Claims, 2 Drawing Sheets
Specification includes a Sequence Listing.

(56) References Cited

OTHER PUBLICATIONS

Shirley, Renee L. et al., "Nuclear Import of Upf3p is Mediated by Importing-[alpha]/-[beta] and Export to the Cytoplasm is Required for a Functional Nonsense-Mediated mRNA Decay Pathway in Yeast", Genetics, Aug. 2002, pp. 1465-1482, vol. 161.

* cited by examiner

SEQUENCE LISTING

<160> NUMBER OF SEQ ID NOS: 25

<210> SEQ ID NO 1
<211> LENGTH: 525
<212> TYPE: PRT
<213> ORGANISM: Arabidopsis thaliana

<400> SEQUENCE: 1

```
Met Glu Ser Leu Val Val His Thr Val Asn Ala Ile Trp Cys Ile Val
1               5                   10                  15

Ile Val Gly Ile Phe Ser Val Gly Tyr His Val Tyr Gly Arg Ala Val
            20                  25                  30

Val Glu Gln Trp Arg Met Arg Arg Ser Leu Lys Leu Gln Gly Val Lys
        35                  40                  45

Gly Pro Pro Pro Ser Ile Phe Asn Gly Asn Val Ser Glu Met Gln Arg
    50                  55                  60

Ile Gln Ser Glu Ala Lys His Cys Ser Gly Asp Asn Ile Ile Ser His
65                  70                  75                  80

Asp Tyr Ser Ser Ser Leu Phe Pro His Phe Asp His Trp Arg Lys Gln
                85                  90                  95

Tyr Gly Arg Ile Tyr Thr Tyr Ser Thr Gly Leu Lys Gln His Leu Tyr
            100                 105                 110

Ile Asn His Pro Glu Met Val Lys Glu Leu Ser Gln Thr Asn Thr Leu
        115                 120                 125

Asn Leu Gly Arg Ile Thr His Ile Thr Lys Arg Leu Asn Pro Ile Leu
    130                 135                 140

Gly Asn Gly Ile Ile Thr Ser Asn Gly Pro His Trp Ala His Gln Arg
145                 150                 155                 160

Arg Ile Ile Ala Tyr Glu Phe Thr His Asp Lys Ile Lys Gly Met Val
                165                 170                 175

Gly Leu Met Val Glu Ser Ala Met Pro Met Leu Asn Lys Trp Glu Glu
            180                 185                 190

Met Val Lys Arg Gly Gly Glu Met Gly Cys Asp Ile Arg Val Asp Glu
        195                 200                 205

Asp Leu Lys Asp Val Ser Ala Asp Val Ile Ala Lys Ala Cys Phe Gly
    210                 215                 220

Ser Ser Phe Ser Lys Gly Lys Ala Ile Phe Ser Met Ile Arg Asp Leu
225                 230                 235                 240

Leu Thr Ala Ile Thr Lys Arg Ser Val Leu Phe Arg Phe Asn Gly Phe
                245                 250                 255

Thr Asp Met Val Phe Gly Ser Lys Lys His Gly Asp Val Asp Ile Asp
            260                 265                 270

Ala Leu Glu Met Glu Leu Glu Ser Ser Ile Trp Glu Thr Val Lys Glu
        275                 280                 285

Arg Glu Ile Glu Cys Lys Asp Thr His Lys Lys Asp Leu Met Gln Leu
    290                 295                 300

Ile Leu Glu Gly Ala Met Arg Ser Cys Asp Gly Asn Leu Trp Asp Lys
305                 310                 315                 320

Ser Ala Tyr Arg Arg Phe Val Val Asp Asn Cys Lys Ser Ile Tyr Phe
                325                 330                 335

Ala Gly His Asp Ser Thr Ala Val Ser Val Ser Trp Cys Leu Met Leu
            340                 345                 350

Leu Ala Leu Asn Pro Ser Trp Gln Val Lys Ile Arg Asp Glu Ile Leu
        355                 360                 365
```

Ser Ser Cys Lys Asn Gly Ile Pro Asp Ala Glu Ser Ile Pro Asn Leu
    370                 375                 380

Lys Thr Val Thr Met Val Ile Gln Glu Thr Met Arg Leu Tyr Pro Pro
385                 390                 395                 400

Ala Pro Ile Val Gly Arg Glu Ala Ser Lys Asp Ile Arg Leu Gly Asp
                405                 410                 415

Leu Val Val Pro Lys Gly Val Cys Ile Trp Thr Leu Ile Pro Ala Leu
                420                 425                 430

His Arg Asp Pro Glu Ile Trp Gly Pro Asp Ala Asn Asp Phe Lys Pro
            435                 440                 445

Glu Arg Phe Ser Glu Gly Ile Ser Lys Ala Cys Lys Tyr Pro Gln Ser
    450                 455                 460

Tyr Ile Pro Phe Gly Leu Gly Pro Arg Thr Cys Val Gly Lys Asn Phe
465                 470                 475                 480

Gly Met Met Glu Val Lys Val Leu Val Ser Leu Ile Val Ser Lys Phe
                485                 490                 495

Ser Phe Thr Leu Ser Pro Thr Tyr Gln His Ser Pro Ser His Lys Leu
            500                 505                 510

Leu Val Glu Pro Gln His Gly Val Val Ile Arg Val Val
    515                 520                 525

<210> SEQ ID NO 2
<211> LENGTH: 1578
<212> TYPE: DNA
<213> ORGANISM: Artificial sequence
<220> FEATURE:
<223> OTHER INFORMATION: kaurenoic acid 13-hydroxylase from Arabidopsis
      thaliana, codon-pair optimized for expression in Yarrowia
      lipolitica.

<400> SEQUENCE: 2

```
atggagtctc tggttgtcca caccgtcaac gccatctggt gcattgtcat tgtcggtatc      60
ttctccgtcg gctaccacgt ctacggccga gctgttgtcg agcagtggcg aatgcgacga     120
tctctcaagc tccagggtgt caagggtcct cctccctcca tcttcaacgg taacgtttcc     180
gagatgcagc gaatccagtc cgaggccaag cactgctccg tgacaacat catctcccac      240 gactactctt cttctctgtt ccccccacttt gaccactggc gaaagcagta cggccgaatc     300
tacacctact ccactggcct caagcagcac ctctacatca accaccccga gatggtcaag     360
gagctctccc agaccaacac cctcaacctc ggccgaatca cccacatcac caagcgactc     420
aaccccattc tcggtaacgg tatcatcacc tccaacggcc cccactgggc ccaccagcga     480
cgaatcattg cctacgagtt cacccacgac aagatcaagg gtatggtcgg tctgatggtc     540
gagtccgcca tgcccatgct caacaagtgg gaggagatgg tcaagcgagg tggtgagatg     600
ggctgtgaca tccgagtcga cgaggacctc aaggatgtct ccgctgacgt cattgccaag     660
gcctgtttcg gctcttcctt ctccaagggc aaggccatct ctccatgat ccgagatctg     720 ctcaccgcca tcaccaagcg atccgtcctc ttccgattca cggtttcac cgacatggtt     780 ttcggctcca agaagcacgg tgacgttgac attgacgctc tcgagatgga gctcgagtcc     840
tccatctggg agactgtcaa ggagcgagag attgagtgca aggacaccca caagaaggac     900
ctcatgcagc tcattctcga gggtgccatg cgatcttgtg acggtaacct gtgggacaag     960
tctgcttacc gacgattcgt tgtcgacaac tgcaagtcca tctactttgc cggccacgac    1020
tccaccgcca tttccgtttc ttggtgcctc atgctgctcg ctctcaaccc ctcttggcag    1080
gtcaagatcc gagatgagat tctgtcctcc tgcaagaacg gtatccccga cgccgagtcc    1140
```

```
atccccaacc tcaagaccgt caccatggtc atccaggaga ctatgcgact ctaccctccc    1200
gctcccattg tcggccgaga ggcctccaag gacattcgac tcggtgatct ggttgtcccc    1260
aagggtgtct gtatctggac cctcatcccc gctctgcacc gagatcccga gatctggggt    1320
cccgacgcca acgacttcaa gcccgagcga ttctccgagg gtatctccaa ggcctgcaag    1380 taccccagt cctacatccc ctttggcctc ggccccgaa cctgtgtcgg caagaacttt       1440
ggtatgatgg aggtcaaggt cctcgtttct ctgattgtct ccaagttctc cttcactctg    1500
tctcccacct accagcactc tccctcccac aagctgctcg tcgagcccca gcacggtgtt    1560
gtcatccgag ttgtataa                                                  1578
```

<210> SEQ ID NO 3
<211> LENGTH: 525
<212> TYPE: PRT
<213> ORGANISM: Artificial sequence
<220> FEATURE:
<223> OTHER INFORMATION: kaurenoic acid 13-hydroxylase polypeptide

<400> SEQUENCE: 3

```
Met Glu Ser Leu Val Val His Thr Val Asn Ala Ile Trp Cys Ile Val
1               5                   10                  15

Ile Val Gly Ile Phe Ser Val Gly Tyr His Val Tyr Gly Arg Ala Val
                20                  25                  30

Val Glu Gln Trp Arg Met Arg Ser Leu Lys Leu Gln Gly Val Lys
        35                  40                  45

Gly Pro Pro Ser Ile Phe Asn Gly Asn Val Ser Glu Met Gln Arg
    50                  55                  60

Ile Gln Ser Glu Ala Lys His Asn Ser Gly Asp Asn Ile Ile Ser His
65                  70                  75                  80

Asp Tyr Ser Ser Thr Leu Phe Pro His Phe Asp His Trp Arg Lys Gln
                85                  90                  95

Tyr Gly Arg Ile Tyr Thr Tyr Ser Thr Gly Leu Arg Gln His Leu Tyr
            100                 105                 110

Ile Asn His Pro Glu Met Val Lys Glu Leu Ser Gln Thr Asn Ser Leu
        115                 120                 125

Asp Leu Gly Arg Ile Thr His Ile Thr Lys Arg Leu Ala Pro Ile Leu
    130                 135                 140

Gly Asn Gly Ile Ile Thr Ser Asn Gly Pro His Trp Ala His Gln Arg
145                 150                 155                 160

Arg Ile Ile Ala Tyr Glu Phe Thr His Asp Lys Val Lys Gly Met Val
                165                 170                 175

Gly Leu Met Val Glu Ser Ala Met Pro Met Leu Asn Lys Trp Glu Glu
            180                 185                 190

Met Val Glu Ala Glu Gly Gly Met Gly Cys Asp Ile Arg Val Asp Glu
        195                 200                 205

Asp Leu Lys Asp Val Ser Ala Asp Val Ile Ala Lys Ala Cys Phe Gly
    210                 215                 220

Ser Asn Phe Ser Lys Gly Lys Ala Ile Phe Ser Lys Ile Arg Asp Leu
225                 230                 235                 240

Leu Thr Ala Ile Thr Lys Arg Ser Val Leu Phe Arg Phe Asn Gly Phe
                245                 250                 255

Thr Asp Met Val Phe Gly Ser Lys Lys His Gly Asp Val Asp Ile Asp
            260                 265                 270

Ala Leu Glu Met Glu Leu Glu Ser Ser Ile Trp Glu Thr Val Lys Glu
```

```
                 275                 280                 285
Arg Glu Arg Glu Cys Lys Asp Thr His Lys Asp Leu Leu Gln Leu
    290                 295                 300

Ile Leu Glu Gly Ala Met Arg Ser Cys Asp Gly Asn Leu Trp Asp Lys
305                 310                 315                 320

Ser Ala Tyr Arg Arg Phe Val Val Asp Asn Cys Lys Ser Ile Tyr Phe
                325                 330                 335

Ala Gly His Asp Ser Thr Ala Val Ser Val Ser Trp Cys Leu Met Leu
                340                 345                 350

Leu Ala Leu Asn Pro Ser Trp Gln Glu Lys Ile Arg Asp Glu Ile Leu
                355                 360                 365

Ser Ser Cys Lys Asn Gly Ile Pro Asp Ala Glu Ser Ile Pro Asn Leu
    370                 375                 380

Lys Thr Val Thr Met Val Ile Gln Glu Thr Met Arg Leu Tyr Pro Pro
385                 390                 395                 400

Ala Pro Ile Val Gly Arg Glu Ala Ser Lys Asp Ile Arg Leu Gly Asp
                405                 410                 415

Leu Val Val Pro Lys Gly Val Cys Ile Trp Thr Leu Ile Pro Ala Leu
                420                 425                 430

His Arg Asp Pro Glu Ile Trp Gly Pro Asp Ala Asn Asp Phe Lys Pro
                435                 440                 445

Glu Arg Phe Ser Glu Gly Ile Ser Lys Ala Cys Lys Tyr Pro Gln Ala
    450                 455                 460

Tyr Ile Pro Phe Gly Leu Gly Pro Arg Thr Cys Val Gly Lys Asn Phe
465                 470                 475                 480

Gly Met Met Glu Val Lys Val Leu Val Ser Leu Ile Val Ser Lys Phe
                485                 490                 495

Ser Phe Thr Leu Ser Pro Thr Tyr Gln His Ser Pro Ser His Lys Leu
                500                 505                 510

Leu Val Glu Pro Gln His Gly Val Val Ile Arg Val Val
                515                 520                 525

<210> SEQ ID NO 4
<211> LENGTH: 1578
<212> TYPE: DNA
<213> ORGANISM: Artificial sequence
<220> FEATURE:
<223> OTHER INFORMATION: kaurenoic acid 13-hydroxylase encoding sequence
      optimized for expression in Yarrowia lipolitica

<400> SEQUENCE: 4
atggagtctc tggttgtcca caccgtcaac gccatctggt gcattgtcat tgtcggtatc       60
ttctccgtcg gctaccacgt ctacggccga gccgttgtcg agcagtggcg aatgcgacga      120
tctctcaagc tccagggtgt caagggtcct cctccctcca tcttcaacgg taacgtttcc      180
gagatgcagc gaatccagtc cgaggccaag cacaactccg tgacaacat catctcccac       240 gactactcct ccactctctt cccccacttt gaccactggc gaaagcagta cggccgaatc      300
tacacctact ccaccggtct gcgacagcac ctctacatca ccaccccga tggtcaag        360 gaactgtccc agaccaactc tctcgatctc ggtcgaatca cccacatcac caagcgactc     420
gcccccattc tcggcaacgg tatcatcacc tccaacggcc ccactgggc ccaccagcga      480 cgaatcattg cttacgagtt cacccacgac aaggtcaagg gtatggtcgg cctcatggtc     540
gagtccgcca tgcccatgct caacaagtgg gaggagatgg tcgaggctga ggtggtatg     600 ggctgtgaca tccgagtcga cgaggacctc aaggacgttt ctgccgatgt cattgccaag     660
```

```
gcctgctttg gctccaactt ctccaagggc aaggccattt tctccaagat ccgagatctg      720
ctcaccgcca ttaccaagcg atccgtcctc ttccgattca acggtttcac cgacatggtt      780
ttcggctcca agaagcacgg tgacgttgac attgatgctc tcgagatgga gctggagtcc      840
tccatctggg agactgtcaa ggagcgagag cgagagtgca aggacaccca caagaaggac      900
ctcctccagc tcattctcga gggtgccatg cgatcttgtg acggtaacct gtgggacaag      960
tccgcctacc gacgatttgt tgttgacaac tgcaagtcca tctactttgc cggccacgac     1020
tccaccgccg tttctgtctc ttggtgcctc atgctgctgg ctctcaaccc ctcttggcag     1080
gagaagatcc gtgacgagat tctctcttct tgtaagaacg gtatccccga tgctgagtcc     1140
atccccaacc tcaagaccgt caccatggtc atccaggaga ctatgcgact ctaccctccc     1200
gctcccattg tcggccgaga ggcctccaag gacatccgac tcggtgatct cgttgtcccc     1260
aagggtgtct gcatctggac cctcatcccc gctctgcacc gggaccccga atctggggc     1320 cccgacgcca cgacttcaa gcccgagcga ttctccgagg gtatctccaa ggcttgcaag     1380 taccccagg cctacatccc cttcggtctg gcccccgaa cctgtgtcgg caagaacttc     1440
ggtatgatgg aggtcaaggt ccttgtctct ctcattgtct ccaagttctc cttcactctg     1500
tctcccacct accagcactc tccctcccac aagctcctcg ttgagcccca gcacggtgtt     1560
gtcatccgag tggtgtaa                                                    1578

<210> SEQ ID NO 5
<211> LENGTH: 525
<212> TYPE: PRT
<213> ORGANISM: Artificial Sequence
<220> FEATURE:
<223> OTHER INFORMATION: kaurenoic acid 13-hydroxylase polypeptide

<400> SEQUENCE: 5

Met Glu Ser Leu Val Val His Thr Val Asn Ala Ile Trp Cys Ile Val
1               5                   10                  15

Ile Val Gly Ile Phe Ser Val Gly Tyr His Val Tyr Gly Arg Ala Val
            20                  25                  30

Val Glu Gln Trp Arg Met Arg Arg Ser Leu Lys Leu Gln Gly Val Lys
        35                  40                  45

Gly Pro Pro Pro Ser Ile Phe Asn Gly Asn Val Ser Glu Met Gln Arg
    50                  55                  60

Ile Gln Ser Glu Ala Lys His Asn Ser Gly Asp Asn Ile Ile Ser His
65                  70                  75                  80

Asp Tyr Ser Ser Thr Leu Phe Pro His Phe Asp His Trp Arg Lys Gln
                85                  90                  95

Tyr Gly Arg Ile Tyr Thr Tyr Ser Thr Gly Leu Arg Gln His Leu Tyr
            100                 105                 110

Ile Asn His Pro Glu Met Val Lys Glu Leu Ser Gln Thr Asn Ser Leu
        115                 120                 125

Asp Leu Gly Arg Ile Thr His Met Thr Lys Arg Leu Ala Pro Ile Leu
    130                 135                 140

Gly Asn Gly Ile Ile Thr Ser Asn Gly Pro His Trp Ala His Gln Arg
145                 150                 155                 160

Arg Ile Ile Ala Tyr Glu Phe Thr His Asp Lys Val Lys Gly Met Val
                165                 170                 175

Gly Leu Met Val Glu Ser Ala Met Pro Met Leu Asn Lys Trp Glu Glu
            180                 185                 190
```

Met Val Glu Ala Glu Gly Gly Met Gly Cys Asp Ile Arg Val Asp Glu
        195                 200                 205

Asp Leu Lys Asp Val Ser Ala Asp Val Ile Ala Lys Ala Cys Phe Gly
    210                 215                 220

Ser Asn Phe Ser Lys Gly Lys Ala Ile Phe Ser Lys Ile Arg Asp Leu
225                 230                 235                 240

Leu Thr Ala Ile Thr Lys Arg Ser Val Leu Phe Arg Phe Asn Gly Phe
                245                 250                 255

Thr Asp Met Val Phe Gly Ser Lys Lys His Gly Asp Val Asp Ile Asp
            260                 265                 270

Ala Leu Glu Met Glu Leu Glu Ser Ser Ile Trp Glu Thr Val Lys Glu
        275                 280                 285

Arg Glu Arg Glu Cys Lys Asp Thr His Lys Lys Asp Leu Leu Gln Leu
    290                 295                 300

Ile Leu Glu Gly Ala Met Arg Ser Cys Asp Gly Asn Leu Trp Asp Lys
305                 310                 315                 320

Ser Ala Tyr Arg Arg Phe Val Val Asp Asn Cys Lys Ser Ile Tyr Phe
                325                 330                 335

Ala Gly His Asp Ser Thr Ala Val Ser Val Ser Trp Cys Leu Met Leu
            340                 345                 350

Leu Ala Leu Asn Pro Ser Trp Gln Glu Lys Ile Arg Asp Glu Ile Leu
        355                 360                 365

Ser Ser Cys Lys Asn Gly Ile Pro Asp Ala Glu Ser Ile Pro Asn Leu
    370                 375                 380

Lys Thr Val Thr Met Val Ile Gln Glu Thr Met Arg Leu Tyr Pro Pro
385                 390                 395                 400

Ala Pro Ile Val Gly Arg Glu Ala Ser Lys Asp Ile Arg Leu Gly Asp
                405                 410                 415

Leu Val Val Pro Lys Gly Val Cys Ile Trp Thr Leu Ile Pro Ala Leu
            420                 425                 430

His Arg Asp Pro Glu Ile Trp Gly Pro Asp Ala Asn Asp Phe Lys Pro
        435                 440                 445

Glu Arg Phe Ser Glu Gly Ile Ser Lys Ala Cys Lys Tyr Pro Gln Ala
    450                 455                 460

Tyr Ile Pro Phe Gly Leu Gly Pro Arg Thr Cys Val Gly Lys Asn Phe
465                 470                 475                 480

Gly Met Met Glu Val Lys Val Leu Val Ser Leu Ile Val Ser Lys Phe
                485                 490                 495

Ser Phe Thr Leu Ser Pro Thr Tyr Gln His Ser Pro Ser His Lys Leu
            500                 505                 510

Leu Val Glu Pro Gln His Gly Val Val Ile Arg Val Val
        515                 520                 525

<210> SEQ ID NO 6
<211> LENGTH: 1578
<212> TYPE: DNA
<213> ORGANISM: Artificial Sequence
<220> FEATURE:
<223> OTHER INFORMATION: kaurenoic acid 13-hydroxylase encoding sequence
      optimized for expression in Yarrowia lipolitica

<400> SEQUENCE: 6
atggagtctc tggttgtcca caccgtcaac gccatctggt gcattgtcat tgtcggtatc      60
ttctccgtcg gctaccacgt ctacggccga gccgttgtcg agcagtggcg aatgcgacga     120
tctctcaagc tccagggtgt caagggtcct cctccctcca tcttcaacgg taacgtttcc     180

-continued

```
gagatgcagc gaatccagtc cgaggccaag cacaactccg gtgacaacat catctcccac      240
gactactcct ccactctctt cccccacttt gaccactggc gaaagcagta cggccgaatc      300
tacacctact ccaccggtct gcgacagcac ctctacatca accaccccga gatggtcaag      360
gaactgtccc agaccaactc tctcgatctc ggtcgaatca cccacatgac caagcgactc      420
gcccccattc tcggcaacgg tatcatcacc tccaacggcc ccactgggc ccaccagcga      480 cgaatcattg cttacgagtt cacccacgac aaggtcaagg gtatggtcgg cctcatggtc      540
gagtccgcca tgcccatgct caacaagtgg gaggagatgg tcgaggctga gggtggtatg      600
ggctgtgaca tccgagtcga cgaggacctc aaggacgttt ctgccgatgt cattgccaag      660
gcctgctttg gctccaactt ctccaagggc aaggccattt tctccaagat ccgagatctg      720
ctcaccgcca ttaccaagcg atccgtcctc ttccgattca acggtttcac cgacatggtt      780
ttcggctcca agaagcacgg tgacgttgac attgatgctc tcgagatgga gctggagtcc      840
tccatctggg agactgtcaa ggagcgagag cgagagtgca aggacaccca caagaaggac      900
ctcctccagc tcattctcga gggtgccatg cgatcttgtg acggtaacct gtgggacaag      960
tccgcctacc gacgatttgt tgttgacaac tgcaagtcca tctactttgc cggccacgac     1020
tccaccgccg tttctgtctc ttggtgcctc atgctgctgg ctctcaaccc ctcttggcag     1080
gagaagatcc gtgacgagat tctctcttct tgtaagaacg gtatcccga tgctgagtcc     1140 atccccaacc tcaagaccgt caccatggtc atccaggaga ctatgcgact ctaccctccc     1200
gctcccattg tcggccgaga ggcctccaag gacatccgac tcggtgatct cgttgtcccc     1260
aagggtgtct gcatctggac cctcatcccc gctctgcacc gggaccccga atctggggc     1320 cccgacgcca cgacttcaa gcccgagcga ttctccgagg gtatctccaa ggcttgcaag     1380 taccccagg cctacatccc cttcggtctg ggccccgaa cctgtgtcgg caagaacttc     1440
ggtatgatgg aggtcaaggt ccttgtctct ctcattgtct ccaagttctc cttcactctg     1500
tctcccacct accagcactc tccctcccac aagctcctcg ttgagcccca gcacggtgtt     1560
gtcatccgag tggtgtaa                                                   1578
```

<210> SEQ ID NO 7
<211> LENGTH: 525
<212> TYPE: PRT
<213> ORGANISM: Artificial Sequence
<220> FEATURE:
<223> OTHER INFORMATION: kaurenoic acid 13-hydroxylase polypeptide

<400> SEQUENCE: 7

```
Met Glu Ser Leu Val Val His Thr Val Asn Ala Ile Trp Cys Ile Val
1               5                   10                  15

Ile Val Gly Ile Phe Ser Val Gly Tyr His Val Tyr Gly Arg Ala Val
            20                  25                  30

Val Glu Gln Trp Arg Met Arg Arg Ser Leu Lys Leu Gln Gly Val Lys
        35                  40                  45

Gly Pro Pro Pro Ser Ile Phe Asn Gly Asn Val Ser Glu Met Gln Arg
    50                  55                  60

Ile Gln Ser Glu Ala Lys His Asn Ser Gly Asp Asn Ile Ile Ser His
65                  70                  75                  80

Asp Tyr Ser Ser Thr Leu Phe Pro His Phe Asp His Trp Arg Lys Gln
                85                  90                  95

Tyr Gly Arg Ile Tyr Thr Tyr Ser Thr Gly Leu Arg Gln His Leu Tyr
            100                 105                 110
```

```
Ile Asn His Pro Glu Met Val Lys Glu Leu Ser Gln Thr Asn Ser Leu
    115                 120                 125

Asp Leu Gly Arg Ile Thr His Ile Thr Lys Arg Leu Ala Pro Ile Leu
130                 135                 140

Gly Asn Gly Ile Ile Thr Ser Asn Gly Pro His Trp Ala His Gln Arg
145                 150                 155                 160

Arg Ile Ile Ala Tyr Glu Phe Thr His Asp Lys Val Lys Gly Met Val
                165                 170                 175

Gly Leu Met Val Glu Ser Ala Met Pro Met Leu Asn Lys Trp Glu Glu
                180                 185                 190

Met Val Glu Ala Glu Gly Gly Met Gly Cys Asp Ile Arg Val Asp Glu
                195                 200                 205

Asp Leu Lys Asp Val Ser Ala Asp Val Ile Ala Lys Ala Cys Phe Gly
            210                 215                 220

Ser Asn Phe Ser Lys Gly Lys Ala Ile Phe Ser Lys Ile Arg Asp Leu
225                 230                 235                 240

Leu Thr Ala Ile Thr Lys Arg Ser Val Leu Phe Arg Phe Asn Gly Phe
                245                 250                 255

Thr Asp Met Val Phe Gly Ser Lys Lys His Gly Asp Val Asp Ile Asp
                260                 265                 270

Ala Leu Glu Met Glu Leu Glu Ser Ser Ile Trp Glu Thr Val Lys Glu
            275                 280                 285

Arg Glu Arg Glu Cys Lys Asp Thr His Lys Lys Asp Leu Leu Gln Leu
        290                 295                 300

Ile Leu Glu Gly Ala Met Arg Ser Cys Asp Gly Asn Leu Trp Asp Lys
305                 310                 315                 320

Ser Ala Tyr Arg Arg Phe Val Val Asp Asn Cys Lys Ser Ile Tyr Ser
                325                 330                 335

Ala Gly His Asp Ser Thr Ala Val Ser Val Ser Trp Cys Leu Met Leu
            340                 345                 350

Leu Ala Leu Asn Pro Ser Trp Gln Glu Lys Ile Arg Asp Glu Ile Leu
        355                 360                 365

Ser Ser Cys Lys Asn Gly Ile Pro Asp Ala Glu Ser Ile Pro Asn Leu
        370                 375                 380

Lys Thr Val Thr Met Val Ile Gln Glu Thr Met Arg Leu Tyr Pro Pro
385                 390                 395                 400

Ala Pro Ile Val Gly Arg Glu Ala Ser Lys Asp Ile Arg Leu Gly Asp
                405                 410                 415

Leu Val Val Pro Lys Gly Val Cys Ile Trp Thr Leu Ile Pro Ala Leu
                420                 425                 430

His Arg Asp Pro Glu Ile Trp Gly Pro Asp Ala Asn Asp Phe Lys Pro
            435                 440                 445

Glu Arg Phe Ser Glu Gly Ile Ser Lys Ala Cys Lys Tyr Pro Gln Ala
    450                 455                 460

Tyr Ile Pro Phe Gly Leu Gly Pro Arg Thr Cys Val Gly Lys Asn Phe
465                 470                 475                 480

Gly Met Met Glu Val Lys Val Leu Val Ser Leu Ile Val Ser Lys Phe
                485                 490                 495

Ser Phe Thr Leu Ser Pro Thr Tyr Gln His Ser Pro Ser His Lys Leu
                500                 505                 510

Leu Val Glu Pro Gln His Gly Val Val Ile Arg Val Val
                515                 520                 525
```

<210> SEQ ID NO 8
<211> LENGTH: 1578
<212> TYPE: DNA
<213> ORGANISM: Artificial Sequence
<220> FEATURE:
<223> OTHER INFORMATION: kaurenoic acid 13-hydroxylase encoding sequence optimized for expression in Yarrowia lipolitica

<400> SEQUENCE: 8

```
atggagtctc tggttgtcca caccgtcaac gccatctggt gcattgtcat tgtcggtatc      60
ttctccgtcg gctaccacgt ctacggccga gccgttgtcg agcagtggcg aatgcgacga     120
tctctcaagc tccagggtgt caagggtcct cctcccctcca tcttcaacgg taacgtttcc    180
gagatgcagc gaatccagtc cgaggccaag cacaactccg gtgacaacat catctcccac    240
gactactcct ccactctctt ccccacttt gaccactggc gaaagcagta cggccgaatc     300
tacacctact ccaccggtct gcgacagcac ctctacatca ccaccccga gatggtcaag     360
gaactgtccc agaccaactc tctcgatctc ggtcgaatca cccacatcac caagcgactc    420
gccccattc tcggcaacgg tatcatcacc tccaacggcc ccactgggc ccaccagcga     480
cgaatcattg cttacgagtt cacccacgac aaggtcaagg gtatggtcgg cctcatggtc    540
gagtccgcca tgcccatgct caacaagtgg gaggagatgg tcgaggctga gggtggtatg    600
ggctgtgaca tccgagtcga cgaggaccte aaggacgttt ctgccgatgt cattgccaag    660
gcctgctttg gctccaactt ctccaagggc aaggccattt tctccaagat ccgagatctg    720
ctcaccgcca ttaccaagcg atccgtcctc ttccgattca acggtttcac cgacatggtt    780
ttcggctcca agaagcacgg tgacgttgac attgatgctc tcgagatgga gctggagtcc    840
tccatctggg agactgtcaa ggagcgagag cgagagtgca aggacaccca caagaaggac    900
ctcctccagc tcattctcga gggtgccatg cgatcttgtg acggtaacct gtgggacaag    960
tccgcctacc gacgatttgt tgttgacaac tgcaagtcca tctactccgc cggccacgac   1020
tccaccgccg tttctgtctc ttggtgcctc atgctgctgg ctctcaaccc ctcttggcag   1080
gagaagatcc gtgacgagat tctctcttct tgtaagaacg gtatcccga tgctgagtcc   1140
atccccaacc tcaagaccgt caccatggtc atccaggaga ctatgcgact ctaccctccc   1200
gctcccattg tcggccgaga ggcctccaag gacatccgac tcggtgatct cgttgtcccc   1260
aagggtgtct gcatctggac cctcatcccc gctctgcacc gggaccccga atctgggc    1320
cccgacgcca cgacttcaa gcccgagcga ttctccgagg gtatctccaa ggcttgcaag   1380
taccccagg cctacatccc cttcggtctg ggcccccgaa cctgtgtcgg caagaacttc   1440
ggtatgatgg aggtcaaggt ccttgtctct ctcattgtct ccaagttctc cttcactctg   1500
tctcccacct accagcactc tccctcccac aagctcctcg ttgagcccca gcacggtgtt   1560
gtcatccgag tggtgtaa                                                 1578
```

<210> SEQ ID NO 9
<211> LENGTH: 525
<212> TYPE: PRT
<213> ORGANISM: Artificial Sequence
<220> FEATURE:
<223> OTHER INFORMATION: kaurenoic acid 13-hydroxylase polypeptide

<400> SEQUENCE: 9

```
Met Glu Ser Leu Val Val His Thr Val Asn Ala Ile Trp Cys Ile Val
1               5                   10                  15

Ile Val Gly Ile Phe Ser Val Gly Tyr His Val Tyr Gly Arg Ala Val
```

```
                20                  25                  30
Val Glu Gln Trp Arg Met Arg Arg Ser Leu Lys Leu Gln Gly Val Lys
             35                  40                  45
Gly Pro Pro Ser Ile Phe Asn Gly Asn Val Ser Glu Met Gln Arg
     50                  55                  60
Ile Gln Ser Glu Ala Lys His Asn Ser Gly Asp Asn Ile Ile Ser His
 65                  70                  75                  80
Asp Tyr Ser Ser Thr Leu Phe Pro His Phe Asp His Trp Arg Lys Gln
                 85                  90                  95
Tyr Gly Arg Ile Tyr Thr Tyr Ser Thr Gly Leu Arg Gln His Leu Tyr
                100                 105                 110
Ile Asn His Pro Glu Met Val Lys Glu Leu Ser Gln Thr Asn Ser Leu
            115                 120                 125
Asp Leu Gly Arg Ile Thr His Val Thr Lys Arg Leu Ala Pro Ile Leu
        130                 135                 140
Gly Asn Gly Ile Ile Thr Ser Asn Gly Pro His Trp Ala His Gln Arg
145                 150                 155                 160
Arg Ile Ile Ala Tyr Glu Phe Thr His Asp Lys Val Lys Gly Met Val
                165                 170                 175
Gly Leu Met Val Glu Ser Ala Met Pro Met Leu Asn Lys Trp Glu Glu
            180                 185                 190
Met Val Glu Ala Glu Gly Gly Met Gly Cys Asp Ile Arg Val Asp Glu
        195                 200                 205
Asp Leu Lys Asp Val Ser Ala Asp Val Ile Ala Lys Ala Cys Phe Gly
    210                 215                 220
Ser Asn Phe Ser Lys Gly Lys Ala Ile Phe Ser Lys Ile Arg Asp Leu
225                 230                 235                 240
Leu Thr Ala Ile Thr Lys Arg Ser Val Leu Phe Arg Phe Asn Gly Phe
                245                 250                 255
Thr Asp Met Val Phe Gly Ser Lys Lys His Gly Asp Val Asp Ile Asp
            260                 265                 270
Ala Leu Glu Met Glu Leu Glu Ser Ser Ile Trp Glu Thr Val Lys Glu
        275                 280                 285
Arg Glu Arg Glu Cys Lys Asp Thr His Lys Lys Asp Leu Leu Gln Leu
    290                 295                 300
Ile Leu Glu Gly Ala Met Arg Ser Cys Asp Gly Asn Leu Trp Asp Lys
305                 310                 315                 320
Ser Ala Tyr Arg Arg Phe Val Val Asp Asn Cys Lys Ser Ile Tyr Phe
                325                 330                 335
Ala Gly His Asp Ser Thr Ala Val Ser Val Ser Trp Cys Leu Met Leu
            340                 345                 350
Leu Ala Leu Asn Pro Ser Trp Gln Glu Lys Ile Arg Asp Glu Ile Leu
        355                 360                 365
Ser Ser Cys Lys Asn Gly Ile Pro Asp Ala Glu Ser Ile Pro Asn Leu
    370                 375                 380
Lys Thr Val Thr Met Val Ile Gln Glu Thr Met Arg Leu Tyr Pro Pro
385                 390                 395                 400
Ala Pro Ile Val Gly Arg Glu Ala Ser Lys Asp Ile Arg Leu Gly Asp
                405                 410                 415
Leu Val Val Pro Lys Gly Val Cys Ile Trp Thr Leu Ile Pro Ala Leu
            420                 425                 430
His Arg Asp Pro Glu Ile Trp Gly Pro Asp Ala Asn Asp Phe Lys Pro
        435                 440                 445
```

```
Glu Arg Phe Ser Glu Gly Ile Ser Lys Ala Cys Lys Tyr Pro Gln Ala
    450                 455                 460

Tyr Ile Pro Phe Gly Leu Gly Pro Arg Thr Cys Val Gly Lys Asn Phe
465                 470                 475                 480

Gly Met Met Glu Val Lys Val Leu Val Ser Leu Ile Val Ser Lys Phe
                485                 490                 495

Ser Phe Thr Leu Ser Pro Thr Tyr Gln His Ser Pro Ser His Lys Leu
                500                 505                 510

Leu Val Glu Pro Gln His Gly Val Val Ile Arg Val Val
                515                 520                 525

<210> SEQ ID NO 10
<211> LENGTH: 1578
<212> TYPE: DNA
<213> ORGANISM: Artificial Sequence
<220> FEATURE:
<223> OTHER INFORMATION: kaurenoic acid 13-hydroxylase encoding sequence
      optimized for expression in Yarrowia lipolitica

<400> SEQUENCE: 10
atggagtctc tggttgtcca caccgtcaac gccatctggt gcattgtcat tgtcggtatc      60
ttctccgtcg gctaccacgt ctacggccga ccgttgtcg agcagtggcg aatgcgacga     120
tctctcaagc tccagggtgt caagggtcct cctccctcca tcttcaacgg taacgttttc    180
gagatgcagc gaatccagtc cgaggccaag cacaactccg gtgacaacat catctcccac    240
gactactcct ccactctctt cccccacttt gaccactggc gaaagcagta cggccgaatc    300
tacacctact ccaccggtct cgcacagcac ctctacatca ccaccccga gatggtcaag    360 gaactgtccc agaccaactc tctcgatctc ggtcgaatca cccacgtcac caagcgactc    420
gcccccattc tcggcaacgg tatcatcacc tccaacggcc ccactgggc ccaccagcga     480 cgaatcattg cttacgagtt cacccacgac aaggtcaagg gtatggtcgg cctcatggtc    540
gagtccgcca tgcccatgct caacaagtgg gaggagatgg tcgaggctga gggtggtatg    600
ggctgtgaca tccgagtcga cgaggaccte aaggacgttt ctgccgatgt cattgccaag    660
gcctgctttg gctccaactt ctccaagggc aaggccattt tctccaagat ccgagatctg    720
ctcaccgcca ttaccaagcg atccgtcctc ttccgattca acggtttcac cgacatggtt    780
ttcggctcca agaagcacgg tgacgttgac attgatgctc tcgagatgga gctggagtcc    840
tccatctggg agactgtcaa ggagcgagag cgagagtgca aggacaccca caagaaggac    900
ctcctccagc tcattctcga gggtgccatg cgatcttgtg acggtaacct gtgggacaag    960
tccgcctacc gacgatttgt tgttgacaac tgcaagtcca tctactttgc cggccacgac   1020
tccaccgccg tttctgtctc ttggtgcctc atgctgctgg ctctcaaccc ctcttggcag   1080
gagaagatcc gtgacgagat tctctcttct tgtaagaacg gtatccccga tgctgagtcc   1140
atccccaacc tcaagaccgt caccatggtc atccaggaga ctatgcgact ctaccctccc   1200
gctcccattg tcggccgaga ggcctccaag gacatccgac tcggtgatct cgttgtcccc   1260
aagggtgtct gcatctggac cctcatcccc gctctgcacc gggaccccga aatctggggc   1320
cccgacgcca acgacttcaa gcccgagcga ttctccgagg gtatctccaa ggcttgcaag   1380 taccccagg cctacatccc cttcggtctg ggccccgaa cctgtgtcgg caagaacttc   1440
ggtatgatgg aggtcaaggt ccttgtctct ctcattgtct ccaagttctc cttcactctg   1500
tctcccacct accagcactc tccctcccac aagctcctcg ttgagcccca gcacggtgtt   1560
```
gtcatccgag tggtgtaa                                                   1578

<210> SEQ ID NO 11
<211> LENGTH: 525
<212> TYPE: PRT
<213> ORGANISM: Artificial Sequence
<220> FEATURE:
<223> OTHER INFORMATION: kaurenoic acid 13-hydroxylase polypeptide

<400> SEQUENCE: 11

```
Met Glu Ser Leu Val Val His Thr Val Asn Ala Ile Trp Cys Ile Val
1               5                   10                  15

Ile Val Gly Ile Phe Ser Val Gly Tyr His Val Tyr Gly Arg Ala Val
            20                  25                  30

Val Glu Gln Trp Arg Met Arg Arg Ser Leu Lys Leu Gln Gly Val Lys
        35                  40                  45

Gly Pro Pro Ser Ile Phe Asn Gly Asn Val Ser Glu Met Gln Arg
    50                  55                  60

Ile Gln Ser Glu Ala Lys His Asn Ser Gly Asp Asn Ile Ile Ser His
65                  70                  75                  80

Asp Tyr Ser Ser Thr Leu Phe Pro His Phe Asp His Trp Arg Lys Gln
                85                  90                  95

Tyr Gly Arg Ile Tyr Thr Tyr Ser Thr Gly Leu Arg Gln His Leu Tyr
            100                 105                 110

Ile Asn His Pro Glu Met Val Lys Glu Leu Ser Gln Thr Asn Ser Leu
        115                 120                 125

Asp Leu Gly Arg Ile Thr His Ile Thr Lys Arg Leu Ala Pro Ile Leu
    130                 135                 140

Gly Asn Gly Ile Ile Thr Ser Asn Gly Pro His Trp Ala His Gln Arg
145                 150                 155                 160

Arg Ile Ile Ala Tyr Glu Phe Thr His Asp Lys Val Lys Gly Met Val
                165                 170                 175

Gly Leu Met Val Glu Ser Ala Met Pro Met Leu Asn Lys Trp Glu Glu
            180                 185                 190

Met Val Glu Ala Glu Gly Gly Met Gly Cys Asp Ile Arg Val Asp Glu
        195                 200                 205

Asp Leu Lys Asp Val Ser Ala Asp Val Ile Ala Lys Ala Cys Phe Gly
    210                 215                 220

Ser Asn Phe Ser Lys Gly Lys Ala Ile Phe Ser Lys Ile Arg Asp Leu
225                 230                 235                 240

Leu Thr Ala Ile Thr Lys Arg Asn Val Leu Phe Arg Phe Asn Gly Phe
                245                 250                 255

Thr Asp Met Val Phe Gly Ser Lys Lys His Gly Asp Val Asp Ile Asp
            260                 265                 270

Ala Leu Glu Met Glu Leu Glu Ser Ser Ile Trp Glu Thr Val Lys Glu
        275                 280                 285

Arg Glu Arg Glu Cys Lys Asp Thr His Lys Lys Asp Leu Leu Gln Leu
    290                 295                 300

Ile Leu Glu Gly Ala Met Arg Ser Cys Asp Gly Asn Leu Trp Asp Lys
305                 310                 315                 320

Ser Ala Tyr Arg Arg Phe Val Val Asp Asn Cys Lys Ser Ile Tyr Phe
                325                 330                 335

Ala Gly His Asp Ser Thr Ala Val Ser Val Ser Trp Cys Leu Met Leu
            340                 345                 350

Leu Ala Leu Asn Pro Ser Trp Gln Glu Lys Ile Arg Asp Glu Ile Leu
```

|  |  |  |  | 355 |  |  |  |  | 360 |  |  |  |  | 365 |  |  |  |
|---|---|---|---|---|---|---|---|---|---|---|---|---|---|---|---|---|---|
| Ser | Ser | Cys | Lys | Asn | Gly | Ile | Pro | Asp | Ala | Glu | Ser | Ile | Pro | Asn | Leu |
|  |  |  | 370 |  |  |  |  | 375 |  |  |  |  | 380 |  |  |

| Lys | Thr | Val | Thr | Met | Val | Ile | Gln | Glu | Thr | Met | Arg | Leu | Tyr | Pro | Pro |
|---|---|---|---|---|---|---|---|---|---|---|---|---|---|---|---|
| 385 |  |  |  |  | 390 |  |  |  |  | 395 |  |  |  |  | 400 |

| Ala | Pro | Ile | Val | Gly | Arg | Glu | Ala | Ser | Lys | Asp | Ile | Arg | Leu | Gly | Asp |
|---|---|---|---|---|---|---|---|---|---|---|---|---|---|---|---|
|  |  |  |  | 405 |  |  |  |  | 410 |  |  |  |  | 415 |  |

| Leu | Val | Val | Pro | Lys | Gly | Val | Cys | Ile | Trp | Thr | Leu | Ile | Pro | Ala | Leu |
|---|---|---|---|---|---|---|---|---|---|---|---|---|---|---|---|
|  |  |  | 420 |  |  |  |  | 425 |  |  |  |  | 430 |  |  |

| His | Arg | Asp | Pro | Glu | Ile | Trp | Gly | Pro | Asp | Ala | Asn | Asp | Phe | Lys | Pro |
|---|---|---|---|---|---|---|---|---|---|---|---|---|---|---|---|
|  |  | 435 |  |  |  |  | 440 |  |  |  |  | 445 |  |  |  |

| Glu | Arg | Phe | Ser | Glu | Gly | Ile | Ser | Lys | Ala | Cys | Lys | Tyr | Pro | Gln | Ala |
|---|---|---|---|---|---|---|---|---|---|---|---|---|---|---|---|
|  |  | 450 |  |  |  |  | 455 |  |  |  |  | 460 |  |  |  |

| Tyr | Ile | Pro | Phe | Gly | Leu | Gly | Pro | Arg | Thr | Cys | Val | Gly | Lys | Asn | Phe |
|---|---|---|---|---|---|---|---|---|---|---|---|---|---|---|---|
| 465 |  |  |  |  | 470 |  |  |  |  | 475 |  |  |  |  | 480 |

| Gly | Met | Met | Glu | Val | Lys | Val | Leu | Val | Ser | Leu | Ile | Val | Ser | Lys | Phe |
|---|---|---|---|---|---|---|---|---|---|---|---|---|---|---|---|
|  |  |  |  | 485 |  |  |  |  | 490 |  |  |  |  | 495 |  |

| Ser | Phe | Thr | Leu | Ser | Pro | Thr | Tyr | Gln | His | Ser | Pro | Ser | His | Lys | Leu |
|---|---|---|---|---|---|---|---|---|---|---|---|---|---|---|---|
|  |  |  | 500 |  |  |  |  | 505 |  |  |  |  | 510 |  |  |

| Leu | Val | Glu | Pro | Gln | His | Gly | Val | Val | Ile | Arg | Val | Val |
|---|---|---|---|---|---|---|---|---|---|---|---|---|
|  |  | 515 |  |  |  |  | 520 |  |  |  |  | 525 |

<210> SEQ ID NO 12
<211> LENGTH: 1578
<212> TYPE: DNA
<213> ORGANISM: Artificial Sequence
<220> FEATURE:
<223> OTHER INFORMATION: kaurenoic acid 13-hydroxylase encoding sequence
   optimized for expression in Yarrowia lipolitica

<400> SEQUENCE: 12

```
atggagtctc tggttgtcca caccgtcaac gccatctggt gcattgtcat tgtcggtatc     60
ttctccgtcg gctaccacgt ctacggccga gccgttgtcg agcagtggcg aatgcgacga    120
tctctcaagc tccagggtgt caagggtcct cctccctcca tcttcaacgg taacgttttc    180
gagatgcagc gaatccagtc cgaggccaag cacaactccg tgacaacat catctcccac     240 gactactcct ccactctctt ccccacttt gaccactggc gaaagcagta cggccgaatc     300
tacacctact ccaccggtct cgacagcac ctctacatca accaccccga gatggtcaag     360
gaactgtccc agaccaactc tctcgatctc ggtcgaatca cccacatcac caagcgactc    420
gcccccattc tcgcaacgg tatcatcacc tccaacggcc ccactgggc ccaccagcga     480 cgaatcattg cttacgagtt cacccacgac aaggtcaagg gtatggtcgg cctcatggtc    540
gagtccgcca tgcccatgct caacaagtgg gaggagatgg tcgaggctga ggtggtatg     600 ggctgtgaca tccgagtcga cgaggacctc aaggacgttt ctgccgatgt cattgccaag    660
gcctgctttg gctccaactt ctccaagggc aaggccattt ctccaagat ccagatctg      720 ctcaccgcca ttaccaagcg aaacgtcctc ttccgattca acggttcac cgacatggtt     780 ttcggctcca gaagcacgg tgacgttgac attgatgctc tcgagatgga gctggagtcc    840
tccatctggg agactgtcaa ggagcgagag cgagagtgca aggacaccca aagaaggac     900 ctcctccagc tcattctcga gggtgccatg cgatcttgtg acggtaacct gtgggacaag    960
tccgcctacc gacgatttgt tgttgacaac tgcaagtcca tctactttgc cggccacgac   1020
tccaccgccg tttctgtctc ttggtgcctc atgctgctgg ctctcaaccc ctcttggcag   1080
```

```
gagaagatcc gtgacgagat tctctcttct tgtaagaacg gtatccccga tgctgagtcc   1140
atccccaacc tcaagaccgt caccatggtc atccaggaga ctatgcgact ctaccctccc   1200
gctcccattg tcggccgaga ggcctccaag gacatccgac tcggtgatct cgttgtcccc   1260
aagggtgtct gcatctggac cctcatcccc gctctgcacc gggaccccga atctggggc    1320 cccgacgcca acgacttcaa gcccgagcga ttctccgagg gtatctccaa ggcttgcaag   1380
taccccaggc ctacatccc cttcggtctg ggccccgaa cctgtgtcgg caagaacttc     1440
ggtatgatgg aggtcaaggt ccttgtctct ctcattgtct ccaagttctc cttcactctg   1500
tctcccacct accagcactc tccctcccac aagctcctcg ttgagcccca gcacggtgtt   1560
gtcatccgag tggtgtaa                                                 1578
```

<210> SEQ ID NO 13
<211> LENGTH: 525
<212> TYPE: PRT
<213> ORGANISM: Artificial Sequence
<220> FEATURE:
<223> OTHER INFORMATION: kaurenoic acid 13-hydroxylase polypeptide

<400> SEQUENCE: 13

```
Met Glu Ser Leu Val Val His Thr Val Asn Ala Ile Trp Cys Ile Val
1               5                   10                  15

Ile Val Gly Ile Phe Ser Val Gly Tyr His Val Tyr Gly Arg Ala Val
            20                  25                  30

Val Glu Gln Trp Arg Met Arg Arg Ser Leu Lys Leu Gln Gly Val Lys
        35                  40                  45

Gly Pro Pro Pro Ser Ile Phe Asn Gly Asn Val Ser Glu Met Gln Arg
    50                  55                  60

Ile Gln Ser Glu Ala Lys His Asn Ser Gly Asp Asn Ile Ile Ser His
65                  70                  75                  80

Asp Tyr Ser Ser Thr Leu Phe Pro His Phe Asp His Trp Arg Lys Gln
                85                  90                  95

Tyr Gly Arg Ile Tyr Thr Tyr Ser Thr Gly Leu Arg Gln His Leu Tyr
            100                 105                 110

Ile Asn His Pro Glu Met Val Lys Glu Leu Ser Gln Thr Asn Ser Leu
        115                 120                 125

Asp Leu Gly Arg Ile Thr His Ile Thr Lys Arg Leu Ala Pro Ile Leu
    130                 135                 140

Gly Asn Gly Ile Ile Thr Ser Asn Gly Pro His Trp Ala His Gln Arg
145                 150                 155                 160

Arg Ile Ile Ala Tyr Glu Phe Thr His Asp Lys Val Lys Gly Met Val
                165                 170                 175

Gly Leu Met Val Glu Ser Ala Met Pro Met Leu Asn Lys Trp Glu Glu
            180                 185                 190

Met Val Glu Ala Glu Gly Gly Met Gly Cys Asp Ile Arg Val Asp Glu
        195                 200                 205

Asp Leu Lys Asp Val Ser Ala Asp Val Ile Ala Lys Ala Cys Phe Gly
    210                 215                 220

Ser Asn Phe Ser Lys Gly Lys Ala Ile Phe Ser Lys Ile Arg Asp Leu
225                 230                 235                 240

Leu Thr Ala Ile Thr Lys Arg Ser Val Leu Phe Arg Phe Asn Gly Phe
                245                 250                 255

Thr Asp Met Val Phe Gly Ser Lys Lys His Gly Asp Val Asp Ile Asp
            260                 265                 270
```

Ala Leu Glu Met Glu Leu Glu Ser Ser Ile Trp Glu Thr Val Lys Glu
            275                 280                 285

Arg Glu Arg Glu Cys Lys Asp Thr His Lys Lys Asp Leu Leu Gln Leu
        290                 295                 300

Ile Leu Glu Gly Ala Met Arg Ser Cys Asp Gly Asn Leu Trp Asp Lys
305                 310                 315                 320

Ser Ala Tyr Arg Arg Phe Val Val Asp Asn Cys Lys Ser Ile Tyr Phe
                325                 330                 335

Ala Gly His Asp Ser Thr Ala Val Ser Val Ser Trp Cys Leu Met Leu
            340                 345                 350

Leu Ala Leu Asn Pro Ser Trp Gln Glu Lys Ile Arg Asp Glu Ile Leu
        355                 360                 365

Ser Ser Cys Lys Asn Gly Ile Pro Asp Ala Glu Ser Ile Pro Asn Leu
370                 375                 380

Lys Thr Val Thr Met Val Ile Gln Glu Thr Met Arg Leu Tyr Pro Pro
385                 390                 395                 400

Ala Pro Gly Val Gly Arg Glu Ala Ser Lys Asp Ile Arg Leu Gly Asp
                405                 410                 415

Leu Val Val Pro Lys Gly Val Cys Ile Trp Thr Leu Ile Pro Ala Leu
            420                 425                 430

His Arg Asp Pro Glu Ile Trp Gly Pro Asp Ala Asn Asp Phe Lys Pro
        435                 440                 445

Glu Arg Phe Ser Glu Gly Ile Ser Lys Ala Cys Lys Tyr Pro Gln Ala
        450                 455                 460

Tyr Ile Pro Phe Gly Leu Gly Pro Arg Thr Cys Val Gly Lys Asn Phe
465                 470                 475                 480

Gly Met Met Glu Val Lys Val Leu Val Ser Leu Ile Val Ser Lys Phe
                485                 490                 495

Ser Phe Thr Leu Ser Pro Thr Tyr Gln His Ser Pro Ser His Lys Leu
            500                 505                 510

Leu Val Glu Pro Gln His Gly Val Val Ile Arg Val Val
        515                 520                 525

<210> SEQ ID NO 14
<211> LENGTH: 1578
<212> TYPE: DNA
<213> ORGANISM: Artificial Sequence
<220> FEATURE:
<223> OTHER INFORMATION: kaurenoic acid 13-hydroxylase encoding sequence
      optimized for expression in Yarrowia lipolitica

<400> SEQUENCE: 14
atggagtctc tggttgtcca caccgtcaac gccatctggt gcattgtcat tgtcggtatc        60
ttctccgtcg gctaccacgt ctacggccga gccgttgtcg agcagtggcg aatgcgacga       120
tctctcaagc tccagggtgt caagggtcct cctccctcca tcttcaacgg taacgtttcc       180
gagatgcagc gaatccagtc cgaggccaag acaactccg gtgacaacat catctcccac       240
gactactcct ccactctctt ccccccacttt gaccactggc gaaagcagta cggccgaatc       300
tacacctact ccaccggtct gcgacagcac ctctacatca accacccga tggtcaag         360 gaactgtccc agaccaactc tctcgatctc ggtcgaatca cccacatcac caagcgactc       420
gcccccattc tcggcaacgg tatcatcacc tccaacggcc ccactgggc ccaccagcga       480 cgaatcattg cttacgagtt cacccacgac aaggtcaagg gtatggtcgg cctcatggtc       540
gagtccgcca tgcccatgct caacaagtgg gaggagatgg tcgaggctga gggtggtatg       600

-continued

```
ggctgtgaca tccgagtcga cgaggacctc aaggacgttt ctgccgatgt cattgccaag      660
gcctgctttg gctccaactt ctccaagggc aaggccattt tctccaagat ccgagatctg      720
ctcaccgcca ttaccaagcg atccgtcctc ttccgattca acggtttcac cgacatggtt      780
ttcggctcca agaagcacgg tgacgttgac attgatgctc tcgagatgga gctggagtcc      840
tccatctggg agactgtcaa ggagcgagag cgagagtgca aggacaccca caagaaggac      900
ctcctccagc tcattctcga gggtgccatg cgatcttgtg acggtaacct gtgggacaag      960
tccgcctacc gacgatttgt tgttgacaac tgcaagtcca tctactttgc cggccacgac     1020
tccaccgccg tttctgtctc ttggtgcctc atgctgctgg ctctcaaccc ctcttggcag     1080
gagaagatcc gtgacgagat tctctcttct tgtaagaacg gtatcccga tgctgagtcc      1140 atccccaacc tcaagaccgt caccatggtc atccaggaga ctatgcgact ctaccctccc     1200
gctcccggtg tcggccgaga ggcctccaag gacatccgac tcggtgatct cgttgtcccc     1260
aagggtgtct gcatctggac cctcatcccc gctctgcacc gggacccga aatctggggc      1320 cccgacgcca acgacttcaa gcccgagcga ttctccgagg gtatctccaa ggcttgcaag     1380 taccccagg cctacatccc cttcggtctg ggccccgaa cctgtgtcgg caagaacttc       1440
ggtatgatgg aggtcaaggt ccttgtctct ctcattgtct ccaagttctc cttcactctg     1500
tctcccacct accagcactc tccctcccac aagctcctcg ttgagcccca gcacggtgtt     1560
gtcatccgag tggtgtaa                                                   1578
```

<210> SEQ ID NO 15
<211> LENGTH: 1503
<212> TYPE: DNA
<213> ORGANISM: Artificial sequence
<220> FEATURE:
<223> OTHER INFORMATION: hydroxymethylglutaryl-CoA reductase from
      Yarrowia lipolitica, CpO for expression in Yarrowia lipolitica

<400> SEQUENCE: 15

```
atgacccagt ctgtgaaggt ggttgagaag cacgttccta tcgtcattga aagcccagc       60 gagaaggagg aggacaccct cttctgaagac tccattgagc tgactgtcgg aaagcagccc     120
aagcccgtga ccgagacccg ttctctggac gacttggagg ctatcatgaa ggcaggtaag     180
accaagctcc tggaggacca cgaggttgtc aagctctctc tcgaaggcaa gctcccttg      240 tatgctcttg agaagcagct tggtgacaac acccgagctg ttggcatccg acgatctatc     300
atctcccagc agtctaatac caagactctt gagacctcaa agctccctta cctgcactac     360
gactacgacc gtgttttggg agcctgttgc gagaacgtta ttggttacat gcctctcccc     420
gttggtgttg ctggccccat gaacattgat ggcaagaact accacattcc tatggccacc     480
actgagggtt gtcttgttgc ctcaaccatg cgaggttgca aggccatcaa cgccggtggc     540
ggtgttacca ctgtgcttac tcaggacggt atgacacgag tccttgtgt tccttcccc      600 tctctcaagc gggctggagc cgctaagatc tggcttgatt ccgaggaggg tctcaagtcc     660
atgcgaaagg ccttcaactc cacctctcga tttgctcgtc tccagtctct tcactctacc     720
cttgctggta acctgctgtt tattcgattc gaaccacca ctggtgatgc catgggcatg      780
aacatgatct ccaagggcgt cgaacactct ctggccgtca tggtcaagga gtacggcttc     840
cctgatatgg acattgtgtc tgtctcgggt aactactgca ctgacaagaa gcccgcagcg     900
atcaactgga tcgaaggccg aggcaagagt gttgttgccg aagccaccat ccctgctcac     960
attgtcaagt ctgttctcaa aagtgaggtt gacgctcttg ttgagctcaa catcagcaag    1020
```

```
aatctgatcg gtagtgccat ggctggctct gtgggaggtt tcaatgcaca cgccgcaaac    1080
ctggtgaccg ccatctacct tgccactggc caggatcctg ctcagaatgt cgagtcttcc    1140
aactgcatca cgctgatgag caacgtcgac ggtaacctgc tcatctccgt ttccatgcct    1200
tctatcgagg tcggtaccat tggtggaggt actattttgg agccccaggg tgctatgctg    1260
gagatgcttg gcgtgcgagg tcctcacatc gagaccccg tgccaacgc caacagctt      1320 gctcgcatca ttgcttctgg agttcttgca gcggagcttt cgctgtgttc tgctcttgct    1380
gccggccatc ttgtgcaaag tcatatgacc cacaaccgtt cccaggctcc tactccggcc    1440
aagcagtctc aggccgatct gcagcgtctc caaaacggtt cgaatatctg cattcggtca    1500
tag                                                                  1503

<210> SEQ ID NO 16
<211> LENGTH: 984
<212> TYPE: DNA
<213> ORGANISM: Artificial sequence
<220> FEATURE:
<223> OTHER INFORMATION: Geranylgeranyl diphosphate synthase from
      Yarrowia lipolitica CpO for expression in Yarrowia lipolitica

<400> SEQUENCE: 16
atggattata acagcgcgga tttcaaggag atctggggca aggccgccga caccgcgctg     60
ctgggaccgt acaactacct cgccaacaac cggggccaca acatcagaga acacttgatc    120
gcagcgttcg gagcggttat caaggtggac aagagcgatc tcgaaaccat ttcgcacatc    180
accaagattt tgcataactc gtcgctgctt gttgatgacg tggaagacaa ctcgatgctc    240
cgacgaggcc tgccggcagc ccattgtctg tttggagtcc cccaaaccat caactccgcc    300
aactacatgt actttgtggc tctgcaggag gtgctcaagc tcaagtctta tgatgccgtc    360
tccattttca ccgaggaaat gatcaacttg catagaggtc agggtatgga tctctactgg    420
agagaaacac tcacttgccc ctcggaagac gagtatctgg agatggtggt gcacaagacc    480
ggaggactgt ttcggctggc tctgagactt atgctgtcgg tggcatcgaa acaggaggac    540
catgaaaaga tcaactttga tctcacacac cttaccgaca cactgggagt catttaccag    600
attctggatg attacctcaa cctgcagtcc acggaattga ccgagaacaa gggattctgc    660
gaagatatca gcgaaggaaa gttttcgttt ccgctgattc acagcatccg gaccaacccg    720
gataaccacg agattctcaa cattctcaaa cagcgaacaa gcgacgcttc actcaaaaag    780
tacgccgtgg actacatgag aacagaaacc aagagtttcg actactgcct caagagaatc    840
caggccatgt cactcaaggc aagttcgtac attgatgatc tcgcagcagc cggccacgat    900
gtctccaagt tgcgagccat tttgcattat tttgtgtcca cctctgactg tgaggagaga    960
aagtactttg aggatgcgca gtga                                            984

<210> SEQ ID NO 17
<211> LENGTH: 927
<212> TYPE: DNA
<213> ORGANISM: Artificial sequence
<220> FEATURE:
<223> OTHER INFORMATION: geranylgeranyl diphosphate synthase from Mucor
      circenelloides, codon optimized for expression in Yarrowia
      lipolitica.

<400> SEQUENCE: 17
atgctagcca caaaaatgct caactctcac aaccgaaccg aggagcgatc caccgaggat     60
attattctcg agccttacac ctacctcatt tctcagcccg gaaaggacat tcgagctaag    120
```

```
ctcatttctg cctttgacct ctggctgcac gttcctaagg atgttctttg cgtcatcaac      180
aagattatcg gtatgctgca caacgcctct cttatgattg acgatgttca ggacgactct      240
gatctccgac gaggagtccc cgttgctcac cacatttacg gtgtccctca gactattaac      300
accgctaact acgtgatttt cctcgcccct caggaggtta tgaagctgaa catcccttct      360
atgatgcagg tgtgtaccga ggagcttatt aacctccacc gaggtcaggg aattgagctg      420
tactggcgag attccctcac ttgtcccact gaggaggagt acattgatat ggttaacaac      480
aagacctctg gcctccttcg acttgccgtc cgactgatgc aggctgcttc tgagtccgac      540
atcgactaca cccctctcgt caacattatc ggaattcact tccaggttcg agatgactac      600
atgaacctcc agtccacctc ttacactaac aacaagggct tttgcgagga cctgaccgag      660
ggaaagttct ccttccctat tattcacgct attcgaaagg acccctctaa ccgacagctc      720
ctgaacatta tctctcagaa gcccacctcc attgaggtta agaagtacgc tcttgaggtg      780
atccgaaagg ctggatcttt tgagtacgtt cgagagttcc ttcgacagaa ggaggctgag      840
tccctgaagg agatcaagcg acttggcggc aaccctctcc tcgagaagta cattgagact      900
attcgagtcg aggctactaa cgactaa                                          927
```

<210> SEQ ID NO 18
<211> LENGTH: 2232
<212> TYPE: DNA
<213> ORGANISM: Artificial sequence
<220> FEATURE:
<223> OTHER INFORMATION: Copalyl pyrophosphate synthase from Stevia rebaudiana CpO for expression in Yarrowia lipolitica

<400> SEQUENCE: 18

```
atgtgcaagg ctgttccaa ggagtactcc gatctgctcc agaaggacga ggcctctttc       60
accaagtggg acgacgacaa ggtcaaggac cacctcgaca ccaacaagaa cctctacccc      120
aacgacgaga tcaaggagtt tgtcgagtcc gtcaaggcca tgttcggctc catgaacgac      180
ggcgagatta atgtctctgc ttacgacacc gcctgggttg ctctggtcca ggatgtcgac      240
ggttccggct ctcctcagtt cccttcctct ctcgagtgga tcgccaacaa ccagctgtcc      300
gacggttctt ggggtgacca cctgctcttc tctgctcacg accgaatcat caacaccctg      360
gcctgtgtca ttgctctgac ctcttggaac gtccaccccct ccaagtgcga aagggtctg      420 aacttcctcc gagagaacat ctgcaagctc gaggacgaga acgccgagca catgcccatt      480
ggcttcgagg tcaccttccc ctctctgatt gacattgcca agaagctcaa cattgaggtc      540
cccgaggaca cccccgctct caaggagatc tacgctcgac gagacatcaa gctcaccaag      600
atccccatgg aggttctcca aggtcccc accactctcc tccactctct cgagggtatg      660
cccgatctcg agtgggagaa gctgctcaag ctgcagtgca aggacggctc tttcctcttc      720
tccccctctt ccactgcctt cgccctcatg cagaccaagg acgagaagtg tctccagtac      780
ctcaccaaca ttgtcaccaa gttcaacggt ggtgtcccca cgtctacccc cgttgacctc      840
tttgagcaca tctgggttgt tgaccgactc cagcgactcg gtatcgcccg atacttcaag      900
tccgagatca aggactgtgt cgagtacatc aacaagtact ggaccaagaa cggtatctgc      960
tgggcccgaa acacccacgt ccaggacatt gacgacaccg ccatgggctt ccgagttctg     1020
cgagcccacg gctacgatgt caccccgat gtctttcgac agtttgagaa ggacggcaag     1080
tttgtctgtt cgccggtca gtccaccag gccgtcaccg gtatgttcaa cgtctaccga     1140
gcttctcaga tgctcttccc cggtgagcga atcctcgagg acgccaagaa gttctcctac     1200
```

```
aactacctca aggagaagca gtccaccaac gagctgctcg acaagtggat cattgccaag    1260
gatctgcccg gtgaggttgg ctacgccctc gacatcccct ggtacgcctc tctgccccga    1320
ctggagactc gatactacct cgagcagtac ggtggtgagg acgatgtctg gatcggtaag    1380
accctgtacc gaatgggcta cgttccaaac aacacctacc tcgagatggc caagctcgac    1440
tacaacaact acgttgccgt cctccagctc gagtggtaca ccatccagca gtggtacgtc    1500
gacattggta tcgagaagtt cgagtccgac aacatcaagt ccgtccttgt ctcctactac    1560
ctcgctgctg cctccatctt cgagcccgag cgatccaagg agcgaattgc ctgggccaag    1620
accaccatcc tcgtcgacaa gatcacctcc atcttcgact cctcccagtc ctccaaggaa    1680
gatatcaccg ccttcattga caagttccga aacaagtcct cctccaagaa gcactccatc    1740
aacggcgagc cctggcacga ggtcatggtt gctctcaaga aaactctcca cggctttgcc    1800
ctcgacgctc tgatgaccca ctctcaggac atccaccccc agctccacca ggcctgggag    1860
atgtggctca ccaagctcca ggacggtgtt gatgtcactg ctgagctcat ggtccagatg    1920
atcaacatga ccgccggccg atgggtttcc aaggagctcc tcacccaccc ccagtaccag    1980
cgactctcca ctgtcaccaa ctctgtctgc cacgacatca ccaagctcca caacttcaag    2040
gagaactcca ccaccgtcga ctccaaggtc caggagctgg tccagctcgt tttctccgac    2100 accccgatg atctcgacca ggacatgaag cagaccttcc tgactgtcat gaaaactttc    2160
tactacaagg cctggtgcga ccccaacacc atcaacgacc acatctccaa ggtctttgag    2220
attgtgattt aa                                                        2232
```

<210> SEQ ID NO 19  
<211> LENGTH: 2274  
<212> TYPE: DNA  
<213> ORGANISM: Artificial sequence  
<220> FEATURE:  
<223> OTHER INFORMATION: Kaurene synthase from Stevia rebaudiana CpO for expression in Yarrowia lipolitica

<400> SEQUENCE: 19

```
atgacctccc acggcggcca gaccaacccc accaacctca tcattgacac caccaaggag     60
cgaatccaga agcagttcaa gaacgtcgag atctccgttt cctcctacga caccgcctgg    120
gtcgccatgg tcccctctcc caactccccc aagtctccct gcttccccga gtgtctcaac    180
tggctcatca caaccagct caacgacggc tcttggggtc tggtcaacca cacccacaac    240
cacaaccacc cctcctcaa ggactctctc tcttccactc tcgcctgcat tgttgctctc    300
aagcgatgga acgttggcga ggaccagatc aacaaggtc tgtctttcat tgagtccaac    360
ctcgcctccg ccaccgagaa gtcccagccc tcccccattg gctttgatat catcttcccc    420
ggtctgctcg agtacgccaa gaacctcgat atcaacctgc tctccaagca gaccgacttc    480
tctctcatgc tgcacaagcg agagctcgag cagaagcgat gccactccaa cgagatggac    540
ggctacctgg cctacatttc cgagggtctg gtaacctct cgactggaa catggtcaag    600 aagtaccaga tgaagaacgg ttccgttttc aactcccct ctgccaccgc tgctgccttc    660
atcaaccacc agaaccccgg ctgtctcaac tacctcaact ctctgctcga caagtttggt    720
aacgccgtcc ccactgtcta cccccacgat ctcttcatcc gactctccat ggtcgacacc    780
attgagcgac tcggtatttc ccaccacttc cgagtcgaga tcaagaacgt tctcgatgag    840
acttaccgat gctgggttga gcgagatgag cagatcttca tggacgttgt cacctgtgct    900
ctggccttcc gactcctccg aatcaacggt tacgaggttt cccccgaccc cctcgccgag    960
```

```
atcaccaacg agctggctct caaggacgag tacgccgccc tcgagactta ccacgcttct    1020
cacattctgt accaagagga tctgtcctcc ggcaagcaga ttctcaagtc cgccgacttc    1080
ctcaaggaga tcatctccac tgactccaac cgactctcca agctcatcca aaggaagtc    1140 gagaacgctc tcaagttccc catcaacacc ggtctggagc gaatcaacac ccgacgaaac    1200
atccagctct acaacgtcga caacacccga attctcaaga ccacctacca ctcttccaac    1260
atctccaaca ccgactacct gcgactcgcc gtcgaggact ctacacctg ccagtccatc     1320 taccgagagg agctcaaggg tctggagcga tgggttgtcg agaacaagct cgaccagctc    1380
aagtttgccc gacaaaagac tgcctactgc tacttctccg ttgctgccac cctctcttct    1440
cccgagctct ccgacgcccg aatctcttgg gccaagaacg gtatcctgac cactgttgtc    1500
gacgacttct ttgacattgg tggcaccatt gacgagctga ccaacctcat ccagtgcgtc    1560
gagaagtgga acgtcgacgt tgacaaggac tgttgttccg agcacgtccg aatcctcttc    1620
ctggctctca aggacgccat ctgctggatc ggtgacgagg ccttcaagtg caggctcga    1680 gatgtcactt cccacgtcat ccagacctgg ctcgagctca tgaactccat gctgcgagag    1740
gccatctgga cccgagatgc ctacgtcccc accctcaacg agtacatgga gaacgcctac    1800
gtcagctttg ctctcggtcc cattgtcaag cccgccatct actttgtcgg tcccaagctg    1860
tccgaggaga ttgtcgagtc ctccgagtac cacaacctct tcaagctcat gtccacccag    1920
ggccgactcc tcaacgatat ccactccttc aagcgagagt tcaaggaagg taagctcaac    1980
gccgttgctc tgcacctgtc caacggtgag tccggcaagg tcgaggaaga ggtcgtcgag    2040
gagatgatga tgatgatcaa gaacaagcga aaggagctca tgaagctcat cttcgaggag    2100
aacggctcca ttgtccccg agcctgcaag gacgccttct ggaacatgtg ccacgtcctc    2160
aacttcttct acgccaacga cgacggtttc accggcaaca ccattctcga caccgtcaag    2220
gacatcatct acaaccctct ggttctggtc aacgagaacg aggagcagag gtaa          2274
```

<210> SEQ ID NO 20
<211> LENGTH: 1578
<212> TYPE: DNA
<213> ORGANISM: Artificial sequence
<220> FEATURE:
<223> OTHER INFORMATION: Kaurene oxidase from Giberella fujikuroi CpO
      for expression in Yarrowia lipolitica

<400> SEQUENCE: 20

```
atgtccaagt ccaactccat gaactccacc tcccacgaga ctctcttcca gcagctcgtt      60
ctcggcctcg accgaatgcc cctcatggac gtccactggc tcatctacgt tgccttggt     120 gcctggctct gctcctacgt catccacgtt ctgtcctctt cctccactgt caaggtcccc    180
gtcgtcggtt accgatccgt tttcgagccc acctggctcc tccgactgcg attcgtctgg    240
gagggtggtt ccatcattgg ccagggctac aacaagttca aggactccat cttccaggtc    300
cgaaagctcg gtaccgacat tgtcatcatc cctcccaact acattgacga ggtccgaaag    360
ctctcccagg acaagacccg atccgtcgag ccctcatca acgactttgc cggccagtac    420
acccgaggta tggtctttct gcagtccgat ctccagaacc gagtcatcca gcagcgactc    480 accccccaagc ttgtctctct caccaaggtc atgaaggag agctcgacta cgtctctgacc    540 aaggagatgc ccgacatgaa gaacgacgag tgggttgagg tcgacatctc ttccatcatg    600
gtccgactca tctctcgaat ctccgcccga gttttcctcg gccccgagca tgccgaaac     660 caggagtggc tcaccaccac cgccgagtac tccgagtctc tcttcatcac cggcttcatc    720
```

```
ctccgagttg tcccccacat tctccgaccc ttcattgctc ctctgctgcc ctcttaccga    780
accctgctgc gaaacgtttc ttccggccga cgagtcattg gtgatatcat ccgatcccag    840
cagggtgacg gtaacgagga catcctctct tggatgcgag atgctgccac tggtgaggag    900
aagcagatcg acaacattgc ccagcgaatg ctcattctgt ctctcgcctc catccacacc    960
accgccatga ccatgaccca cgccatgtac gatctgtgtg cctgccccga gtacattgag   1020
cccctccgag atgaggtcaa gtccgtcgtt ggtgcttctg gctgggacaa gaccgctctc   1080
aaccgattcc acaagctcga ctctttcctc aaggagtccc agcgattcaa cccgttttc    1140 ctgctcacct tcaaccgaat ctaccaccag tccatgaccc tctccgatgg taccaacatc   1200
ccctccggta cccgaattgc tgtcccctct cacgccatgc tccaggactc cgcccacgtc   1260
cccggtccca ctcctcccac tgagttcgac ggtttccgat actccaagat ccgatccgac   1320
tccaactacg cccagaagta cctcttctcc atgaccgact cttccaacat ggcctttggc   1380
tacggtaagt acgcctgccc cggccgattc tacgcctcca cgagatgaa gctgactctg    1440 gccattctgc tcctccagtt tgagttcaag ctccccgacg gtaagggccg accccgaaac   1500
atcaccatcg actccgacat gatccccgac cccgagctc gactctgtgt ccgaaagcga    1560
tctctgcgtg acgagtaa                                                 1578

<210> SEQ ID NO 21
<211> LENGTH: 2136
<212> TYPE: DNA
<213> ORGANISM: Artificial sequence
<220> FEATURE:
<223> OTHER INFORMATION: Cytochrome P450 reductase from Arabidopsis
      thaliana CpO for expression in Yarrowia lipolitica

<400> SEQUENCE: 21
atgtcctcct cttcttcttc ttccacctcc atgattgatc tcatggctgc catcatcaag     60
ggtgagcccg tcattgtctc cgaccccgcc aacgcctccg cctacgagtc cgttgctgcc    120
gagctgtcct ccatgctcat cgagaaccga cagtttgcca tgatcgtcac cacctccatt    180
gctgttctca ttggctgcat tgtcatgctc gtctggcgac gatctggctc cggtaactcc    240
aagcgagtcg agcccctcaa gcccctggtc atcaagcccc gagaagagga gatcgacgac    300
ggccgaaaga aggtcaccat cttcttttgg cacccagacc gtactgctga gggcttcgcc    360
aaggctctcg gtgaggaagc caaggctcga tacgaaaaga cccgattcaa gattgtcgac    420
ctcgatgatt acgctgccga tgacgacgag tacgaggaga gctcaagaa agaggacgtt    480 gccttcttct cctcgccac ctacggtgac ggtgagccca ccgacaacgc tgcccgattc    540
tacaagtggt tcaccgaggg taacgaccga ggcgagtggc tcaagaacct caagtacggt    600
gttttcggtc tgggcaaccg acagtacgag cacttcaaca aggttgccaa ggttgtcgac    660
gacatcctcg tcgagcaggg tgcccagcga ctcgtccagg tcggcctcgg tgatgatgac    720
cagtgcatcg aggacgactt cactgcctgg cgagaggctc tgtggccga gctcgacacc    780 attctgcgag aggaaggtga caccgccgtt gccaccccct acaccgccgc cgtcctcgag    840
taccgagtct ccatccacga ctccgaggat gccaagttca cgacatcaa catggccaac    900 ggtaacggct acaccgtctt tgacgcccag caccctaca aggccaacgt cgccgtcaag    960
cgagagctcc acacccccga gtccgaccga tcttgtatcc acctcgagtt tgacattgct   1020
ggttccggtc tgacctacga gactggtgac acgttggtg tcctctgtga caacctgtcc    1080
gagactgtcg acgaggctct gcgactcctc gacatgtccc ccgacactta cttctctctg   1140
```

```
cacgccgaga aagaggacgg tactcccatc tcttcttctc tgcccctcc cttccctccc   1200 tgcaacctgc gaaccgctct gacccgatac gcctgcctcc tctcttctcc caagaagtct   1260
gctctcgttg ctctggccgc ccacgcctcc gacccaccg aggctgagcg actcaagcac    1320
ctcgcctctc ccgctggcaa ggacgagtac tccaagtggg ttgtcgagtc ccagcgatct   1380
ctgctcgagg tcatggccga gttccctcc gccaagcccc ctctcggtgt tttcttcgcc    1440
ggtgttgctc cccgactcca gccccgattc tactccatct cctcttcccc caagatcgcc   1500
gagactcgaa tccacgttac ctgtgctctg gtctacgaga agatgcccac cggccgaatc   1560
cacaagggtg tctgctccac ctggatgaag aacgccgttc cctacgagaa gtccgagaac   1620
tgttcctctg ctcccatctt tgtccgacag tccaacttca agctcccctc cgactccaag   1680
gtccccatca tcatgattgg ccccggtacc ggcctcgccc ccttccgagg cttcctgcag   1740
gagcgactcg ccctcgtcga gtccggtgtc gagctcggcc cctccgtcct cttctttggc   1800
tgccgaaacc gacgaatgga cttcatctac gaagaggagc tccagcgatt cgtcgagtcc   1860
ggtgctctcg ccgagctctc cgttgccttc tcccgagagg gtcccaccaa ggagtacgtc   1920
cagcacaaga tgatggacaa ggcctccgac atctggaaca tgatctccca gggcgcctac   1980
ctctacgtct gcggtgacgc caagggtatg gcccgagatg tccaccgatc tctgcacacc   2040
attgcccagg agcagggctc catggactcc accaaggccg agggtttcgt caagaacctc   2100
cagacctccg gccgatacct ccgagatgtc tggtaa                              2136

<210> SEQ ID NO 22
<211> LENGTH: 1446
<212> TYPE: DNA
<213> ORGANISM: Artificial sequence
<220> FEATURE:
<223> OTHER INFORMATION: UDP-glucosyltransferase from Stevia rebaudiana
      Cpo for expression in Yarrowia lipolitica

<400> SEQUENCE: 22
atggacgcca tggccaccac cgagaagaag ccccacgtca tcttcatccc cttccccgcc     60
cagtcccaca tcaaggccat gctcaagctc gcccagctcc tccaccacaa gggcctccag    120
atcacctttg tcaacaccga cttcatccac aaccagttcc tcgagtcctc cggccccac    180 tgtctggacg gtgctcccgg tttccgattt gagactatcc ccgatggtgt ctcccactcc    240
cccgaggcct ccatccccat ccgagagtct ctgctccgat ccattgagac taacttcctc    300
gaccgattca ttgatctcgt caccaagctc cccgatcctc ccacctgtat catctccgac    360
ggtttcctgt ccgttttcac cattgatgct gccaagaagc tcggtatccc cgtcatgatg    420
tactggactc tggctgcctg tggttcatg ggtttctacc acatccactc tctgatcgag    480
aagggctttg ctcctctcaa ggacgcctcc tacctcacca cggttacct cgacaccgtc    540 attgactggg tccccggtat ggagggtatc cgactcaagg acttcccct cgactggtcc    600 accgacctca cgacaaggt tctcatgttc accaccgagg ctcccagcg atcccacaag     660 gtttcccacc acatcttcca caccttcgac gagctcgagc cctccatcat caagactctg    720
tctctgcgat acaaccacat ctacaccatt ggccccctcc agctcctcct cgaccagatc    780
cccgaggaga agaagcagac cggtatcacc tctctgcacg ctactctctc cgtcaaggaa    840
gagcccgagt gcttccagtg gctccagtcc aaggagccca actccgttgt ctacgtcaac    900
tttggctcca ccaccgtcat gtctctcgag gacatgaccg agtttggctg gggtctggcc    960
aactccaacc actacttcct gtggatcatc cgatccaacc tcgtcattgg cgagaacgcc   1020
```

```
gttctgcctc cgagctcga ggagcacatc aagaagcgag gcttcattgc ctcttggtgc      1080
tcccaggaga aggttctcaa gcacccctcc gtcggtggtt tcctgaccca ctgcggctgg      1140
ggctccacca ttgagtctct gtccgctggt gtccccatga tctgctggcc ctactcctgg      1200
gaccagctca ccaactgccg atacatctgc aaggagtggg aggttggtct ggagatgggt      1260
accaaggtca agcgagatga ggtcaagcga ctcgtccagg agctcatggg cgagggtggt      1320
cacaagatgc gaaacaaggc caaggactgg aaggagaagg cccgaattgc cattgccccc      1380
aacggctctt cttctctcaa cattgacaag atggtcaagg agatcactgt tctcgctcga      1440
aactaa                                                                1446
```

<210> SEQ ID NO 23
<211> LENGTH: 1422
<212> TYPE: DNA
<213> ORGANISM: Artificial sequence
<220> FEATURE:
<223> OTHER INFORMATION: variant of UDP-glucosyltransferase from Stevia rebaudiana Cpo for expression in Yarrowia lipolitica

<400> SEQUENCE: 23

```
atggccacct ccgactccat tgttgacgac cgaaagaagc tccacattgt catgttcccc       60
tggctcgcct ttggccacat catccccat ctcgagcttt ccaagctcat tgcccagaag      120
ggccacaagg tttccttcct ctccaccacc aagaacattg accgactctc ctcccacatc      180
tctcccctca tcaactttgt caagctcacc ctcccccgag tccaggagct gcccgaggac      240
gccgaggcca ccactgatgt ccaccccgag gatatcccct acctcaagaa ggcctccgac      300
ggcctccagc ccgaggtcac tgagttcctc gagcagcact ctcccgactg gatcatctac      360
gactacaccc actactggct ccccgagatt gccaagtctc tcggtgtctc tcgagcccac      420
ttctccgtca ccacccctg ggccattgct acatgggtc ccactgccga tgccatgatc       480
aacggttccg actaccgaac cgagcttgag gacttcaccg tccctcccaa gtggttcccc      540
ttccccacca ccgtctgctg gcgaaagcac gatctggccc gactcgtccc ctacaaggct      600
cccggtatct ccgacggtta ccgaatgggc ctcgtcatca agggctgcga ctgtctgctc      660
tccaagacct accacgagtt cggtactcag tggctccgac ttctcgagga gctgcaccga      720
gtccccgtca tccccgttgg tctgctcccct cctccatcc ccggctctga caaggacgac      780
tctggggttt ccatcaagga gtggctcgac ggccaggaga agggctccgt tgtctacgtt      840
gctctcggtt ccgaggttct cgtcacccag gaagaggttg tcgagcttgc tcacggtctg      900
gagctgtccg gtctgccctt cttctgggcc taccgaaagc ccaagggtcc cgccaagtcc      960
gactccgtcg agcttcccga tggtttcgtc gagcgagtcc gagatcgagg tctggtctgg     1020
acctcttggg ctccccagct ccgaatcctc tcccacgagt ccgttgctgg ttcctcacc     1080 cactgcggtt ccggctccat tgtcgagggc ctcatgttcg gccaccctct catcatgctc     1140
cccatcttcg gtgaccagcc cctcaacgcc cgactccttg aggacaagca ggtcggtatc     1200
gagatccccc gaaacgagga agatggttct ttcacccgag actctgttgc cgagtctctg     1260
cgactcgtca tggtcgagga gagggtaag atctaccgag agaaggccaa ggagatgtcc     1320
aagctctttg cgacaaggaa cctccaggac cagtacgtcg acgactttgt cgagtacctc     1380
cagaagcacc gacgagctgt tgccattgac cacgaaagct aa                        1422
```

<210> SEQ ID NO 24
<211> LENGTH: 1383
<212> TYPE: DNA

```
<213> ORGANISM: Artificial sequence
<220> FEATURE:
<223> OTHER INFORMATION: UDP-glucosyltransferase from Stevia rebaudiana
      Cpo for expression in Yarrowia lipolitica

<400> SEQUENCE: 24
atggccgagc agcagaagat caagaagtct ccccacgttc tgctcatccc cttccctctg      60
cagggccaca tcaaccccct catccagttc ggcaagcgac tcatctccaa gggtgtcaag     120
accactctgg tcaccaccat ccacaccctc aactccactc tcaaccactc caacaccacc     180
accacctcca tcgagatcca ggccatctcc gacggctgtg acgagggtgg tttcatgtct     240
gctggtgagt cttacctcga gactttcaag caggtcggtt ccagtctct ggctgacctc      300
atcaagaagc tccagtccga gggtaccacc attgacgcca tcatctacga ctccatgacc     360
gagtgggttc tcgatgtcgc catcgagttt ggtattgacg tggctccctt cttcacccag     420
gcctgtgtcg tcaactctct ctactaccac gtccacaagg gtctgatctc tctgcccctc     480
ggcgagactg tctccgtccc cggtttcccc gttctgcagc gatgggagac tcctctcatt     540
ctccagaacc acgagcagat ccagtccccc tggtcccaga tgctcttcgg ccagttcgcc     600
aacattgacc aggcccgatg gttttcacc aactccttct acaagctcga ggaagaggtc      660
attgagtgga cccgaaagat ctggaacctc aaggtcattg gccccaccct ccctccatg      720
tacctcgaca gcgactcga tgacgacaag acaacggtt caacctcta caaggccaac       780
caccacgagt gcatgaactg gctcgacgac aagcccaagg agtccgttgt ctacgttgcc     840
tttggctctc tggtcaagca cggccccgag caggttgagg agatcacccg agctctgatt     900
gactccgatg tcaacttcct gtgggtcatc aagcacaagg aagagggtaa gctccccgag     960
aacctgtccg aggtcatcaa gaccggcaag ggcctcattg ttgcctggtg caagcagctc    1020
gacgttctcg cccacgagtc cgtcggctgc tttgtcaccc actgcggttt caactccacc    1080
ctcgaggcta tctctctcgg tgtccccgtt gttgccatgc cccagttctc cgaccagacc    1140
accaacgcca agctcctcga tgagattctc ggtgtcggtg tccgagtcaa ggctgacgag    1200
aacggtattg tccgacgagg taacctggct tcttgtatca agatgatcat ggaggaagag    1260
cgaggtgtca tcatccgaaa gaacgccgtc aagtggaagg atctggccaa ggttgctgtc    1320
cacgagggtg gctcttccga caacgacatt gtcgagtttg tctccgagct catcaaggcc    1380
taa                                                                  1383

<210> SEQ ID NO 25
<211> LENGTH: 1377
<212> TYPE: DNA
<213> ORGANISM: Artificial sequence
<220> FEATURE:
<223> OTHER INFORMATION: UDP-glucosyltransferase from Stevia rebaudiana
      Cpo for expression in Yarrowia lipolitica

<400> SEQUENCE: 25
atggagaaca agaccgagac taccgtccga cgacgacgac gaatcattct cttccccgtc      60
cccttccagg gccacatcaa ccccattctg cagctcgcca cgttctgta ctccaagggc     120
ttctccatca ccatcttcca caccaacttc aacaagccca gacctccaa ctaccccac      180
ttcactttcc gattcatcct cgacaacgac ccccaggacg agcgaatctc caacctgccc     240
acccacggtc tctggctgg tatgcgaatc cccatcatca cgagcacgg tgctgacgag     300
ctccgacgag agctcgagct gctcatgctc gcctccgaag aggacgagga agtcctcctgt    360
ctgatcaccg atgctctgtg gtactttgcc cagtccgtcg ccgactctct caacctgcga    420
```

```
cgactcgttc tcatgacctc ctctctgttc aacttccacg cccacgtttc tctgccccag    480
tttgacgagc tcggttacct cgaccccgat gacaagaccc gactcgagga gcaggcttcc    540
ggtttcccca tgctcaaggt caaggacatc aagtccgcct actccaactg gcagattctc    600
aaggagattc tcggcaagat gatcaagcag accaaggcct cctccggtgt catctggaac    660
tccttcaagg agctcgagga gtccgagctc gagactgtca tccgagagat ccccgctccc    720
tctttcctca tccccctgcc caagcacctc accgcttcct cctcttctct gctcgaccac    780
gaccgaaccg tctttcagtg gctcgaccag cagcccctt cctccgtcct ctacgtttcc    840
ttcggctcca cctccgaggt cgacgagaag gacttcctcg agattgctcg aggcctcgtt    900
gactccaagc agtccttcct gtgggttgtc cgacccggct ttgtcaaggg ctccacctgg    960
gttgagcccc tgcccgatgg tttcctcggt gagcgaggcc gaattgtcaa gtgggtcccc   1020
cagcaggaag ttctggccca cggtgccatt ggtgccttct ggacccactc cggctggaac   1080
tccactctcg agtccgtctg cgagggtgtc cccatgatct tctccgactt tggcctcgac   1140
cagcccctca acgcccgata catgtccgat gttctcaagg tcggtgtcta cctcgagaac   1200
ggctgggagc gaggtgagat tgccaacgcc atccgacgag tcatggtcga cgaggaaggt   1260
gagtacatcc gacagaacgc ccgagtcctc aagcagaagg ccgatgtctc tctcatgaag   1320
ggtggttctt cttacgagtc tctcgagtct ctcgtttcct acatctcttc tttgtaa     1377
```

KAURENOIC ACID HYDROXYLASES

CROSS-REFERENCE TO RELATED APPLICATIONS

This application is the National Stage entry of International Application No. PCT/EP2017/081390, filed 4 Dec. 2017, which claims priority to European Patent Application No. 16202945.8, filed 8 Dec. 2016.

REFERENCE TO SEQUENCE LISTING SUBMITTED AS A COMPLIANT ASCII TEXT FILE (.txt)

Pursuant to the EFS-Web legal framework and 37 C.F.R. § 1.821-825 (see M.P.E.P. § 2442.03(a)), a Sequence Listing in the form of an ASCII-compliant text file (entitled "2919208-509000_Sequence_Listing_ST25.txt" created on 22 May 2019, and 73,719 bytes in size) is submitted concurrently with the instant application, and the entire contents of the Sequence Listing are incorporated herein by reference.

BACKGROUND

Field

The present disclosure relates to a polypeptide having kaurenoic acid 13-hydroxylase activity and to a nucleic acid comprising a sequence encoding such a polypeptide. The disclosure also relates to a nucleic acid construct comprising the nucleic acid and to an expression vector comprising the nucleic acid or nucleic acid construct. Further, the disclosure relates to a recombinant host comprising the nucleic acid, a nucleic acid construct or expression vector. The disclosure also relates to a process for the preparation of steviol or a steviol glycoside which comprises fermenting a recombinant host, to a fermentation broth obtainable by such a process and to a steviol glycoside obtained by a process or obtained from the fermentation broth. In addition, the disclosure relates to a composition comprising two or more of the steviol glycosides and to a foodstuff, feed or beverage which comprises the steviol glycoside or composition. Further, the disclosure relates to a method for converting a first steviol glycoside into a second steviol glycoside and to a method for the production of a polypeptide having kaurenoic acid 13-hydroxylase activity

Description of Related Art

The leaves of the perennial herb, *Stevia rebaudiana* Bert., accumulate quantities of intensely sweet compounds known as steviol glycosides. Whilst the biological function of these compounds is unclear, they have commercial significance as alternative high potency sweeteners.

These sweet steviol glycosides have functional and sensory properties that appear to be superior to those of many high potency sweeteners. In addition, studies suggest that stevioside can reduce blood glucose levels in Type II diabetics and can reduce blood pressure in mildly hypertensive patients.

Steviol glycosides accumulate in *Stevia* leaves where they may comprise from 10 to 20% of the leaf dry weight. Stevioside and rebaudioside A are both heat and pH stable and suitable for use in carbonated beverages and can be applied in many other foods. Stevioside is between 110 and 270 times sweeter than sucrose, rebaudioside A between 150 and 320 times sweeter than sucrose. In addition, rebaudioside D is also a high-potency diterpene glycoside sweetener which accumulates in *Stevia* leaves. It may be about 200 times sweeter than sucrose. Rebaudioside M is a further high-potency diterpene glycoside sweetener. It is present in trace amounts in certain *stevia* variety leaves, but has been suggested to have a superior taste profile.

Steviol glycosides have traditionally been extracted from the *Stevia* plant. In *Stevia*, (−)-kaurenoic acid, an intermediate in gibberellic acid (GA) biosynthesis, is converted into the tetracyclic diterpene steviol, which then proceeds through a multi-step glycosylation pathway to form the various steviol glycosides. However, yields may be variable and affected by agriculture and environmental conditions. Also, *Stevia* cultivation requires substantial land area, a long time prior to harvest, intensive labour and additional costs for the extraction and purification of the glycosides.

More recently, interest has grown in producing steviol glycosides using fermentative processes. WO2013/110673 and WO2015/007748 describe microorganisms that may be used to produce at least the steviol glycosides rebaudioside A and rebaudioside D.

Further improvement of such microorganisms is desirable in order that higher amounts of steviol glycosides may be produced and/or additional or new steviol glycosides and/or higher amounts of specific steviol glycosides and/or mixtures of steviol glycosides having desired ratios of different steviol glycosides.

SUMMARY

The present disclosure is based on the identification of new kaurenoic acid 13-hydroxylase (KAH) polypeptides, i.e. new polypeptides having KAH activity. These polypeptides may be used in the production of recombinant hosts suitable for the production of steviol and/or one or more steviol glycosides.

Such recombinant hosts may produce higher amounts of steviol glycosides and lower amount of non-desirable products as compared with recombinant hosts expressing a reference kaurenoic acid 13-hydroxylase. Production of higher amounts of steviol glycosides and/or lower amount of non-desirable products may make recovery of steviol glycosides easier. Also, a higher yield may be obtained.

Accordingly, the disclosure relates to a polypeptide having kaurenoic acid 13-hydroxylase activity, which polypeptide comprises an amino acid sequence which, when aligned with a kaurenoic acid 13-hydroxylase comprising the sequence set out in SEQ ID NO: 1 (the wild type KAH sequence from *A. thaliana*) or SEQ ID NO: 3 (KAH4_m4), comprises at least one substitution of an amino acid corresponding to any of amino acids at positions:

136, 248, 336 or 403 said positions being defined with reference to SEQ ID NO: 1 or SEQ ID NO: 3 and wherein the polypeptide has one or more modified properties as compared with a reference polypeptide having kaurenoic acid 13-hydroxylase activity.

The disclosure also relates to:

- a polypeptide having kaurenoic acid 13-hydroxylase activity comprising an amino acid sequence having at least about 95% sequence identity, at least about 96%, at least about 97%, at least about 98% or at least about 99% sequence identity to SEQ ID NO: 5, 7, 9, 11 or 13;
- a nucleic acid comprising a sequence encoding a polypeptide having kaurenoic acid 13-hydroxylase activity of the disclosure;

a nucleic acid construct comprising the nucleic acid of the disclosure, operably linked to one or more control sequences capable of directing the expression of a kaurenoic acid 13-hydroxylase in a suitable expression host;

an expression vector comprising a nucleic acid or a nucleic acid construct according to the disclosure;

a recombinant host comprising a nucleic acid, a nucleic acid construct or an expression vector of the disclosure;

a process for the preparation of steviol or a steviol glycoside which comprises fermenting a recombinant host as disclosed herein in a suitable fermentation medium and, optionally, recovering the steviol or steviol glycoside;

a fermentation broth comprising a steviol glycoside obtainable by the process for the preparation of steviol or a steviol glycoside as disclosed herein;

a steviol glycoside obtained by a process for the preparation of steviol or a steviol glycoside as disclosed herein or obtained from a fermentation broth comprising a steviol glycoside as disclosed herein;

a composition comprising two or more steviol glycosides obtained by a process for the preparation of steviol or a steviol glycoside as disclosed herein or obtained from a fermentation broth comprising a steviol glycoside as disclosed herein;

a foodstuff, feed or beverage which comprises a steviol glycoside obtained by a process for the preparation of steviol or a steviol glycoside as disclosed herein or a composition obtained by a process for the preparation of steviol or a steviol glycoside as disclosed herein or obtained from a fermentation broth comprising a steviol glycoside as disclosed herein;

a method for converting a first steviol glycoside into a second steviol glycoside, which method comprises:
contacting said first steviol glycoside with a recombinant host as disclosed herein, a cell free extract derived from such a recombinant host or an enzyme preparation derived from either thereof;
thereby to convert the first steviol glycoside into the second steviol glycoside; and a method for producing a kaurenoic acid 13-hydroxylase comprising cultivating a host cell as disclosed herein under conditions suitable for production of the kaurenoic acid 13-hydroxylase and, optionally, recovering the kaurenoic acid 13-hydroxylase.

DESCRIPTION OF THE SEQUENCE LISTING

Figure 1:
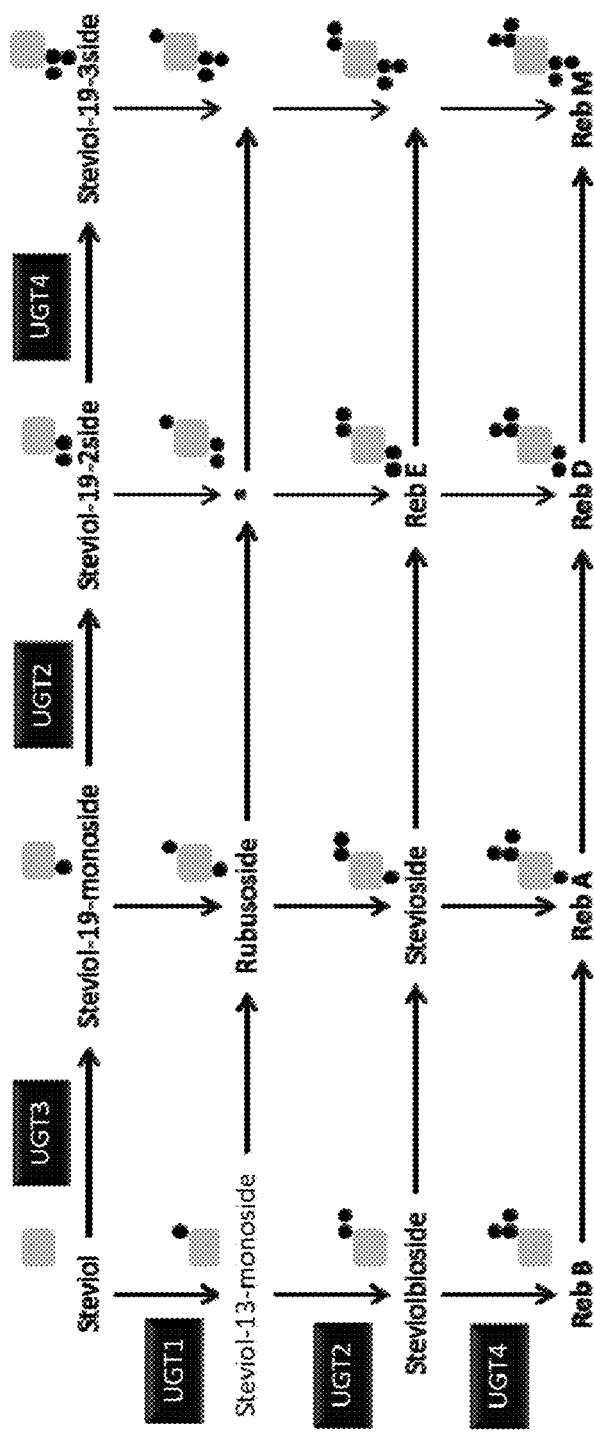
FIG. 1 set out a schematic diagram of some, but not all, of the potential pathways leading to biosynthesis of steviol glycosides.

SEQ ID NO: 1 sets out the amino acid sequence of a kaurenoic acid 13-hydroxylase polypeptide from *Arabidopsis thaliana*.

SEQ ID NO: 2 sets out the nucleotide sequence encoding a kaurenoic acid 13-hydroxylase polypeptide from *Arabidopsis thaliana*, codon-pair optimized for expression in *Yarrowia lipolytica*.

SEQ ID NO: 3 sets out the amino acid sequence of the KAH4_m4 polypeptide.

SEQ ID NO: 4 sets out the nucleotide sequence encoding the KAH4_m4 polypeptide, codon-pair optimized for expression in *Yarrowia lipolytica*.

SEQ ID NOs: 5 to 14 are described in Table 1.

SEQ ID NO: 15 sets out the nucleotide sequence encoding a hydroxymethylglutaryl-CoA reductase polypeptide from *Yarrowia lipolytica*, codon-pair optimized for expression in *Yarrowia lipolytica*

SEQ ID NO: 16 sets out the nucleotide sequence encoding a geranylgeranyl diphosphate synthase polypeptide from *Yarrowia lipolytica*, codon-pair optimized for expression in *Yarrowia lipolytica*.

SEQ ID NO: 17 sets out the nucleotide sequence encoding a geranylgeranyl diphosphate synthase polypeptide from *Mucor circenelloides*, codon optimized for expression in *Yarrowia lipolytica*.

SEQ ID NO: 18 sets out the nucleotide sequence encoding a copalyl pyrophosphate synthase polypeptide from *Stevia rebaudiana*, codon-pair optimized for expression in *Yarrowia lipolytica*.

SEQ ID NO: 19 sets out the nucleotide sequence encoding a kaurene synthase polypeptide from *Stevia rebaudiana*, codon-pair optimized for expression in *Yarrowia lipolytica*.

SEQ ID NO: 20 sets out the nucleotide sequence encoding a kaurene oxidase polypeptide from *Giberella fujikuroi*, codon-pair optimized for expression in *Yarrowia lipolytica*.

SEQ ID NO: 21 sets out the nucleotide sequence encoding a cytochrome P450 reductase polypeptide from *Arabidopsis thaliana*, codon-pair optimized for expression in *Yarrowia lipolytica*.

SEQ ID NO: 22 sets out the nucleotide sequence encoding a UDP-glucosyltransferase polypeptide from *Stevia rebaudiana*, codon-pair optimized for expression in *Yarrowia lipolytica*.

SEQ ID NO: 23 sets out the nucleotide sequence encoding a variant of UDP-glucosyltransferase polypeptide from *Stevia rebaudiana*, codon-pair optimized for expression in *Yarrowia lipolytica*.

SEQ ID NO: 24 sets out the nucleotide sequence encoding a UDP-glucosyltransferase polypeptide from *Stevia rebaudiana*, codon-pair optimized for expression in *Yarrowia lipolytica*.

SEQ ID NO: 25 sets out the nucleotide sequence encoding a UDP-glucosyltransferase polypeptide from *Stevia rebaudiana*, codon-pair optimized for expression in *Yarrowia lipolytica*.

DETAILED DESCRIPTION

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

According to the disclosure, there is thus provided a polypeptide having kaurenoic acid 13-hydroxylase activity. A polypeptide of the disclosure has kaurenoic acid 13-hydroxylase activity. Kaurenoic acid 13-hydroxylase activity is the activity of hydroxylation of (−)-kaurenoic acid at the C-13 position to form steviol.

"Rebaudioside" herein may be abbreviated to "Reb" or "reb" or the like.

Thus, for the purposes of the disclosure, a polypeptide having kaurenoic acid 13-hydroxylase activity may be one which is capable of catalysing or partially catalyzing the formation of steviol (ent-kaur-16-en-13-ol-19-oic acid) from ent-kaurenoic acid. For the purposes of the disclosure therefore, a polypeptide may be one having kaurenoic acid 13-hydroxylase activity is one which is capable of catalysing or partially catalyzing the formation of steviol (ent-kaur-16-en-13-ol-19-oic acid) using NADPH and O2.

Such activity may also be referred to as ent-ka 13-hydroxylase activity or ent-kaurenoic acid 13-hydroxylase activity.

A polypeptide of the disclosure has one or more modified properties as compared with a reference polypeptide having kaurenoic acid 13-hydroxylase activity A polypeptide according to the disclosure may have modified kaurenoic acid 13-hydroxylase activity as compared with a reference polypeptide having kaurenoic acid 13-hydroxylase activity.

Such a polypeptide may have a decreased specific kaurenoic acid 13-hydroxylase activity as compared with the reference polypeptide.

Such a polypeptide may have an increased specific kaurenoic acid 13-hydroxylase activity as compared with the reference polypeptide.

A polypeptide according to the disclosure may be a non-naturally occurring polypeptide.

Herein, polypeptides of the disclosure may be referred to as a "kaurenoic acid 13-hydroxylase" enzyme or polypeptide, "kaurenoic acid hydroxylase" enzyme or polypeptide, "KAH" enzyme or polypeptide or the like.

A KAH polypeptide of the disclosure (for example a polypeptide having one or more substitution as set out herein) may comprise an amino acid sequence having at least about 60%, 70%, 80% identity with the reference KAH polypeptide, such as the KAH of SEQ ID NO: 1 or SEQ ID NO: 3, for example at least about 85% identity with the reference polypeptide, such as at least about 90% identity with the reference polypeptide, at least about 95% identity with the reference polypeptide, at least about 98% identity with the reference polypeptide or at least about 99% identity with the reference polypeptide. Such a KAH polypeptide will typically have one or more substitution or sets of substitutions selected from a position corresponding to 136, 248, 336 or 403 as defined with reference to SEQ ID NO: 1 or SEQ ID NO: 3.

An amino acid position corresponding to one of the positions defined herein in the reference KAH may be a position that aligns in a multiple (protein) sequence alignment with any of the stated amino acid positions.

An amino acid position corresponding to one of the positions 136, 248, 336 or 403, said position being defined with reference to SEQ ID NO: 1 or SEQ ID NO: 3 is a position which is identified in the KAH polypeptide sequence when the latter is aligned with the amino acid sequence set out in SEQ ID NO: 1 or 3 by a suitable sequence alignment method. A suitable sequence alignment method is a method which allows comparison of the sequences with each other and identifications of the positions in the amino acid sequence of KAH polypeptide wherein either the same amino acid is present (identical position), or another amino acid is present (substitution), or one or more extra amino acids are present (insertion or extension) or no amino acid is present (deletion or truncation) if compared with the amino acid sequence set out in SEQ ID NO: 1 or 3.

A suitable method allowing comparison of two amino acid sequence may be any suitable Pairwise Sequence Alignment method known to those skilled in the art, preferably a Global Pairwise Sequence Alignment method. A preferred Global Pairwise Sequence Alignment method is the EMBOSS Needle method based on the Needleman-Wunsch alignment algorithm (aiming at finding the optimum alignment (including gaps) of the two sequences along their entire length) (Needleman, S. B. and Wunsch, C. D. (1970) J. Mol. Biol. 48, 443-453) as described herein. In one embodiment, the amino acid sequence is aligned with the amino acid sequence set out in SEQ ID NO: 1 or 3 using the EMBOSS Needle alignment method using EBLOSUM62 as a substitution matrix, preferably with a gap-open penalty of 10 and a gap extension penalty of 0.5.

In one embodiment according to the disclosure, the positions in the polypeptide having KAH activity corresponding to any amino acids at position 136, 248, 336 or 403, said position being defined with reference to SEQ ID NO: 1 or SEQ ID NO: 3, are identified by aligning the amino acid sequence of the polypeptide with KAH activity of the disclosure with the amino acid sequence set out in SEQ ID NO: 1 or 3 using the EMBOSS Needle alignment method, such as the NEEDLE program from the EMBOSS package, using EBLOSUM62 as a substitution matrix, with a gap-open penalty of 10 and a gap extension penalty of 0.5.

A KAH of the disclosure will typically retain KAH activity. That is to say, a KAH of the disclosure will typically be capable of catalysing the reaction set out above, albeit with a modified activity as compared with a reference polypeptide.

Preferably, a KAH polypeptide of the disclosure will typically exhibit improved properties in comparison with the reference polypeptide from which it is derived, typically in terms of specific activity and/or substrate specificity. Such an improved property will typically be one which is relevant if the KAH were to be used as set out below, for example in a method for the production of steviol and/or a steviol glycoside (by expressing the KAH in a recombinant host).

Thus, a KAH of the disclosure is one which is typically capable of increasing production of steviol and/or a steviol glycoside in a recombinant host capable of the production of said steviol and/or a steviol glycoside (in comparison with a recombinant host capable of the production of steviol and/or a steviol glycoside which expresses the reference polypeptide). That is to say, overexpression of a KAH polypeptide of the disclosure in a host cell will typically lead to increased production of steviol and/or a steviol glycoside as compared to a host cell which overexpresses the host polypeptide (such as the KAH of SEQ ID NO: 1 or SEQ ID NO: 3).

A KAH of the disclosure may be one which is typically capable of decreasing production of a non-steviol glycoside, such as one or more kaurenoic acid glycosides, in a recombinant host capable of the production of steviol and/or a steviol glycoside (in comparison with a recombinant host capable of the production of steviol and/or a steviol glycoside which expresses the reference polypeptide). That is to say, overexpression of a KAH polypeptide of the disclosure in a host cell will typically lead to increased production of steviol and/or a steviol glycoside as compared to a host cell which overexpresses the host polypeptide (such as the KAH of SEQ ID NO: 1 or SEQ ID NO: 3).

Production of lower amounts of non-steviol glycoside products may make recovery of steviol glycosides easier. Also, a higher yield may be obtained.

A KAH which exhibits a property which is improved in relation to the reference KAH is one which demonstrates a measurable reduction or increase in the relevant property, for example specific activity, typically such that the KAH is more suited to a use as set out herein, for example in a method for the production of steviol or a steviol glycoside.

A KAH polypeptide comprises an amino acid sequence that has one or more substitution, deletion and/or insertion of an amino acid as compared to the reference polypeptide and/or one or more truncations as compared to the reference polypeptide. A KAH polypeptide may comprise one or more of the substitutions described herein.

A polypeptide having KAH activity, for example as set out herein, which polypeptide comprises an amino acid sequence which, when aligned with the KAH comprising the sequence set out in SEQ ID NO: 1 or SEQ ID NO: 3, comprises at least one substitution of an amino acid corresponding to any of amino acids 136, 248, 336 or 403 said positions being defined with reference to SEQ ID NO: 1 or SEQ ID NO: 3 and wherein the KAH has one or more modified properties as compared with a reference polypeptide having KAH activity.

Substitution of an amino acid is intended to indicate that the amino acid residue at the specified position is replaced with a different amino acid.

Accordingly, a polypeptide having KAH activity, for example as set out herein, which polypeptide comprises an amino acid sequence which, when aligned with the KAH comprising the sequence set out in SEQ ID NO: 1 or SEQ ID NO: 3, comprises at least one substitution of an amino acid residue corresponding to any of amino acids 136, 248, 336 or 403 said positions being defined with reference to SEQ ID NO: 1 or SEQ ID NO: 3 and wherein the KAH has one or more modified properties as compared with a reference polypeptide having KAH activity.

Thus, the amino acid present at one or more of the said positions will be replaced with a different amino acid than appears at that position in the reference sequence (the positions being defined with reference to SEQ ID NO: 1 or SEQ ID NO: 3).

A KAH of the disclosure may comprise one of the substitutions set out above, or may comprise any combination of two, three or four of them.

A KAH polypeptide of the disclosure may be one wherein:
(i) a methionine (M), valine (V), alanine (A), phenylalanine (F), tryptophan (W), glutamine (Q), histidine (H) or a threonine (T) is present at a position corresponding to 136;
(ii) an asparagine (N), glutamine (Q), threonine (T), glycine (G), alanine (A), isoleucine (I), valine (V), phenylalanine (F) or proline (P) is present at a position corresponding 248;
(iii) a serine (S) an alanine (A) or isoleucine (I) is present at a position corresponding to 336; and/or
(iv) a glycine (G), leucine (L), valine (V), alanine (A), methionine (M) or serine (S) is present at a position corresponding to 403,
said positions being defined with reference to SEQ ID NO: 1 or SEQ ID NO: 3.

Any combination of two, three or four of the above defined substitutions may be used to define a KAH of the disclosure.

A KAH polypeptide of the disclosure may preferably be one wherein:
a methionine (M) or valine (V) is present at a position corresponding to 136;
(ii) an asparagine (N) is present at a position corresponding 248;
(iii) a serine (S) is present at a position corresponding to 336; and/or
(iv) a glycine (G) is present at a position corresponding to 403,
said positions being defined with reference to SEQ ID NO: 1 or SEQ ID NO: 3.

Any combination of the above defined substitutions may be used to define a KAH of the disclosure.

Thus, a KAH polypeptide of the disclosure may comprise an amino acid sequence which, when aligned with the KAH comprising the sequence set out in SEQ ID NO: 1 or SEQ ID NO: 3, comprises at least the following substitutions of an amino acid corresponding to any of amino acids:
136 and 248
136 and 336
136 and 403
248 and 336
248 and 403
336 and 403
136, 248 and 403
136, 336 and 403
136, 248 and 336
248, 336 and 403 or
136, 248, 336 and 403,
said positions being defined with reference to SEQ ID NO: 1 or SEQ ID NO: 3.

Thus, a KAH polypeptide of the disclosure may comprise an amino acid sequence which, when aligned with the KAH comprising the sequence set out in SEQ ID NO: 1 or SEQ ID NO: 3, comprises at least the following substitutions of an amino acid corresponding to any of amino acids:
a) a methionine (M), or valine (V), or alanine (A), or phenylalanine (F), or tryptophan (W), or glutamine (Q), or histidine (H) or a threonine (T) present at a position corresponding to position 136 and an asparagine (N), or glutamine (Q), or threonine (T), or glycine (G), or alanine (A), or isoleucine (I), or valine (V), or phenylalanine (F) or proline (P) present at a position corresponding position 248;
b) a methionine (M), or valine (V), or alanine (A), phenylalanine (F), or tryptophan (W), or glutamine (Q), or histidine (H) or a threonine (T) is present at a position corresponding to 136 and a serine (S), or an alanine (A), or isoleucine (I) is present at a position corresponding to position 336;
c) a methionine (M), or valine (V), or alanine (A), phenylalanine (F), or tryptophan (W), or glutamine (Q), or histidine (H) or a threonine (T) is present at a position corresponding to 136 and a glycine (G), or leucine (L), or valine (V), or alanine (A), or methionine (M) or serine (S) is present at a position corresponding to position 403;
d) an asparagine (N), or glutamine (Q), or threonine (T), or glycine (G), or alanine (A), or isoleucine (I), or valine (V), or phenylalanine (F) or proline (P) present at a position corresponding position 248 and a serine (S), or an alanine (A), or isoleucine (I) is present at a position corresponding to position 336;

e) an asparagine (N), or glutamine (Q), or threonine (T), or glycine (G), or alanine (A), or isoleucine (I), or valine (V), or phenylalanine (F) or proline (P) present at a position corresponding position 248 and a glycine (G), or leucine (L), or valine (V), or alanine (A), or methionine (M) or serine (S) is present at a position corresponding to position 403;
f) a serine (S), or an alanine (A), or isoleucine (I) is present at a position corresponding to position 336 and a glycine (G), or leucine (L), or valine (V), or alanine (A), or methionine (M) or serine (S) is present at a position corresponding to position 403;
g) a methionine (M), or valine (V), or alanine (A), phenylalanine (F), or tryptophan (W), or glutamine (Q), or histidine (H) or a threonine (T) is present at a position corresponding to 136, an asparagine (N), or glutamine (Q), or threonine (T), or glycine (G), or alanine (A), or isoleucine (I), or valine (V), or phenylalanine (F) or proline (P) present at a position corresponding position 248 and a glycine (G), or leucine (L), or valine (V), or alanine (A), or methionine (M) or serine (S) is present at a position corresponding to position 403;
h) a methionine (M), or valine (V), or alanine (A), phenylalanine (F), or tryptophan (W), or glutamine (Q), or histidine (H) or a threonine (T) is present at a position corresponding to 136, a serine (S), or an alanine (A), or isoleucine (I) is present at a position corresponding to position 336 and a glycine (G), or leucine (L), or valine (V), or alanine (A), or methionine (M) or serine (S) is present at a position corresponding to position 403;
i) a methionine (M), or valine (V), or alanine (A), phenylalanine (F), or tryptophan (W), or glutamine (Q), or histidine (H) or a threonine (T) is present at a position corresponding to 136, an asparagine (N), or glutamine (Q), or threonine (T), or glycine (G), or alanine (A), or isoleucine (I), or valine (V), or phenylalanine (F) or proline (P) present at a position corresponding position 248 and a serine (S), or an alanine (A), or isoleucine (I) is present at a position corresponding to position 336;
j) an asparagine (N), or glutamine (Q), or threonine (T), or glycine (G), or alanine (A), or isoleucine (I), or valine (V), or phenylalanine (F) or proline (P) present at a position corresponding position 248, a serine (S), or an alanine (A), or isoleucine (I) is present at a position corresponding to position 336 and a glycine (G), or leucine (L), or valine (V), or alanine (A), or methionine (M) or serine (S) is present at a position corresponding to position 403 or
k) a methionine (M), or valine (V), or alanine (A), phenylalanine (F), or tryptophan (W), or glutamine (Q), or histidine (H) or a threonine (T) is present at a position corresponding to 136, an asparagine (N), or glutamine (Q), or threonine (T), or glycine (G), or alanine (A), or isoleucine (I), or valine (V), or phenylalanine (F) or proline (P) present at a position corresponding position 248, a serine (S), or an alanine (A), or isoleucine (I) is present at a position corresponding to position 336 and a glycine (G), or leucine (L), or valine (V), or alanine (A), or methionine (M) or serine (S) is present at a position corresponding to position 403,
said positions being defined with reference to SEQ ID NO: 1 or SEQ ID NO: 3.

A KAH polypeptide of the disclosure may comprise additional substitutions positions other than one or more of the five substitutions positions defined above, for example, one or more additional substitutions, additions or deletions.

A KAH of the disclosure may comprise a combination of different types of modification of this sort. A KAH may comprise one, two, three, four, at least 5, at least 10, at least 15, at least 20, at least 25, at least 30 or more such modifications (which may all be of the same type or may be different types of modification). Typically, the additional modifications may be substitutions.

A KAH polypeptide of the disclosure may comprise the amino acid sequence set out in SEQ ID NO: 3. However, a KAH polypeptide may comprise any combination of substitutions at positions 136, 248, 336 or 403, said positions being defined with reference to a suitable reference sequence such as that set out in SEQ ID NO: 1 or SEQ ID NO: 3.

A host cell may comprise nucleic acids encoding one, two, three, four, five or more KAHs of the disclosure. Such KAH polypeptides may be the same or different. A host cell may comprise a nucleic acid encoding the KAH of SEQ ID NO: 1 or SEQ ID NO: 3 and a nucleic acid encoding one or more KAHs of the disclosure. That is to say, a host may comprise a nucleic acid encoding the KAH of SEQ ID NO: 1 or SEQ ID NO: 3 and a nucleic acid encoding one or more KAHs of the disclosure, each of which may be present in a copy of one, two, three, four, five or more.

A KAH polypeptide will typically have modified KAH activity in comparison to a reference polypeptide. Typically, the modified activity may be defined in terms of steviol and/or steviol glycoside production in a recombinant host.

The modified activity may be defined in terms of an increase in the production of steviol and/or a steviol glycoside when a KAH is overexpressed in a host cell as compared to the production level of an equivalent host cell which overexpresses a reference polypeptide, for example that of SEQ ID NO: 1 or SEQ ID NO: 3.

The modified activity may be defined in terms of a decrease in the production of a non-steviol glycoside, such as a non-desirable product such as a kaurenoic acid glycoside, when a KAH is overexpressed in a host cell as compared to the production level of an equivalent host cell which overexpresses a reference polypeptide, for example that of SEQ ID NO: 1 or SEQ ID NO: 3.

The modified activity may be defined in terms of a change in ratio of the production of two steviol glycosides, for example the ratio of rebaudioside A: rebaudioside M may be increased or, alternatively, the ratio of rebaudioside M: rebaudioside A may be increased, when a KAH is overexpressed in a host cell as compared to the production level of an equivalent host cell which overexpresses a reference polypeptide, for example that of SEQ ID NO: 1 or SEQ ID NO: 3.

The modified activity may be defined in terms of a change in ratio of the sum of steviol glycosides produced to the sum of kaurenoic acid-glycosides, for example the ratio of the sum of steviol glycosides: the sum of kaurenoic acid-glycosides may be increased when a KAH is overexpressed in a host cell as compared to the production level of an equivalent host cell which overexpresses a reference polypeptide, for example that of SEQ ID NO: 1 or SEQ ID NO: 3.

The modified activity may also be defined in terms of increased stability of a KAH, for example having a longer half-life than a reference polypeptide, for example that of SEQ ID NO: 1 or SEQ ID NO: 3.

The modified activity may also be defined in terms of more efficient electron transport, for example in terms of less decoupling, in comparison to a reference polypeptide, for example that of SEQ ID NO: 1 or SEQ ID NO: 3.

The modified activity may also be defined in terms of more efficient electron localization within a host cell in comparison to a reference polypeptide, for example that of SEQ ID NO: 1 or SEQ ID NO: 3.

A KAH may be capable of increasing production levels, for example by at least 5%, at least 10%, at least 25%, at least 50%, at least 100% or more. Production levels may be expressed in terms of g/L or mol/L (M), so an increase in the production level of steviol and/or steviol glycosides will be evident by higher level of production in terms of g/L or mol/L.

In the case of a non-desirable product, such as one or more kaurenoic acid glycosides, a KAH may be capable of decreasing production levels for example by at least 5%, at least 10%, at least 25%, at least 50% or more. A KAH may be capable of increasing this ratio, for example by at least 1%, at least 2%, at least 5%, at least 10%, at least 25%, at least 50%, at least 100% or more.

As set out above, this may also be defined in terms of an increase the sum of steviol glycosides: the sum of kaurenoic acid-glycosides.

The word "polypeptide" is used herein for chains containing more than about seven amino acid residues. All polypeptide sequences herein are written from left to right and in the direction from amino terminus to carboxy terminus. The one-letter code of amino acids used herein is commonly known in the art and can be found in Sambrook, et al. (Molecular Cloning: A Laboratory Manual, 2nd ed. Cold Spring Harbor Laboratory, Cold Spring Harbor Laboratory Press, Cold Spring Harbor, N.Y., 1989).

A KAH polypeptide of the disclosure may be in isolated form, such as substantially isolated form. By "isolated" polypeptide or protein is intended a polypeptide or protein removed from its native environment. For example, recombinantly produced polypeptides and proteins expressed in host cells are considered isolated for the purpose of the disclosure as are recombinant polypeptides which have been substantially purified by any suitable technique. A KAH polypeptide according to the disclosure can be recovered and purified from recombinant cell cultures by methods known in the art.

KAH polypeptides of the present disclosure include products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present disclosure may be glycosylated or may be non-glycosylated. In addition, polypeptides of the disclosure may also include an initial modified methionine residue, in some cases as a result of host-mediated processes.

The disclosure also features biologically active fragments of the KAH polypeptides according to the disclosure. Such fragments are considered to be encompassed within the term "a KAH of the disclosure".

Biologically active fragments of a KAH polypeptide of the disclosure include polypeptides comprising amino acid sequences sufficiently identical to or derived from the amino acid sequence of a KAH protein of the disclosure which include fewer amino acids than the full length protein but which exhibit at least one biological activity of the corresponding full-length protein. Typically, biologically active fragments comprise a domain or motif with at least one activity of a KAH protein of the disclosure. A biologically active fragment of a KAH of the disclosure can be a polypeptide which is, for example, 10, 25, 50, 100 or more amino acids in length. Moreover, other biologically active portions, in which other regions of the protein are deleted, can be prepared by recombinant techniques and evaluated for one or more of the biological activities of the native form of a polypeptide of the disclosure.

Typically, a protein fragment of a KAH of the disclosure will comprise one or more of the substitutions defined herein.

The disclosure also features nucleic acid fragments which encode the above biologically active fragments (which biologically active fragments are themselves KAHs of the disclosure).

The present disclosure provides polynucleotides which comprise sequence encoding a KAH polypeptide of the disclosure (and biologically active fragments thereof). The disclosure also relates to an isolated polynucleotide encoding at least one functional domain of a KAH polypeptide KAH of the disclosure. Typically, such a domain will comprise one or more of the substitutions described herein.

A nucleic acid molecule of the present disclosure can be generated using standard molecular biology techniques well known to those skilled in the art taken in combination with the sequence information provided herein. For example, using standard synthetic techniques, the required nucleic acid molecule may be generated by PCR or synthesized de novo. Such a synthetic process will typically be an automated process.

A nucleic acid of the disclosure may comprise one or more deletions, i.e. gaps, in comparison to a nucleic acid encoding a reference KAH. Such deletions/gaps may also be generated using site-directed mutagenesis using appropriate oligonucleotides. Techniques for generating such deletions are well known to those skilled in the art.

Furthermore, oligonucleotides corresponding to or hybridizable to nucleotide sequences according to the disclosure can be prepared by standard synthetic techniques, e.g., using an automated DNA synthesizer.

Also, complementary nucleic acids and antisense nucleic acids are included in the present disclosure. A nucleic acid molecule which is complementary to another nucleotide sequence is one which is sufficiently complementary to the other nucleotide sequence such that it can hybridize to the other nucleotide sequence thereby forming a stable duplex.

One aspect of the disclosure pertains to isolated nucleic acid molecules that encode a KAH polypeptide of the disclosure, or a biologically active fragment or domain thereof, as well as nucleic acid molecules sufficient for use as hybridization probes to identify nucleic acid molecules encoding a polypeptide of the disclosure and fragments of such nucleic acid molecules suitable for use as PCR primers for the amplification or mutation of nucleic acid molecules, such as for the preparation of nucleic acid molecules of the disclosure.

An "isolated nucleic acid" or "isolated polynucleotide" is a DNA or RNA that is not immediately contiguous with both of the coding sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promotor) sequences that are immediately contiguous to the coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide that is substantially free of cellular material, viral material, or culture medium (when produced by recombinant DNA techniques), or chemical precursors or other chemicals (when chemically synthesized). Moreover, an "isolated nucleic acid fragment" is a nucleic acid fragment that is not naturally occurring as a fragment and would not be found in the natural state.

As used herein, the terms "nucleic acid", "polynucleotide" or "nucleic acid molecule" are intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. The nucleic acid may be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

The disclosure also relates to a nucleic acid construct comprising a nucleic acid sequence encoding a KAH polypeptide of the disclosure and, linked operably thereto, control sequences permitting expression of the nucleic acid sequence in a host cell. The nucleic acid construct may be incorporated into a vector, such as an expression vector and/or into a host cell in order to effect expression of the KAH polypeptide.

The term "nucleic acid construct" is herein referred to as a nucleic acid molecule, either single-or double-stranded, which is isolated from a naturally-occurring gene or, more typically, which has been modified to contain segments of nucleic acid which are combined and juxtaposed in a manner which would not otherwise exist in nature. The term nucleic acid construct is synonymous with the term "expression cassette" when the nucleic acid construct contains all the control sequences required for expression of a coding sequence, wherein said control sequences are operably linked to said coding sequence.

As used herein, the term "operably linked" refers to a linkage of polynucleotide elements (or coding sequences or nucleic acid sequence) in a functional relationship. A nucleic acid sequence is "operably linked" when it is placed into a functional relationship with another nucleic acid sequence. For instance, a promoter or enhancer is operably linked to a coding sequence if it affects the transcription of the coding sequence.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences known to one of skilled in the art. A "constitutive" promoter is a promoter that is active under most environmental and developmental conditions. An "inducible" promoter is a promoter that is active under environmental or developmental regulation.

A promoter that could be used to achieve the expression of a nucleotide sequence coding for an enzyme such as a KAH polypeptide or any other enzyme introduced in recombinant host of the disclosure, may be not native to a nucleotide sequence coding for the enzyme to be expressed, i.e. a promoter that is heterologous to the nucleotide sequence (coding sequence) to which it is operably linked. Preferably, the promoter is homologous, i.e. endogenous to the host cell.

Suitable promoters in this context include both constitutive and inducible natural promoters as well as engineered promoters, which are well known to the person skilled in the art. Suitable promoters in host cells may be GAL7, GAL10, or GAL 1, CYC1, HIS3, ADH1, PGL, PH05, GAPDH, ADC1, TRP1, URA3, LEU2, ENO, TPI, and AOX1. Other suitable promoters include PDC, GPD1, PGK1, TEF1, and TDH.

Usually a nucleotide sequence encoding an enzyme comprises a terminator. Any terminator, which is functional in a host cell, may be used in the present disclosure. Preferred terminators are obtained from natural genes of the host cell. Suitable terminator sequences are well known in the art. Preferably, such terminators are combined with mutations that prevent nonsense mediated mRNA decay in the host cell of the disclosure (see for example: Shirley et al., 2002, Genetics 161:1465-1482).

The disclosure further relates to a vector, preferably an expression vector, comprising a nucleic acid or a nucleic acid construct of the disclosure of the disclosure (i.e. comprising sequence encoding a KAH polypeptide of the disclosure).

In order to facilitate expression and/or translation of the KAH, the nucleic acid sequence encoding the KAH may be comprised in an expression vector such that the gene encoding the KAH is operably linked to the appropriate control sequences for expression and/or translation in vitro, or in a host cell of the disclosure. That is to say, the disclosure provides an expression vector comprising a nucleic acid or nucleic acid construct of the disclosure.

The expression vector may be any vector (e.g., a plasmid or virus), which can be conveniently subjected to recombinant DNA procedures and can bring about the expression of the polynucleotide encoding the KAH polypeptide. The choice of the vector will typically depend on the compatibility of the vector with the cell into which the vector is to be introduced. The vectors may be linear or closed circular plasmids. The vector may be an autonomously replicating vector, i. e., a vector, which exists as an extra-chromosomal entity, the replication of which is independent of chromosomal replication, e.g., a plasmid, an extra-chromosomal element, a mini-chromosome, or an artificial chromosome. If intended for use in a host cell of fungal origin, a suitable episomal nucleic acid construct may e.g. be based on the yeast 2μ or pKD1 plasmids (Gleer et al., 1991, Biotechnology 9: 968-975), or the AMA plasmids (Fierro et al., 1995, Curr Genet. 29:482-489).

Alternatively, the expression vector may be one which, when introduced into the host cell, is integrated into the genome and replicated together with the chromosome(s) into which it has been integrated. The integrative cloning vector may integrate at random or at a predetermined target locus in the chromosomes of the host cell. In a preferred embodiment of the disclosure, the integrative cloning vector comprises a DNA fragment, which is homologous to a DNA sequence in a predetermined target locus in the genome of host cell for targeting the integration of the cloning vector to this predetermined locus. In order to promote targeted integration, the cloning vector is preferably linearized prior to transformation of the cell. Linearization is preferably performed such that at least one but preferably either end of the cloning vector is flanked by sequences homologous to the target locus. The length of the homologous sequences flanking the target locus is preferably at least 20 bp, at least 30 bp, at least 50 bp, at least 0.1 kb, at least 0.2 kb, at least 0.5 kb, at least 1 kb, at least 2 kb or longer. The efficiency of targeted integration into the genome of the host cell, i.e.

integration in a predetermined target locus, is increased by augmented homologous recombination abilities of the host cell.

The homologous flanking DNA sequences in the cloning vector, which are homologous to the target locus, may be derived from a highly expressed locus meaning that they are derived from a gene, which is capable of high expression level in the host cell. A gene capable of high expression level, i.e. a highly expressed gene, is herein defined as a gene whose mRNA can make up at least 0.5% (w/w) of the total cellular mRNA, e.g. under induced conditions, or alternatively, a gene whose gene product can make up at least 1% (w/w) of the total cellular protein, or, in case of a secreted gene product, can be secreted to a level of at least 0.1 g/l. More typically, the target locus may be an intergenic location, so that a gene is not interrupted. Such a locus may also provide for high expression levels. Accordingly, the homologous flanking DNA sequences in the cloning vector may be homologous to an intergenic target locus A nucleic acid construct or expression vector may be assembled in vivo in a host cell of the disclosure and, optionally, integrated into the genome of the cell in a single step (see, for example, WO2013/076280)

More than one copy of a nucleic acid construct or expression vector of the disclosure may be inserted into a host cell to increase production of the KAH polypeptide (over-expression) encoded by the nucleic acid sequence comprised within the nucleic acid construct. This can be done, preferably by integrating into its genome two or more copies of the nucleic acid, more preferably by targeting the integration of the nucleic acid to a locus defined as defined above.

It will be appreciated by those skilled in the art that the design of the expression vector can depend on such factors as the choice of the host cell to be transformed, the level of expression of protein desired, etc. The expression vectors of the disclosure can be introduced into host cells to thereby produce proteins or peptides, encoded by nucleic acids as described herein (e.g. a KAH of SEQ ID NO: 1 or SEQ ID NO: 3, for example a functional equivalent or fragment, or a fusion protein comprising one or more of such KAHs).

The nucleic acid constructs and vectors of the disclosure can be designed for expression of KAH polypeptides of the disclosure in a prokaryotic host cell or eukaryotic host cell.

A nucleic acid construct and/or expression vector of the disclosure can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell well known to those skilled in the art. Suitable methods for transforming or transfecting host cells can be found in Sambrook, et al. (Molecular Cloning: A Laboratory Manual, 2nd, ed. Cold Spring Harbor Laboratory, Cold Spring Harbor Laboratory Press, Cold Spring Harbor, N.Y., 1989), Davis et al., Basic Methods in Molecular Biology (1986) and other laboratory manuals.

"Functional equivalents" according to the disclosure are isolated nucleic acid fragments that encode a polypeptide that exhibits a particular function of a KAH of the disclosure as defined herein. Functional equivalents therefore also encompass biologically active fragments and are themselves encompassed within the term "a KAH" (or the like) of the disclosure.

Preferably, a functional equivalent of the disclosure comprises one or more of the substitutions described herein. However, a functional equivalent may comprise one or more modifications in addition to the substitutions described above.

Functional nucleic acid equivalents may typically contain silent mutations or mutations that do not alter the biological function of the encoded KAH polypeptide. Accordingly, the disclosure provides nucleic acid molecules encoding a KAH protein that contains changes in amino acid residues that are not essential for a particular biological activity, i.e. KAH activity.

Such functional equivalents of KAH proteins differ in amino acid sequence from the parent KAH sequence from which they are derived yet retain at least one biological activity thereof, preferably they retain at least KAH activity. The skilled person will recognise that changes can be introduced by mutation into the nucleotide sequences according to the disclosure thereby leading to changes in the amino acid sequence of the resulting protein without substantially altering the function of such a protein.

In one embodiment the isolated nucleic acid molecule comprises a nucleotide sequence encoding a protein, wherein the protein comprises an amino acid sequence having at least about 60%, 65%, 70%, 75%, 80%, 85%, 90%, 95%, 96%, 97%, 98%, 99% identity with the parent KAH or to the reference amino acid sequence (for example that shown in SEQ ID NO: 1 or SEQ ID NO: 3).

Accordingly, a functional equivalent of a KAH of the disclosure is preferably a protein which comprises an amino acid sequence having at least about 60%, 65%, 70%, 75%, 80%, 85%, 90%, 95%, 96%, 97%, 98%, 99% or more identity to the parent KAH amino acid sequence or reference polypeptide sequence, for example that shown in SEQ ID NO: 1 or SEQ ID NO: 3, and typically also retains at least one functional activity of the parent KAH polypeptide.

A polypeptide of the disclosure having kaurenoic acid 13-hydroxylase activity may comprise an amino acid sequence having at least about 80% sequence identity, at least about 90% sequence identity, at least about 95% sequence identity, at least about 96%, at least about 97%, at least about 98% or at least about 99% sequence identity to any one of SEQ ID NO: 5, SEQ ID NO: 7, SEQ ID NO: 9, SEQ ID NO: 11 or SEQ ID NO: 13.

A KAH polypeptide of the disclosure may have a sequence as defined in Table 1 or a substitution pattern as defined in Table 1 (in terms of position(s), if not precisely the same amino acid substitution).

KAH polypeptides of the disclosure may be identified e.g. by screening libraries of mutants, e.g. substitution mutants, of a suitable reference polypeptide. Candidate mutants may be screened on the basis of their ability to increase steviol or steviol glycoside production, when expressed in a host cell (in comparison with a corresponding host cell expressing the reference polypeptide).

Fragments of a nucleic acid according to the disclosure may comprise or consist of sequences not encoding functional polypeptides. Such nucleic acids may function as probes or primers for a PCR reaction.

Nucleic acids according to the disclosure irrespective of whether they encode functional or non-functional polypeptides can be used as hybridization probes or polymerase chain reaction (PCR) primers. Uses of the nucleic acid molecules of the present disclosure that do not encode a polypeptide having KAH activity include, inter alia, (1) in situ hybridization (e.g. FISH) to metaphase chromosomal spreads to provide precise chromosomal location of an KAH-encoding gene as described in Verma et al., Human Chromosomes: a Manual of Basic Techniques, Pergamon Press, New York (1988); (2) Northern blot analysis for detecting expression of KAH mRNA in specific tissues and/or cells; and (3) probes and primers that can be used as a diagnostic tool to analyse the presence of a nucleic acid hybridizable to such a probe or primer in a given biological (e.g. tissue) sample.

A KAH of the disclosure based on a given reference KAH enzyme can be obtained by the following standard procedure:

Mutagenesis (error-prone, doped oligo, spiked oligo) or synthesis of variants

Transformation in, for example, *Y. lipolytica* or *S. cerevisiae*

Cultivation of transformants, selection of transformants

Expression in, for example, *Y. lipolytica* or *S. cerevisiae*

Primary Screening, for example on the basis of steviol or steviol glycoside production Identification of an improved KAH In one embodiment, the disclosure relates to a method of producing a KAH polypeptide according to the disclosure, which method comprises:

a) selecting a reference KAH polypeptide (i.e. a template or starting polypeptide);
b) substituting at least one amino acid residue corresponding to any of
136, 248, 336 or 403
said positions being defined with reference to SEQ ID NO: 1 or SEQ ID NO: 3;
c) optionally substituting one or more further amino acids as defined in b);
d) preparing the KAH resulting from steps a)-c);
e) determining a property of the KAH, for example as set out in the Examples; and
f) selecting a KAH with an altered property in comparison to the reference KAH polypeptide.

In a preferred embodiment in the method of producing a KAH polypeptide according to the disclosure, the reference KAH polypeptide has the sequence set out in SEQ ID NO: 1 or SEQ ID NO: 3.

More preferably in step b) of the method according to the disclosure at least one amino acid residue corresponding to any of
136, 248, 336 or 403
is substituted, said positions being defined with reference to SEQ ID NO: 1 or SEQ ID NO: 3. The reference polypeptide may have at least about 80% homology with SEQ ID NO: 1 or SEQ ID NO: 3.

In another embodiment, the disclosure features host cells, e.g., transformed host cells or recombinant host cells that contain a nucleic acid, nucleic acid construct or vector of the disclosure. A "host cell" or "recombinant cell" according to the disclosure is typically a cell into which (or into an ancestor of which) has been introduced, by means of recombinant DNA techniques, a nucleic acid according to the disclosure, i.e. a nucleic acid encoding a KAH of the disclosure. In the context of the present disclosure a "host cell" according to the disclosure or a parent of said host cell may be any type of host cell.

Thus, a host cell of the disclosure may comprise a recombinant nucleic acid encoding one or more KAH polypeptides of the disclosure.

A host cell according to any one of the preceding claims wherein the host cell is a eukaryotic or a prokaryotic cell. Accordingly, both prokaryotic and eukaryotic cells are included, e.g., bacteria, fungi, yeast, and the like, especially preferred are cells from yeasts, for example, *S. cerevisiae, Y. lipolytica* and *K. lactis*. Host cells also include, but are not limited to, mammalian cell lines such as CHO, VERO, BHK, HeLa, COS, MDCK, 293, 3T3, WI38, and choroid plexus cell lines.

The disclosure thus provides a method for producing a KAH, which method comprises cultivating a host cell as described herein under conditions suitable for production of the KAH and, optionally, recovering the KAH. Typically the host cell is capable of producing steviol or a steviol glycoside.

A recombinant host of the disclosure may comprise any polypeptide as described herein. Typically, a recombinant host of the disclosure is capable of producing a steviol glycoside. Typically, a recombinant host of the disclosure is capable of producing a glycosylated diterpene, such as a steviol glycoside. For example, a recombinant host of the disclosure may be capable of producing one or more of, for example, steviol-13-monoside, steviol-19-monoside, 13-[(β-D-Glucopyranosyl)oxy]kaur-16-en-18-oic acid 2-O-β-D-glucopyranosyl-β-D-glucopyranosyl ester, rubusoside, stevioside, steviol-19-diside, steviolbioside, rebaudiosideA, rebaudiosideE, rebaudiosideD or rebaudiosideM.

A recombinant host of the disclosure may comprise one or more recombinant nucleic acid sequences encoding one or more polypeptides having UDP-glycosyltransferase (UGT) activity.

For the purposes of this disclosure, a polypeptide having UGT activity is one which has glycosyltransferase activity (EC 2.4), i.e. that can act as a catalyst for the transfer of a monosaccharide unit from an activated nucleotide sugar (also known as the "glycosyl donor") to a glycosyl acceptor molecule, usually an alcohol. The glycosyl donor for a UGT is typically the nucleotide sugar uridine diphosphate glucose (uracil-diphosphate glucose, UDP-glucose).

Such additional UGTs may be selected so as to produce a desired steviol glycoside. Schematic diagrams of steviol glycoside formation are set out in Humphrey et al., Plant Molecular Biology (2006) 61: 47-62 and Mohamed et al., J. Plant Physiology 168 (2011) 1136-1141. In addition, FIG. 1 sets out a schematic diagram of steviol glycoside formation.

A recombinant host of the disclosure may thus comprise one or more recombinant nucleic acid sequences encoding one or more of:

(i) a polypeptide having UGT74G1 activity;
(ii) a polypeptide having UGT2 activity;
(ii) a polypeptide having UGT85C2 activity; and
(iii) a polypeptide having UGT76G1 activity.

A recombinant yeast suitable for use in the disclosure may comprise a nucleotide sequence encoding a polypeptide capable of catalyzing the addition of a C-13-glucose to steviol. That is to say, a recombinant yeast suitable for use in a method of the disclosure may comprise a UGT which is capable of catalyzing a reaction in which steviol is converted to steviolmonoside.

Such a recombinant yeast suitable for use in a method of the disclosure may comprise a nucleotide sequence encoding a polypeptide having the activity shown by UDP-glycosyltransferase (UGT) UGT85C2, whereby the nucleotide sequence upon transformation of the yeast confers on that yeast the ability to convert steviol to steviolmonoside.

UGT85C2 activity is transfer of a glucose unit to the 13-OH of steviol. Thus, a suitable UGT85C2 may function as a uridine 5'-diphospho glucosyl: steviol 13-OH transferase, and a uridine 5'-diphospho glucosyl: steviol-19-0-glucoside 13-OH transferase. A functional UGT85C2 polypeptides may also catalyze glucosyl transferase reactions that utilize steviol glycoside substrates other than steviol and steviol-19-O-glucoside. Such sequences may be referred to as UGT1 sequences herein.

A recombinant yeast suitable for use in the disclosure may comprise a nucleotide sequence encoding a polypeptide which has UGT2 activity.

A polypeptide having UGT2 activity is one which functions as a uridine 5'-diphospho glucosyl: steviol-13-O-glucoside transferase (also referred to as a steviol-13-monoglucoside 1,2-glucosylase), transferring a glucose moiety to the C-2' of the 13-O-glucose of the acceptor molecule, steviol-13-O-glucoside. Typically, a suitable UGT2 polypeptide also functions as a uridine 5'-diphospho glucosyl: rubusoside transferase transferring a glucose moiety to the C-2' of the 13-O-glucose of the acceptor molecule, rubusoside.

A polypeptide having UGT2 activity may also catalyze reactions that utilize steviol glycoside substrates other than steviol-13-O-glucoside and rubusoside, e.g., functional UGT2 polypeptides may utilize stevioside as a substrate, transferring a glucose moiety to the C-2' of the 19-O-glucose residue to produce rebaudioside E. A functional UGT2 polypeptides may also utilize rebaudioside A as a substrate, transferring a glucose moiety to the C-2' of the 19-O-glucose residue to produce rebaudioside D. However, a functional UGT2 polypeptide typically does not transfer a glucose moiety to steviol compounds having a 1,3-bound glucose at the C-13 position, i.e., transfer of a glucose moiety to steviol 1,3-bioside and 1,3-stevioside typically does not occur.

A polypeptide having UGT2 activity may also transfer sugar moieties from donors other than uridine diphosphate glucose. For example, a polypeptide having UGT2 activity act as a uridine 5'-diphospho D-xylosyl: steviol-13-O-glucoside transferase, transferring a xylose moiety to the C-2' of the 13-O-glucose of the acceptor molecule, steviol-13-O-glucoside. As another example, a polypeptide having UGT2 activity may act as a uridine 5'-diphospho L-rhamnosyl: steviol-13-O-glucoside transferase, transferring a rhamnose moiety to the C-2' of the 13-O-glucose of the acceptor molecule, steviol.

A recombinant yeast suitable for use in the method of the disclosure may comprise a nucleotide sequence encoding a polypeptide having UGT activity may comprise a nucleotide sequence encoding a polypeptide capable of catalyzing the addition of a C-19-glucose to steviolbioside. That is to say, a recombinant yeast of the disclosure may comprise a UGT which is capable of catalyzing a reaction in which steviolbioside is converted to stevioside. Accordingly, such a recombinant yeast may be capable of converting steviolbioside to stevioside. Expression of such a nucleotide sequence may confer on the recombinant yeast the ability to produce at least stevioside.

A recombinant yeast suitable for use in a method of the disclosure may thus also comprise a nucleotide sequence encoding a polypeptide having the activity shown by UDP-glycosyltransferase (UGT) UGT74G1, whereby the nucleotide sequence upon transformation of the yeast confers on the cell the ability to convert steviolbioside to stevioside.

Suitable UGT74G1 polypeptides may be capable of transferring a glucose unit to the 13-OH or the 19-COOH of steviol. A suitable UGT74G1 polypeptide may function as a uridine 5'-diphospho glucosyl: steviol 19-COOH transferase and a uridine 5'-diphospho glucosyl: steviol-13-O-glucoside 19-COOH transferase. Functional UGT74G1 polypeptides also may catalyze glycosyl transferase reactions that utilize steviol glycoside substrates other than steviol and steviol-13-O-glucoside, or that transfer sugar moieties from donors other than uridine diphosphate glucose. Such sequences may be referred to herein as UGT3 sequences.

A recombinant yeast suitable for use in a method the disclosure may comprise a nucleotide sequence encoding a polypeptide capable of catalyzing glucosylation of the C-3' of the glucose at the C-13 position of stevioside. That is to say, a recombinant yeast suitable for use in a method of the disclosure may comprise a UGT which is capable of catalyzing a reaction in which stevioside is converted to rebaudioside A. Accordingly, such a recombinant yeast may be capable of converting stevioside to rebaudioside A. Expression of such a nucleotide sequence may confer on the yeast the ability to produce at least rebaudioside A.

A recombinant yeast suitable for use in a method of the disclosure may thus also comprise a nucleotide sequence encoding a polypeptide having the activity shown by UDP-glycosyltransferase (UGT) UGT76G1, whereby the nucleotide sequence upon transformation of a yeast confers on that yeast the ability to convert stevioside to rebaudioside A.

A suitable UGT76G1 adds a glucose moiety to the C-3' of the C-13-O-glucose of the acceptor molecule, a steviol 1,2 glycoside. Thus, UGT76G1 functions, for example, as a uridine 5'-diphospho glucosyl: steviol 13-0-1,2 glucoside C-3 ' glucosyl transferase and a uridine 5'-diphospho glucosyl: steviol-19-0-glucose, 13-0-1,2 bioside C-3' glucosyl transferase. Functional UGT76G1 polypeptides may also catalyze glucosyl transferase reactions that utilize steviol glycoside substrates that contain sugars other than glucose, e.g., steviol rhamnosides and steviol xylosides. Such sequences may be referred to herein as UGT4 sequences. A UGT4 may alternatively or in addition be capable of converting RebD to RebM.

A recombinant yeast suitable for use in a method of the disclosure typically comprises nucleotide sequences encoding at least one polypeptide having UGT1 activity, at least one polypeptide having UGT2 activity, at least one polypeptide having UGT3 activity and at least one polypeptide having UGT4 activity. One or more of these nucleic acid sequences may be recombinant. A given nucleic acid may encode a polypeptide having one or more of the above activities. For example, a nucleic acid may encode a polypeptide which has two, three or four of the activities set out above. Preferably, a recombinant yeast for use in the method of the disclosure comprises UGT1, UGT2 and UGT3 and UGT4 activity. Suitable UGT1, UGT2, UGT3 and UGT4 sequences are described in Table 1 of WO2015/007748.

A recombinant host of the disclosure may comprise two or more nucleic acid sequences encoding a polypeptide having any one UGT activity, for example UGT1, 2, 3 or 4, activity. Where a recombinant host of the disclosure comprises two or more nucleic acid sequence encoding a polypeptide having any one UGT activity, those nucleic acid sequences may be the same or different and/or may encode the same or different polypeptides. In particular, a recombinant host of the disclosure may comprise a nucleic acid sequence encoding a two different UGT2 polypeptides.

A recombinant host according to the disclosure may comprise one or more recombinant nucleotide sequence(s) encoding one of more of:
a polypeptide having ent-copalyl pyrophosphate synthase activity;
a polypeptide having ent-Kaurene synthase activity; and
a polypeptide having ent-Kaurene oxidase activity.

A recombinant host according to the disclosure may comprise a recombinant nucleotide sequence encoding a polypeptide having kaurenoic acid 13-hydroxylase activity, other than a KAH polypeptide of the disclosure. That is to say, a recombinant host of the disclosure may comprise a nucleotide sequence or sequences comprising two or more different polypeptides having kaurenoic acid 13-hydroxylase activity one being a KAH polypeptide of the disclosure. For the purposes of this disclosure, a polypeptide having ent-copalyl pyrophosphate synthase (EC 5.5.1.13) is capable of catalyzing the chemical reaction:

For the purposes of this disclosure, a polypeptide having ent-kaurene oxidase activity (EC 1.14.13.78) is a polypeptide which is capable of catalysing three successive oxidations of the 4-methyl group of ent-kaurene to give kaurenoic acid. Such activity typically requires the presence of a cytochrome P450.

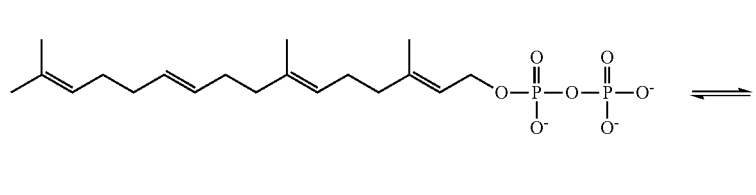 ⇌ 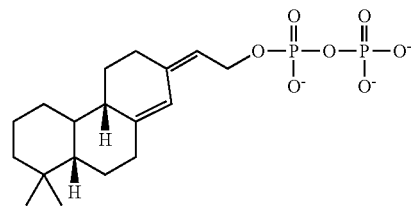

This enzyme has one substrate, geranylgeranyl pyrophosphate, and one product, ent-copalyl pyrophosphate. This enzyme participates in gibberellin biosynthesis. This enzyme belongs to the family of isomerase, specifically the class of intramolecular lyases. The systematic name of this enzyme class is ent-copalyl-diphosphate lyase (decyclizing). Other names in common use include having ent-copalyl pyrophosphate synthase, ent-kaurene synthase A, and ent-kaurene synthetase A.

Suitable nucleic acid sequences encoding an ent-copalyl pyrophosphate synthase may for instance comprise a sequence as set out in SEQ ID. NO: 1, 3, 5, 7, 17, 19, 59, 61, 141, 142, 151, 152, 153, 154, 159, 160, 182 or 184 of WO2015/007748.

For the purposes of this disclosure, a polypeptide having ent-kaurene synthase activity (EC 4.2.3.19) is a polypeptide that is capable of catalyzing the chemical reaction:

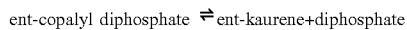
ent-copalyl diphosphate ⇌ ent-kaurene+diphosphate

Hence, this enzyme has one substrate, ent-copalyl diphosphate, and two products, ent-kaurene and diphosphate.

This enzyme belongs to the family of lyases, specifically those carbon-oxygen lyases acting on phosphates. The systematic name of this enzyme class is ent-copalyl-diphosphate diphosphate-lyase (cyclizing, ent-kaurene-forming). Other names in common use include ent-kaurene synthase B, ent-kaurene synthetase B, ent-copalyl-diphosphate diphosphate-lyase, and (cyclizing). This enzyme participates in diterpenoid biosynthesis.

Suitable nucleic acid sequences encoding an ent-Kaurene synthase may for instance comprise a sequence as set out in SEQ ID. NO: 9, 11, 13, 15, 17, 19, 63, 65, 143, 144, 155, 156, 157, 158, 159, 160, 183 or 184 of WO2015/007748.

ent-copalyl diphosphate synthases may also have a distinct ent-kaurene synthase activity associated with the same protein molecule. The reaction catalyzed by ent-kaurene synthase is the next step in the biosynthetic pathway to gibberellins. The two types of enzymic activity are distinct, and site-directed mutagenesis to suppress the ent-kaurene synthase activity of the protein leads to build up of ent-copalyl pyrophosphate.

Accordingly, a single nucleotide sequence used in a recombinant host of the disclosure may encode a polypeptide having ent-copalyl pyrophosphate synthase activity and ent-kaurene synthase activity. Alternatively, the two activities may be encoded two distinct, separate nucleotide sequences.

Suitable nucleic acid sequences encoding an ent-Kaurene oxidase may for instance comprise a sequence as set out in SEQ ID. NO: 21, 23, 25, 67, 85, 145, 161, 162, 163, 180 or 186 of WO2015/007748.

Suitable nucleic acid sequences encoding a kaurenoic acid 13-hydroxylase, other than a KAH polypeptide of the disclosure, may for instance comprise a sequence as set out in SEQ ID. NO: 27, 29, 31, 33, 69, 89, 91, 93, 95, 97, 146, 164, 165, 166, 167 or 185 of WO2015/007748.

A recombinant host of the disclosure may comprise a recombinant nucleic acid sequence encoding a polypeptide having NADPH-cytochrome p450 reductase activity. That is to say, a recombinant host of the disclosure may be capable of expressing a nucleotide sequence encoding a polypeptide having NADPH-cytochrome p450 reductase activity. For the purposes of the disclosure, a polypeptide having NADPH-Cytochrome P450 reductase activity (EC 1.6.2.4;

also known as NADPH:ferrihemoprotein oxidoreductase, NADPH:hemoprotein oxidoreductase, NADPH:P450 oxidoreductase, P450 reductase, POR, CPR, CYPOR) is typically one which is a membrane-bound enzyme allowing electron transfer to cytochrome P450 in the microsome of the host cell from a FAD- and FMN-containing enzyme NADPH:cytochrome P450 reductase (POR; EC 1.6.2.4).

In a recombinant host of the disclosure, the ability of the host to produce geranylgeranyl diphosphate (GGPP) may be upregulated. Upregulated in the context of this disclosure implies that the recombinant host produces more GGPP than an equivalent non-recombinant host.

Accordingly, a recombinant host of the disclosure may comprise one or more nucleotide sequence(s) encoding hydroxymethylglutaryl-CoA reductase, farnesyl-pyrophosphate synthetase and geranylgeranyl diphosphate synthase, whereby the nucleotide sequence(s) upon transformation of the microorganism confer(s) on the microorganism the ability to produce elevated levels of GGPP. Thus, a recombinant host according to the disclosure may comprise one or more recombinant nucleic acid sequence(s) encoding one or more of hydroxymethylglutaryl-CoA reductase, farnesyl-pyrophosphate synthetase and geranylgeranyl diphosphate synthase.

Accordingly, a recombinant host of the disclosure may comprise nucleic acid sequences encoding one or more of:
a polypeptide having hydroxymethylglutaryl-CoA reductase activity;
a polypeptide having farnesyl-pyrophosphate synthetase activity;

a polypeptide having geranylgeranyl diphosphate synthase activity.

A host or host cell as defined herein is an organism suitable for genetic manipulation and one which may be cultured at cell densities useful for industrial production of a target product. A suitable host may be a microorganism, for example one which may be maintained in a fermentation device. A host cell may be a host cell found in nature or a host cell derived from a parent host cell after genetic manipulation or classical mutagenesis.

As used herein, a recombinant host is one which is genetically modified or transformed/transfected with one or more of the nucleotide sequences as defined herein. The presence of the one or more such nucleotide sequences alters the ability of the microorganism to produce steviol or a steviol glycoside, in particular one or more steviol glycosides. A non-recombinant host, i.e. one that is not transformed/transfected or genetically modified, typically does not comprise one or more of the nucleotide sequences enabling the cell to produce a steviol glycoside. Hence, a non-recombinant host is typically a host that does not naturally produce a steviol glycoside, although a host which naturally produces a steviol or a steviol glycoside and which has been modified according to the disclosure (and which thus has an altered ability to produce a steviol glycoside) is considered a recombinant host according to the disclosure.

In particular, it may be possible that the enzymes selected from the group consisting of ent-copalyl pyrophosphate synthase, ent-Kaurene synthase, ent-Kaurene oxidase, and kaurenoic acid 13-hydroxylase, UGTs, hydroxymethylglutaryl-CoA reductase, farnesyl-pyrophosphate synthetase, geranylgeranyl diphosphate synthase and NADPH-cytochrome p450 reductase are native to the host and that transformation with one or more of the nucleotide sequences encoding these enzymes may not be required to confer the host cell the ability to produce steviol or a steviol glycoside. A preferred host according to the present disclosure may be a recombinant host which is naturally capable of producing GGPP (i.e. in its non-recombinant form).

Further improvement of steviol or steviol glycoside production by the host microorganism may be obtained by classical strain improvement.

A host cell may be a prokaryotic, archaebacterial or eukaryotic host cell.

A prokaryotic host cell may be, but is not limited to, a bacterial host cell. A eukaryotic host cell may be, but is not limited to, a yeast, a fungus, an amoeba, an algae, an animal, an insect host cell.

A eukaryotic host cell may be a fungal host cell. "Fungi" include all species of the subdivision Eumycotina (Alexopoulos, C. J., 1962, In: Introductory Mycology, John Wiley & Sons, Inc., New York). The term fungus thus includes among others filamentous fungi and yeast.

"Filamentous fungi" are herein defined as eukaryotic microorganisms that include all filamentous forms of the subdivision Eumycotina and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligatory aerobic. Filamentous fungal strains include, but are not limited to, strains of *Acremonium, Aspergillus, Agaricus, Aureobasidium, Cryptococcus, Corynascus, Chrysosporium, Filibasidium, Fusarium, Humicola, Magnaporthe, Monascus, Mucor, Myceliophthora, Mortierella, Neocallimastix, Neurospora, Paecilomyces, Penicillium, Piromyces, Phanerochaete Podospora, Pycnoporus, Rhizopus, Schizophyllum, Sordaria, Talaromyces, Rasmsonia, Thermoascus, Thielavia, Tolypocladium, Trametes* and *Trichoderma*. Preferred filamentous fungal strains that may serve as host cells belong to the species *Aspergillus niger, Aspergillus oryzae, Aspergillus fumigatus, Penicillium chrysogenum, Penicillium citrinum, Acremonium chrysogenum, Trichoderma reesei, Rasamsonia emersonii* (formerly known as *Talaromyces emersonii*), *Aspergillus sojae, Chrysosporium lucknowense, Myceliophtora thermophyla*. Reference host cells for the comparison of fermentation characteristics of transformed and untransformed cells, include e.g. *Aspergillus niger* CBS120.49, CBS 513.88, *Aspergillus oryzae* ATCC16868, ATCC 20423, IFO 4177, ATCC 1011, ATCC 9576, ATCC14488-14491, ATCC 11601, ATCC12892, *Aspergillus fumigatus* AF293 (CBS101355), *P. chrysogenum* CBS 455.95, *Penicillium citrinum* ATCC 38065, *Penicillium chrysogenum* P2, *Acremonium chrysogenum* ATCC 36225, ATCC 48272, *Trichoderma reesei* ATCC 26921, ATCC 56765, ATCC 26921, *Aspergillus sojae* ATCC11906, *Chrysosporium lucknowense* ATCC44006 and derivatives of all of these strains. Particularly preferred as filamentous fungal host cell are *Aspergillus niger* CBS 513.88 and derivatives thereof.

A eukaryotic host cell may be a yeast cell. Preferred yeast host cells may be selected from the genera: *Saccharomyces* (e.g., *S. cerevisiae, S. bayanus, S. pastorianus, S. carlsbergensis*), *Brettanomyces, Kluyveromyces, Candida* (e.g., *C. krusei, C. revkaufi, C. pulcherrima, C. tropicalis, C. utilis*), *Issatchenkia* (e.g. *I. orientalis*) *Pichia* (e.g., *P. pastoris*),0 *Schizosaccharomyces, Hansenula, Kloeckera, Pachysolen, Schwanniomyces, Trichosporon, Yarrowia* (e.g., *Y. lipolytica* (formerly classified as *Candida lipolytica*)), *Yamadazyma*.

Prokaryotic host cells may be bacterial host cells. Bacterial host cell may be Gram negative or Gram positive bacteria. Examples of bacteria include, but are not limited to, bacteria belonging to the genus *Bacillus* (e.g., *B. subtilis, B. amyloliquefaciens, B. licheniformis, B. puntis, B. megaterium, B. halodurans, B. pumilus*), *Acinetobacter, Nocardia, Xanthobacter, Escherichia* (e.g., *E. coli* (e.g., strains DH 1 OB, Stbl2, DH5-alpha, DB3, DB3.1), DB4, DB5, JDP682 and ccdA-over (e.g., U.S. application Ser. No. 09/518, 188))), *Streptomyces, Erwinia, Klebsiella, Serratia* (e.g., *S. marcessans*), *Pseudomonas* (e.g., *P. aeruginosa*), *Salmonella* (e.g., *S. typhimurium, S. typhi*). Bacteria also include, but are not limited to, photosynthetic bacteria (e.g., green non-sulfur bacteria (e.g., Choroflexus bacteria (e.g., *C. aurantiacus*), *Chloronema* (e.g., *C. gigateum*)), green sulfur bacteria (e.g., *Chlorobium* bacteria (e.g., *C. limicola*), *Pelodictyon* (e.g., *P. luteolum*), purple sulfur bacteria (e.g., *Chromatium* (e.g., *C. okenii*)), and purple non-sulfur bacteria (e.g., *Rhodospirillum* (e.g., *R. rubrum*), *Rhodobacter* (e.g. *R. sphaeroides, R. capsulatus*), and *Rhodomicrobium* bacteria (e.g., *R. vanellii*)).

Host Cells may be host cells from non-microbial organisms. Examples of such cells, include, but are not limited to, insect cells (e.g., *Drosophila* (e.g., *D. melanogaster*), *Spodoptera* (e.g., *S. frugiperda* Sf9 or Sf21 cells) and Trichoplusa (e.g., High-Five cells); nematode cells (e.g., *C. elegans* cells); avian cells; amphibian cells (e.g., *Xenopus laevis* cells); reptilian cells; and mammalian cells (e.g., NIH3T3, 293, CHO, COS, VERO, C127, BHK, Per-C6, Bowes melanoma and HeLa cells).

The disclosure further provides a method for producing a polypeptide of the disclosure comprising:
  (a) cultivating a recombinant host cell of the disclosure under conditions conducive to the production of the polypeptide by the host cell, and optionally,
  (b) recovering the polypeptide.

A recombinant host according to the present disclosure may be able to grow on any suitable carbon source known in the art and convert it to a steviol glycoside, eg. a steviol glycoside. The recombinant host may be able to convert directly plant biomass, celluloses, hemicelluloses, pectines, rhamnose, galactose, fucose, maltose, maltodextrines, ribose, ribulose, or starch, starch derivatives, sucrose, glucose, lactose or glycerol. Hence, a preferred host expresses enzymes such as cellulases (endocellulases and exocellulases) and hemicellulases (e.g. endo- and exo-xylanases, arabinases) necessary for the conversion of cellulose into glucose monomers and hemicellulose into xylose and arabinose monomers, pectinases able to convert pectines into glucuronic acid and galacturonic acid or amylases to convert starch into glucose monomers. Preferably, the host is able to convert a carbon source selected from the group consisting of glucose, xylose, arabinose, sucrose, lactose and glycerol. The host cell may for instance be a eukaryotic host cell as described in WO03/062430, WO06/009434, EP1499708B1, WO2006096130 or WO04/099381.

Thus, in a further aspect, the disclosure also provides a process for the preparation of a steviol glycoside which comprises fermenting a recombinant host of the disclosure which is capable of producing at least one steviol glycoside in a suitable fermentation medium, and optionally recovering the steviol glycoside.

The steviol glycoside may be, for example, steviol-13-monoside, steviol-19-monoside, 13-[(β-D-Glucopyranosyl) oxy)kaur-16-en-18-oic acid 2-O-β-D-glucopyranosyl-β-D-glucopyranosyl ester, rubusoside, stevioside, steviol-19-diside, steviolbioside, rebA, rebaudioside B, rebaudioside C, rebaudioside E, rebaudioside D or rebaudioside M.

The fermentation medium used in the process for the production of a steviol glycoside may be any suitable fermentation medium which allows growth of a particular host cell. The essential elements of the fermentation medium are known to the person skilled in the art and may be adapted to the host cell selected.

Preferably, the fermentation medium comprises a carbon source selected from the group consisting of plant biomass, celluloses, hemicelluloses, pectines, rhamnose, galactose, fucose, fructose, maltose, maltodextrines, ribose, ribulose, or starch, starch derivatives, glucose, sucrose, lactose, fatty acids, triglycerides and glycerol. Preferably, the fermentation medium also comprises a nitrogen source such as urea, or an ammonium salt such as ammonium sulphate, ammonium chloride, ammonium nitrate or ammonium phosphate.

The fermentation process according to the present disclosure may be carried out in batch, fed-batch or continuous mode. A separate hydrolysis and fermentation (SHF) process or a simultaneous saccharification and fermentation (SSF) process may also be applied. A combination of these fermentation process modes may also be possible for optimal productivity. A SSF process may be particularly attractive if starch, cellulose, hemicelluose or pectin is used as a carbon source in the fermentation process, where it may be necessary to add hydrolytic enzymes, such as cellulases, hemicellulases or pectinases to hydrolyse the substrate.

The recombinant host used in the process for the preparation of a steviol glycoside may be any suitable recombinant host as defined herein above. It may be advantageous to use a recombinant eukaryotic host according to the disclosure in the process since most eukaryotic cells do not require sterile conditions for propagation and are insensitive to bacteriophage infections. In addition, eukaryotic host cells may be grown at low pH to prevent bacterial contamination.

The recombinant host according to the present disclosure may be a facultative anaerobic microorganism. A facultative anaerobic recombinant host can be propagated aerobically to a high cell concentration. This anaerobic phase can then be carried out at high cell density which reduces the fermentation volume required substantially, and may minimize the risk of contamination with aerobic microorganisms.

The fermentation process for the production of a steviol glycoside according to the present disclosure may be an aerobic or an anaerobic fermentation process.

An anaerobic fermentation process may be herein defined as a fermentation process run in the absence of oxygen or in which substantially no oxygen is consumed, preferably less than 5, 2.5 or 1 mmol/L/h, and wherein organic molecules serve as both electron donor and electron acceptors. The fermentation process according to the present disclosure may also first be run under aerobic conditions and subsequently under anaerobic conditions.

The fermentation process may also be run under oxygen-limited, or micro-aerobical, conditions. Alternatively, the fermentation process may first be run under aerobic conditions and subsequently under oxygen-limited conditions. An oxygen-limited fermentation process is a process in which the oxygen consumption is limited by the oxygen transfer from the gas to the liquid. The degree of oxygen limitation is determined by the amount and composition of the ingoing gasflow as well as the actual mixing/mass transfer properties of the fermentation equipment used.

The production of a steviol glycoside in the process according to the present disclosure may occur during the growth phase of the host cell, during the stationary (steady state) phase or during both phases. It may be possible to run the fermentation process at different temperatures.

The process for the production of a steviol glycoside may be run at a temperature which is optimal for the recombinant host. The optimum growth temperature may differ for each transformed recombinant host and is known to the person skilled in the art. The optimum temperature might be higher than optimal for wild type organisms to grow the organism efficiently under non-sterile conditions under minimal infection sensitivity and lowest cooling cost. Alternatively, the process may be carried out at a temperature which is not optimal for growth of the recombinant host.

The process for the production of a steviol glycoside according to the present disclosure may be carried out at any suitable pH value. If the recombinant host is a yeast, the pH in the fermentation medium preferably has a value of below 6, preferably below 5,5, preferably below 5, preferably below 4,5, preferably below 4, preferably below pH 3,5 or below pH 3,0, or below pH 2,5, preferably above pH 2. An advantage of carrying out the fermentation at these low pH values is that growth of contaminant bacteria in the fermentation medium may be prevented.

Such a process may be carried out on an industrial scale. The product of such a process is one or more steviol glycosides, such one or more of, for example, steviol-13-monoside, steviol-19-monoside, 13-[(β-D-Glucopyranosyl) oxy)kaur-16-en-18-oic acid 2-O-β-D-glucopyranosyl-β-D-glucopyranosyl ester, rubusoside, stevioside, steviol-19-diside, steviolbioside, rebaudiosideA, rebaudiosideE, rebaudiosideD or rebaudiosideM.

Recovery of steviol glycoside(s) from the fermentation medium may be performed by known methods in the art, for instance by distillation, vacuum extraction, solvent extraction, or evaporation.

In the process for the production of a steviol glycoside according to the disclosure, it may be possible to achieve a concentration of above 5 mg/I fermentation broth, preferably above 10 mg/I, preferably above 20 mg/I, preferably above 30 mg/I fermentation broth, preferably above 40 mg/I, more preferably above 50 mg/I, preferably above 60 mg/I, preferably above 70, preferably above 80 mg/I, preferably above 100 mg/I, preferably above 1 g/I, preferably above 5 g/I, preferably above 10 g/I, but usually below 70 g/I.

The disclosure further provides a fermentation broth comprising a steviol glycoside obtainable by the process of the disclosure for the preparation of a steviol glycoside.

A broth according to the disclosure may comprise a recombinant host cell of the disclosure. Alternatively, a broth of the disclosure may be one from which all host cells of the disclosure are absent or substantially absent, for example a supernatant.

In the event that one or more steviol glycosides is expressed within the microorganism, such cells may need to be treated so as to release them. Preferentially, at least one steviol glycoside, for example rebA, reb D or rebM, is produced extracellularly.

A broth according to the disclosure may comprise more than at least one steviol glycoside, such as rebA, rebD or rebM, as compared with a broth produced from a recombinant host in which a reference polypeptide is expressed instead of a polypeptide of the disclosure.

A broth according to the disclosure may comprise less of at least one non-steviol glycoside, for example one or more kaurenoic acid glycosides, as compared with a broth produced from a recombinant host in which a reference polypeptide is expressed instead of a polypeptide of the disclosure.

The disclosure also provides a steviol glycoside obtained by a process according to the disclosure for the preparation of a steviol glycoside or obtainable from a fermentation broth of the disclosure. Such a steviol glycoside may be a non-naturally occurring steviol glycoside, that is to say one which is not produced in plants.

Also provided is a composition comprising one or more, for example two or more, steviol glycosides obtainable by a process of the disclosure for the preparation of a steviol glycoside or obtainable from a fermentation broth of the disclosure. In such a composition, one or more of the steviol glycosides may be a non-naturally occurring steviol glycoside, that is to say one which is not produced in plants.

Furthermore, the disclosure provides a method for converting steviol or a first steviol glycoside into a second steviol glycoside, which method comprises:

contacting said steviol or first steviol glycoside with a recombinant host of the disclosure, a cell free extract derived from such a recombinant host or an enzyme preparation derived from either thereof;

thereby to convert the first steviol glycoside into the second steviol glycoside.

The first steviol glycoside may be any steviol glycoside, such as one illustrated in FIG. 1. The second steviol glycoside may be any steviol glycoside producing by action of a UGT enzyme on a first steviol glycoside (for example any steviol glycoside illustrated in FIG. 1).

In such a method, the second steviol glycoside may be, for example, rebA, rebE, rebD or RebM.

In such a method, the first steviol glycoside may be stevioside, rebB, rebA, rebE or rebD and the second steviol glycoside may be rebA, rebD or rebM.

Preferably, the first steviol glycoside is rebA and the second steviol glycoside is rebD or the first steviol glycoside is rebD and the second steviol glycoside is rebM.

That is to say, the disclosure relates to a method of bioconversion or biotransformation.

A steviol glycoside or composition produced by the fermentation process according to the present disclosure may be used in any application known for such compounds. In particular, they may for instance be used as a sweetener, for example in a food or a beverage. According to the disclosure therefore, there is provided a foodstuff, feed or beverage which comprises a steviol glycoside or a composition of the disclosure.

For example a steviol glycoside or a composition of the disclosure may be formulated in soft drinks, as a tabletop sweetener, chewing gum, dairy product such as yoghurt (eg. plain yoghurt), cake, cereal or cereal-based food, nutraceutical, pharmaceutical, edible gel, confectionery product, cosmetic, toothpastes or other oral cavity composition, etc. In addition, a steviol glycoside or a composition of the disclosure can be used as a sweetener not only for drinks, foodstuffs, and other products dedicated for human consumption, but also in animal feed and fodder with improved characteristics.

Accordingly, the disclosure provides, inter alia, a foodstuff, feed or beverage which comprises a steviol glycoside prepared according to a process of the disclosure.

During the manufacturing of foodstuffs, drinks, pharmaceuticals, cosmetics, table top products, chewing gum the conventional methods such as mixing, kneading, dissolution, pickling, permeation, percolation, sprinkling, atomizing, infusing and other methods can be used.

A steviol glycoside or a composition of the disclosure can be used in dry or liquid forms. It can be added before or after heat treatment of food products. The amount of the sweetener depends on the purpose of usage. It can be added alone or in the combination with other compounds.

Compounds produced according to the method of the disclosure may be blended with one or more further non-caloric or caloric sweeteners. Such blending may be used to improve flavour or temporal profile or stability. A wide range of both non-caloric and caloric sweeteners may be suitable for blending with a steviol glycoside or a composition of the disclosure. For example, non-caloric sweeteners such as mogroside, monatin, aspartame, acesulfame salts, cyclamate, sucralose, saccharin salts or erythritol. Caloric sweeteners suitable for blending with a steviol glycoside or a composition of the disclosure include sugar alcohols and carbohydrates such as sucrose, glucose, fructose and HFCS. Sweet tasting amino acids such as glycine, alanine or serine may also be used.

A steviol glycoside or a composition of the disclosure can be used in the combination with a sweetener suppressor, such as a natural sweetener suppressor. It may be combined with an umami taste enhancer, such as an amino acid or a salt thereof.

A steviol glycoside or a composition of the disclosure can be combined with a polyol or sugar alcohol, a carbohydrate, a physiologically active substance or functional ingredient (for example a carotenoid, dietary fiber, fatty acid, saponin, antioxidant, nutraceutical, flavonoid, isothiocyanate, phenol, plant sterol or stanol (phytosterols and phytostanols), a polyols, a prebiotic, a probiotic, a phytoestrogen, soy protein, sulfides/thiols, amino acids, a protein, a vitamin, a mineral, and/or a substance classified based on a health benefits, such as cardiovascular, cholesterol-reducing or anti-inflammatory.

A composition with a steviol glycoside or a composition of the disclosure may include a flavoring agent, an aroma component, a nucleotide, an organic acid, an organic acid salt, an inorganic acid, a bitter compound, a protein or protein hydrolyzate, a surfactant, a flavonoid, an astringent compound, a vitamin, a dietary fiber, an antioxidant, a fatty acid and/or a salt.

A steviol glycoside or a composition of the disclosure may be applied as a high intensity sweetener to produce zero calorie, reduced calorie or diabetic beverages and food products with improved taste characteristics. Also it can be used in drinks, foodstuffs, pharmaceuticals, and other products in which sugar cannot be used.

In addition, a steviol glycoside or a composition of the disclosure may be used as a sweetener not only for drinks, foodstuffs, and other products dedicated for human consumption, but also in animal feed and fodder with improved characteristics.

The examples of products where a steviol glycoside or a composition of the disclosure can be used as a sweetening compound can be as alcoholic beverages such as vodka, wine, beer, liquor, sake, etc.; natural juices, refreshing drinks, carbonated soft drinks, diet drinks, zero calorie drinks, reduced calorie drinks and foods, yogurt drinks, instant juices, instant coffee, powdered types of instant beverages, canned products, syrups, fermented soybean paste, soy sauce, vinegar, dressings, mayonnaise, ketchups, curry, soup, instant bouillon, powdered soy sauce, powdered vinegar, types of biscuits, rice biscuit, crackers, bread, chocolates, caramel, candy, chewing gum, jelly, pudding, preserved fruits and vegetables, fresh cream, jam, marmalade, flower paste, powdered milk, ice cream, sorbet, vegetables and fruits packed in bottles, canned and boiled beans, meat and foods boiled in sweetened sauce, agricultural vegetable food products, seafood, ham, sausage, fish ham, fish sausage, fish paste, deep fried fish products, dried seafood products, frozen food products, preserved seaweed, preserved meat, tobacco, medicinal products, and many others. In principal it can have unlimited applications.

The sweetened composition comprises a beverage, non-limiting examples of which include non-carbonated and carbonated beverages such as colas, ginger ales, root beers, ciders, fruit-flavored soft drinks (e.g., citrus-flavored soft drinks such as lemon-lime or orange), powdered soft drinks, and the like; fruit juices originating in fruits or vegetables, fruit juices including squeezed juices or the like, fruit juices containing fruit particles, fruit beverages, fruit juice beverages, beverages containing fruit juices, beverages with fruit flavorings, vegetable juices, juices containing vegetables, and mixed juices containing fruits and vegetables; sport drinks, energy drinks, near water and the like drinks (e.g., water with natural or synthetic flavorants); tea type or favorite type beverages such as coffee, cocoa, black tea, green tea, oolong tea and the like; beverages containing milk components such as milk beverages, coffee containing milk components, cafe au lait, milk tea, fruit milk beverages, drinkable yogurt, lactic acid bacteria beverages or the like; and dairy products.

Generally, the amount of sweetener present in a sweetened composition varies widely depending on the particular type of sweetened composition and its desired sweetness. Those of ordinary skill in the art can readily discern the appropriate amount of sweetener to put in the sweetened composition.

A steviol glycoside or a composition of the disclosure can be used in dry or liquid forms. It can be added before or after heat treatment of food products. The amount of the sweetener depends on the purpose of usage. It can be added alone or in the combination with other compounds.

During the manufacturing of foodstuffs, drinks, pharmaceuticals, cosmetics, table top products, chewing gum the conventional methods such as mixing, kneading, dissolution, pickling, permeation, percolation, sprinkling, atomizing, infusing and other methods can be used.

Thus, compositions of the present disclosure can be made by any method known to those skilled in the art that provide homogenous even or homogeneous mixtures of the ingredients. These methods include dry blending, spray drying, agglomeration, wet granulation, compaction, co-crystallization and the like.

In solid form a steviol glycoside or a composition of the disclosure can be provided to consumers in any form suitable for delivery into the comestible to be sweetened, including sachets, packets, bulk bags or boxes, cubes, tablets, mists, or dissolvable strips. The composition can be delivered as a unit dose or in bulk form.

For liquid sweetener systems and compositions convenient ranges of fluid, semi-fluid, paste and cream forms, appropriate packing using appropriate packing material in any shape or form shall be invented which is convenient to carry or dispense or store or transport any combination containing any of the above sweetener products or combination of product produced above.

The composition may include various bulking agents, functional ingredients, colorants, flavors.

The terms "sequence homology" or "sequence identity" are used interchangeably herein. For the purpose of this disclosure, it is defined here that in order to determine the percentage of sequence homology or sequence identity of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/based or amino acids. The sequence identity is the percentage of identical matches between the two sequences over the reported aligned region.

A comparison of sequences and determination of percentage of sequence identity between two sequences can be accomplished using a mathematical algorithm. The skilled person will be aware of the fact that several different computer programs are available to align two sequences and determine the identity between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent sequence identity between two amino acid sequences or between two nucleotide sequences may be determined using the Needleman and Wunsch algorithm for the alignment of two sequences. (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this disclosure the NEEDLE program from the EMBOSS package was used (version 2.8.0 or higher, EMBOSS: The European Molecular Biology Open Software Suite (2000)

Rice, P. Longden, I. and Bleasby, A. Trends in Genetics 16, (6) pp 276-277, emboss.bioinformatics.nl). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the disclosure is calculated as follows: Number of corresponding positions in the alignment showing an identical amino acid or identical nucleotide in both sequences divided by the total length of the alignment after subtraction of the total number of gaps in the alignment. The identity defined as herein can be obtained from NEEDLE by using the NOBRIEF option and is labelled in the output of the program as "longest-identity".

The nucleic acid and protein sequences of the present disclosure can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, word length=12 to obtain nucleotide sequences homologous to nucleic acid molecules of the disclosure. BLAST protein searches can be performed with the XBLAST program, score=50, word length=3 to obtain amino acid sequences homologous to protein molecules of the disclosure. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and NBLAST) can be used. See the homepage of the National Center for Biotechnology Information at ncbi.nlm.nih.gov.

Embodiments of the Disclosure:

1. A polypeptide having kaurenoic acid 13-hydroxylase activity, which polypeptide comprises an amino acid sequence which, when aligned with a kaurenoic acid 13-hydroxylase comprising the sequence set out in SEQ ID NO: 1 or SEQ ID NO: 3, comprises at least one substitution of an amino acid corresponding to any of amino acids at positions 136, 248, 336 or 403 said positions being defined with reference to SEQ ID NO: 1 or SEQ ID NO: 3 and wherein the polypeptide has one or more modified properties as compared with a reference polypeptide having kaurenoic acid 13-hydroxylase activity.

2. A polypeptide according to embodiment 1, wherein the positions in the polypeptide having kaurenoic acid 13-hydroxylase activity corresponding to any amino acids at position 136, 248, 336 or 403, said position being defined with reference to SEQ ID NO: 1 or SEQ ID NO: 3, are identified by aligning the amino acid sequence of the polypeptide with kaurenoic acid 13-hydroxylase activity with the amino acid sequence set out in SEQ ID NO: 1 or SEQ ID NO: 3 using the EMBOSS Needle alignment method, using EBLOSUM62 as a substitution matrix, with a gap-open penalty of 10 and a gap extension penalty of 0.5.

3. A polypeptide according to embodiment 1, wherein the modified property is modified kaurenoic acid 13-hydroxylase activity.

4. A polypeptide according to embodiment 1 or 2, wherein the reference polypeptide comprises the kaurenoic acid 13-hydroxylase of SEQ ID NO: 1 or SEQ ID NO: 3.

5. A polypeptide according to any one of the preceding embodiments wherein
  i. a methionine (M), valine (V), alanine (A), phenylalanine (F), tryptophan glutamine (Q), histidine (H) or a threonine (T) is present at a position corresponding to 136; and/or
  ii. an asparagine (N), glutamine (Q), threonine (T), glycine (G), alanine (A), isoleucine (I), valine (V), phenylalanine (F) or proline (P) is present at a position corresponding 248; and/or
  iii. a serine (S) an alanine (A) or isoleucine (I) is present at a position corresponding to 336; and/or
  iv. a glycine (G), leucine (L), valine (V), alanine (A), methionine (M) or serine (S) is present at a position corresponding to 403,
    said positions being defined with reference to SEQ ID NO: 1 or SEQ ID NO: 3.

6. A polypeptide according to any one of the preceding embodiments, wherein:
  (i) a methionine or valine is present at position 136;
  (ii) an asparagine is present at position 248;
  (iii) a serine is present at position 336; and/or
  (iv) a glycine is present at position 403,
  said positions being defined with reference to SEQ ID NO: 1 or SEQ ID NO: 3.

7. A polypeptide according to any one of the preceding embodiments, wherein the polypeptide comprises an amino acid sequence which, when aligned with the KAH comprising the sequence set out in SEQ ID NO: 1 or SEQ ID NO: 3, comprises at least the following substitutions of an amino acid corresponding to any of amino acids:
  136 and 248
  136 and 336
  136 and 403
  248 and 336
  248 and 403
  336 and 403
  136, 248 and 403
  136, 336 and 403
  136, 248 and 336
  248, 336 and 403 or
  136, 248, 336 and 403,
said positions being defined with reference to SEQ ID NO: 1 or SEQ ID NO: 3.

8. A polypeptide according to any one of the preceding embodiments which comprise an amino acid sequence which, when aligned with the KAH comprising the sequence set out in SEQ ID NO: 1 or SEQ ID NO: 3, comprises at least the following substitutions of an amino acid corresponding to any of amino acids:
  a) a methionine (M), or valine (V), or alanine (A), or phenylalanine (F), or tryptophan (W), or glutamine (Q), or histidine (H) or a threonine (T) present at a position corresponding to position 136 and an asparagine (N), or glutamine (Q), or threonine (T), or glycine (G), or alanine (A), or isoleucine (I), or valine (V), or phenylalanine (F) or proline (P) present at a position corresponding position 248;
  b) a methionine (M), or valine (V), or alanine (A), phenylalanine (F), or tryptophan (W), or glutamine (Q), or histidine (H) or a threonine (T) is present at a position corresponding to 136 and a serine (S), or an alanine (A), or isoleucine (I) is present at a position corresponding to position 336;

c) a methionine (M), or valine (V), or alanine (A), phenylalanine (F), or tryptophan (W), or glutamine (Q), or histidine (H) or a threonine (T) is present at a position corresponding to 136 and a glycine (G), or leucine (L), or valine (V), or alanine (A), or methionine (M) or serine (S) is present at a position corresponding to position 403;

d) an asparagine (N), or glutamine (Q), or threonine (T), or glycine (G), or alanine (A), or isoleucine (I), or valine (V), or phenylalanine (F) or proline (P) present at a position corresponding position 248 and a serine (S), or an alanine (A), or isoleucine (I) is present at a position corresponding to position 336;

e) an asparagine (N), or glutamine (Q), or threonine (T), or glycine (G), or alanine (A), or isoleucine (I), or valine (V), or phenylalanine (F) or proline (P) present at a position corresponding position 248 and a glycine (G), or leucine (L), or valine (V), or alanine (A), or methionine (M) or serine (S) is present at a position corresponding to position 403;

f) a serine (S), or an alanine (A), or isoleucine (I) is present at a position corresponding to position 336 and a glycine (G), or leucine (L), or valine (V), or alanine (A), or methionine (M) or serine (S) is present at a position corresponding to position 403;

g) a methionine (M), or valine (V), or alanine (A), phenylalanine (F), or tryptophan (W), or glutamine (Q), or histidine (H) or a threonine (T) is present at a position corresponding to 136, an asparagine (N), or glutamine (Q), or threonine (T), or glycine (G), or alanine (A), or isoleucine (I), or valine (V), or phenylalanine (F) or proline (P) present at a position corresponding position 248 and a glycine (G), or leucine (L), or valine (V), or alanine (A), or methionine (M) or serine (S) is present at a position corresponding to position 403;

h) a methionine (M), or valine (V), or alanine (A), phenylalanine (F), or tryptophan (W), or glutamine (Q), or histidine (H) or a threonine (T) is present at a position corresponding to 136, a serine (S), or an alanine (A), or isoleucine (I) is present at a position corresponding to position 336 and a glycine (G), or leucine (L), or valine (V), or alanine (A), or methionine (M) or serine (S) is present at a position corresponding to position 403;

i) a methionine (M), or valine (V), or alanine (A), phenylalanine (F), or tryptophan (W), or glutamine (Q), or histidine (H) or a threonine (T) is present at a position corresponding to 136, an asparagine (N), or glutamine (Q), or threonine (T), or glycine (G), or alanine (A), or isoleucine (I), or valine (V), or phenylalanine (F) or proline (P) present at a position corresponding position 248 and a serine (S), or an alanine (A), or isoleucine (I) is present at a position corresponding to position 336;

j) an asparagine (N), or glutamine (Q), or threonine (T), or glycine (G), or alanine (A), or isoleucine (I), or valine (V), or phenylalanine (F) or proline (P) present at a position corresponding position 248, a serine (S), or an alanine (A), or isoleucine (I) is present at a position corresponding to position 336 and a glycine (G), or leucine (L), or valine (V), or alanine (A), or methionine (M) or serine (S) is present at a position corresponding to position 403 or k) a methionine (M), or valine (V), or alanine (A), phenylalanine (F), or tryptophan (W), or glutamine (Q), or histidine (H) or a threonine (T) is present at a position corresponding to 136, an asparagine (N), or glutamine (Q), or threonine (T), or glycine (G), or alanine (A), or isoleucine (I), or valine (V), or phenylalanine (F) or proline (P) present at a position corresponding position 248, a serine (S), or an alanine (A), or isoleucine (I) is present at a position corresponding to position 336 and a glycine (G), or leucine (L), or valine (V), or alanine (A), or methionine (M) or serine (S) is present at a position corresponding to position 403, said positions being defined with reference to SEQ ID NO: 1 or SEQ ID NO: 3.

9. A polypeptide according to any one of the preceding embodiments, wherein the polypeptide is a non-naturally occurring polypeptide.

10. A polypeptide according to any one of the preceding embodiments which comprises additional substitutions other than those defined in any one of the previous embodiments.

11. A polypeptide according to any one of the preceding embodiments comprising an amino acid sequence having at least 70%, at least 75%, at least 80%, at least 85%, at least 90%, at least 95%, at least 97%, at least 98% or at least 99% sequence identity with SEQ ID NO: 1 or SEQ ID NO: 3.

12. A polypeptide having kaurenoic acid 13-hydroxylase activity comprising an amino acid sequence having at least about 95% sequence identity, at least 96%, at least 97%, at least 98% or at least 99% sequence identity to any one of SEQ ID NO: 5, 7, 9, 11 or 13.

13. A nucleic acid comprising a sequence encoding a polypeptide according to any one of the preceding embodiments.

14. A nucleic acid construct comprising the nucleic acid sequence of embodiment 13, operably linked to one or more control sequences capable of directing the expression of a kaurenoic acid 13-hydroxylase in a suitable expression host.

15. An expression vector comprising a nucleic acid according to embodiment 14 or a nucleic acid construct according to embodiment 13.

16. A recombinant host comprising a nucleic acid according to embodiment 13, a nucleic acid construct according to embodiment 14 or an expression vector according to embodiment 15.

17. A recombinant host according to embodiment 16 which is capable of producing steviol or a steviol glycoside.

18. A recombinant host according to embodiment 16 or 17 which comprises one or more recombinant nucleotide sequence(s) encoding:
 a polypeptide having ent-copalyl pyrophosphate synthase activity;
 a polypeptide having ent-Kaurene synthase activity; and
 a polypeptide having ent-Kaurene oxidase activity; and, optionally,
 a polypeptide having kaurenoic acid 13-hydroxylase activity which is different from a polypeptide according to any one of embodiments 1 to 12.

19. A recombinant host according to any one of embodiments 16 to 18, which comprises a recombinant nucleic acid sequence encoding a polypeptide having NADPH-cytochrome p450 reductase activity.

20. A recombinant host according to any one of embodiments 16 to 19 which comprises a recombinant nucleic acid sequence encoding one or more of:
 (i) a polypeptide having UGT74G1 activity;
 (ii) a polypeptide having UGT2 activity;
 (iii) a polypeptide having UGT85C2 activity; and
 (iv) a polypeptide having UGT76G1 activity.

21. A recombinant host according to any one of embodiments 16 to 20, wherein the host belongs to one of the genera Saccharomyces, Aspergillus, Pichia, Kluyveromyces, Candida, Hansenula, Humicola, Issatchenkia, Trichosporon, Brettanomyces, Pachysolen, Yarrowia, Yamadazyma or Escherichia.

22. A recombinant host according to embodiment 21, wherein the recombinant host is a Saccharomyces cerevisiae cell, a Yarrowia lipolytica cell, a Candida krusei cell, an Issatchenkia orientalis cell or an Escherichia coli cell.

23. A recombinant host according to any one of embodiments 16 to 22, wherein the ability of the host to produce geranylgeranyl diphosphate (GGPP) is upregulated.

24. A recombinant host according to any one of embodiments 16 to 23 which comprises a nucleic acid sequence encoding one or more of:
a polypeptide having hydroxymethylglutaryl-CoA reductase activity;
a polypeptide having farnesyl-pyrophosphate synthetase activity;
a polypeptide having geranylgeranyl diphosphate synthase activity.

25. A method of producing a KAH polypeptide according to any one of embodiments 1 to 12, which method comprises:
a) selecting a reference KAH polypeptide (such as a reference polypeptide having at least 80% sequence identity to a polypeptide with an amino acid sequence according to SEQ ID NO: 1 or SEQ ID NO:3;
b) substituting at least one amino acid residue corresponding to any of
136, 248, 336 or 403
said positions being defined with reference to SEQ ID NO: 1 or SEQ ID NO: 3;
c) optionally substituting one or more further amino acids as defined in b);
d) preparing the KAH resulting from steps a)-c);
e) determining a property of the KAH, for example as set out in the Examples; and
f) selecting a KAH with an altered property in comparison to the reference KAH polypeptide.

26. A process for the preparation of steviol or a steviol glycoside which comprises fermenting a recombinant host according to any one of embodiments 16 to 24 in a suitable fermentation medium and, optionally, recovering the steviol or steviol glycoside.

27. A process according to embodiment 26 for the preparation of a steviol glyocisde, wherein the process is carried out on an industrial scale.

28. A fermentation broth comprising a steviol glycoside obtainable by the process according to embodiment 26 or 27.

29. A steviol glycoside obtained by a process according to embodiment 26 or 27 or obtained from a fermentation broth according to embodiment 28.

30. A composition comprising one or more steviol glycosides according to embodiment 29.

31. A foodstuff, feed or beverage which comprises a steviol glycoside according to embodiment 29 or a composition according to embodiment 30.

32. A method for converting steviol or a first steviol glycoside into a second steviol glycoside, which method comprises:
contacting said steviol or first steviol glycoside with a recombinant host according to any one of embodiments 16 to 24, a cell free extract derived from such a recombinant host or an enzyme preparation derived from either thereof;
thereby to convert the steviol or first steviol glycoside into the second steviol glycoside.

33. A method according to embodiment 32, wherein the second steviol glycoside is: rebA, rebE, rebD or RebM.

34. A method according to embodiment 33, wherein the first steviol glycoside is stevioside, rebB, rebA, rebE or rebD and the second steviol glycoside is rebA, rebD or rebM.

35. A method for producing a kaurenoic acid 13-hydroxylase according to any one of embodiments 1 to 12 comprising cultivating a recombinant host cell according to any one of embodiments 16 to 24 under conditions suitable for production of the kaurenoic acid 13-hydroxylase by the host cell and, optionally, recovering the kaurenoic acid 13-hydroxylase.

A reference herein to a patent document or other matter which is given as prior art is not to be taken as an admission that that document or matter was known or that the information it contains was part of the common general knowledge as at the priority date of any of the claims.

The disclosure of each reference set forth herein is incorporated herein by reference in its entirety.

The present disclosure is further illustrated by the following Examples:

EXAMPLES

General

Standard genetic techniques, such as overexpression of enzymes in the host cells, as well as for additional genetic modification of host cells, are known methods in the art, such as described in Sambrook and Russel (2001) "Molecular Cloning: A Laboratory Manual ($3^{rd}$ edition), Cold Spring Harbor Laboratory, Cold Spring Harbor Laboratory Press, or F. Ausubel et al, eds., "Current protocols in molecular biology", Green Publishing and Wiley Interscience, New York (1987). Methods for transformation and genetic modification of fungal host cells are known from e.g. EP-A-0 635 574, WO 98/46772, WO 99/60102 and WO 00/37671.

Example 1. KAH Expression in Yarrowia lipolytica

Figure 2:
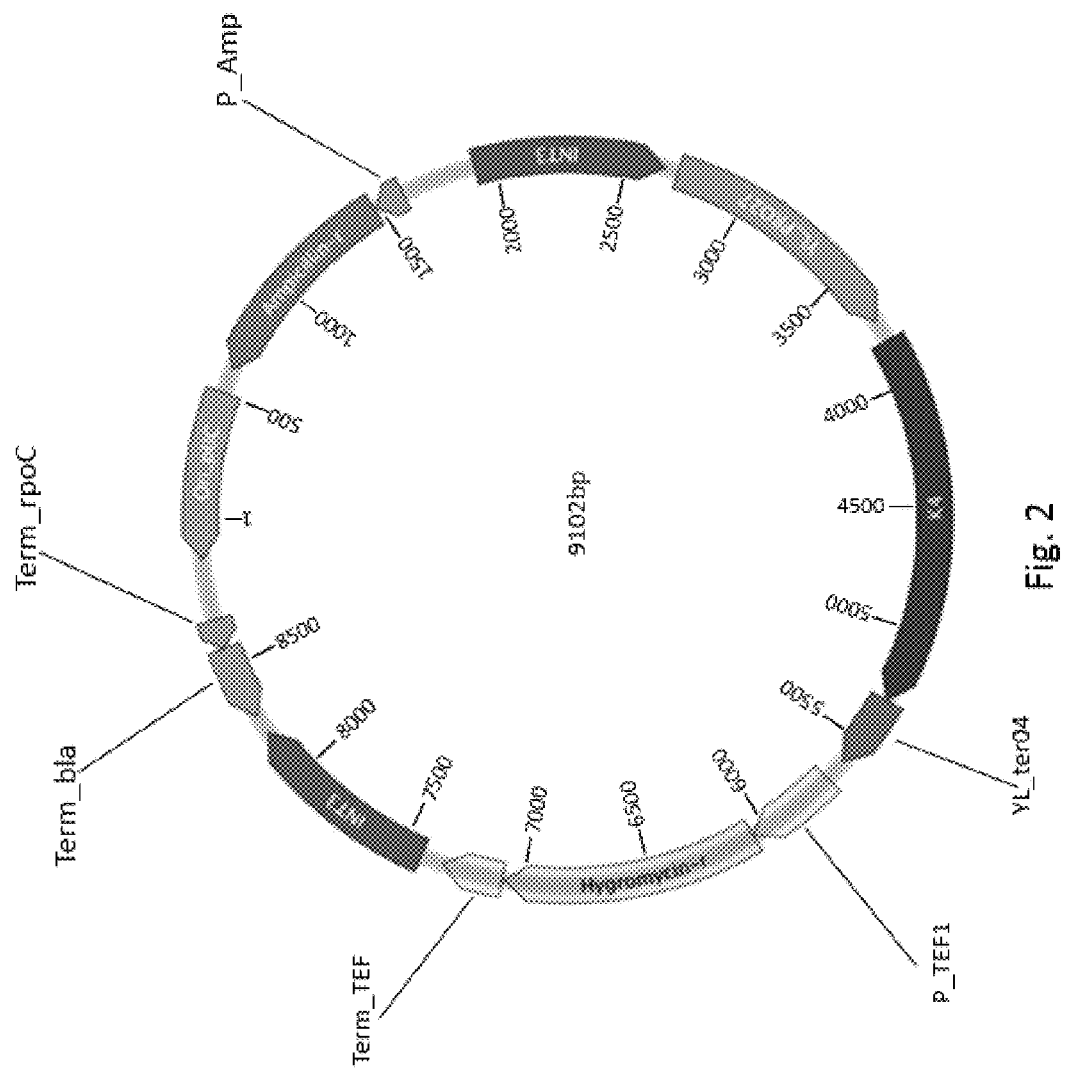
FIG. 2 sets out the plasmid map for genes encoding polypeptides having KAH activity cloned into a vector containing the INT3 integration flanks (which allow homologous recombination in *Y. lipolytica*), and promotor-orf-terminator for KAH4 and HygB (encoding for resistance against hygromycin).

Different kaurenoic acid hydroxylase (KAH)-encoding genes (see Table 1 below) were ordered as cloned genes in a vector at DNA2.0, and contained the INT3 integration flanks (which allow homologous recombination in Y. lipolytica), and promotor-orf-terminator for KAH and HygB (encoding for resistance against hygromycin). See FIG. 2 for the plasmid map.

TABLE 1

KAH genes

| Name | Amino acid sequence | Nucleic acid sequence | Substitutions in comparison with SEQ ID NO: 1 |
|---|---|---|---|
| KAH4_m4 | SEQ ID NO: 3 | SEQ ID NO: 4 | |
| KAH4_p18 | SEQ ID NO: 5 | SEQ ID NO: 6 | I136M |
| KAH4_p19 | SEQ ID NO: 7 | SEQ ID NO: 8 | F336S |
| KAH4_p20 | SEQ ID NO: 9 | SEQ ID NO: 10 | I136V |
| KAH4_p21 | SEQ ID NO: 11 | SEQ ID NO: 12 | S248N |
| KAH4_p22 | SEQ ID NO: 13 | SEQ ID NO: 14 | I403G |

The expression pathways containing integration flanks, KAH and HygB expression cassettes were PCR-amplified from the plasmids. The purified PCR products were transformed to Y. lipolytica strain STV2226, and hygromycin resistant colonies were selected. The STV2226 strain already expresses all the genes that are required for steviol glycosides production to produce steviol glycosides, except for KAH. The gene content of this strain is given below in Table 2. Construction of similar strains has been described in more detail in patent application numbers WO2013/110673 and WO2015/007748. The STV2226 strain contains an internal deletion of 1658 bp in the ku70 gene, to increase the efficiency of targeted integration.

TABLE 2

Genotype of strain STV2226. Between brackets indicates the gene copy number present in the strain

| Strain name | Genotype |
|---|---|
| STV2226 | MATB ku70Δ tHMG (2; SEQ ID NO: 15) GGS (2; SEQ ID NO: 16) CarG (1; SEQ ID NO: 17) CPS (5; SEQ ID NO: 18) KS (4; SEQ ID NO: 19) KO (2; SEQ ID NO: 20) CPR3 (2; SEQ ID NO: 21) UGT1 (3; SEQ ID NO: 22) UGT2 (2; SEQ ID NO: 23) UGT3 (2; SEQ ID NO: 24) UGT4 (3; SEQ ID NO: 25) |

Example 2. Production of Glycosylated Kaurenoic Acid and Steviol Glucosides in Strains Expressing KAH Genes STV2226 transformed with the different KAH genes were plated on YPhD plates containing hygromycin, single colony isolates were obtained, and a production test was performed: as pre-culture 200 μl YEP with glucose was inoculated with colony material from YEPh-D agar plates containing hygromycin. The pre-culture was incubated 72 hours in an Infors incubator at 30° C., 750 rpm and 80% humidity. 40 μl of pre-culture was used to inoculate 2.5 ml mineral medium with glucose as carbon source. These production cultures were incubated 120 hours in an Infors incubator at 30° C., 550 rpm, 80% humidity. The production cultures were pelleted by centrifugation at 3000 g for 10 minutes. After centrifugation supernatant was transferred and diluted in 33% acetonitrile and analyzed for steviol, steviol glycosides, kaurenoic acid (KA) and glycosylated kaurenoic acid (KA-glycosides) using LC/MS. To represent the data, steviol glycosides titers (mM) and KA-glycoside titers (mM) were normalized to the titers obtained with STV2226 transformed with KAH4_m4 (SEQ ID NO: 2). For an overview of the results, see Table 3.

TABLE 3

Production of KA-glycosides and steviol-glycosides. Values represent averages of around nine replicates for most genes, and at least of two replicates for all genes. Steviol glycosides (mM) and KA-glycosides (mM) were normalized to the production in strain STV2226 transformed with KAH4_m4.

| Strain | Sum steviol glycosides | Sum KA-glycosides | Steviol glycosides/KA-glycosides |
|---|---|---|---|
| STV2226 + KAH4_m4 | 100 | 100 | 4.3 |
| STV2226 + KAH4_p18 | 100 | 47 | 9.2 |
| STV2226 + KAH4_p19 | 154 | 101 | 6.6 |
| STV2226 + KAH4_p20 | 115 | 56 | 8.9 |
| STV2226 + KAH4_p21 | 130 | 64 | 8.9 |
| STV2226 + KAH4_p22 | 106 | 75 | 6.3 |

The sum of steviol glycosides includes steviol-13-monoside, steviol-19-monoside, steviol bioside, rubusoside, Rebaudioside B, stevioside, Rebaudioside A, Rebaudioside E, Rebaudioside D and Rebaudioside M. Sum KA-glycosides includes KA, KA-19-monoglucoside, KA-19-diglucoside and KA-19-triglucoside.

The strains that expressed the KAH genes KAH4_p19, KAH4_p20, KAH4_p21 and KAH4_p22, produced higher titers of steviol glycosides. Expression of some of these genes resulted in 30% or more improvement in total steviol glycosides production compared to KAH4_m4. The formation of the undesired KA-glycosides was greatly reduced for genes KAH4_p18, KAH4_p20, KAH4_p21 and KAH4_p22. The ratio of desired product (steviol glycosides) over undesired byproducts (KA-glycosides) increased for all strains expressing genes KAH4_p18 to KAH4_p22 compared to the strain expressing KAH4_m4, for some KAH genes even by a factor of more than 2. These results illustrate that KAH4_p18 to KAH4_p22 enzymes are beneficial for the production of steviol glycosides.

Example 3. Production of Glycosylated Kaurenoic Acid and Steviol Glycosides in Bioreactors Three of the strains, expressing KAH4_m4 (reference), KAH4_p20 and KAH4_p21 constructed as described above were cultivated in 500 mL shake-flasks with 50 ml mineral medium for 3 days at 30° C. and 280 rpm. Subsequently, 6 ml of the content of the shake-flask was transferred into a fermenter with a starting volume of 0.3 L. The pH was controlled at 5.0 by addition of ammonia (12.5 wt %). Temperature was controlled at 30° C. Glucose concentration was kept limited by controlled glucose feed to the fermenter. The mineral medium of the shake flask and fermentation was based on Verduyn et al. (Verduyn C, Postma E, Scheffers W A, Van Dijken J P. Yeast, 1992 July; 8(7):501-517). Broth samples were diluted in water and 33% acetonitrile and analyzed with LC/MS.

TABLE 4

Steviol glycoside and KA-glycoside production in bioreactors. Steviol glycosides (mM) and KA-glycosides (mM) were normalized to the production in strain STV2226 transformed with KAH4_m4.

| Strain | Sum steviol glycosides (%) | Sum KA-glycosides (%) | Sum steviol glycosides/sum KA-glycosides |
|---|---|---|---|
| STV2226 + KAH4_m4 | 100 | 100 | 11 |
| STV2226 + KAH4_p20 | 120 | 63 | 20 |
| STV2226 + KAH4_p21 | 101 | 37 | 29 |

The sum of steviol glycosides includes steviol, steviol-13-monoside, steviol-19-monoside, steviol bioside, rubusoside, Rebaudioside B, stevioside, Rebaudioside A, Rebaudioside E, Rebaudioside D and Rebaudioside M. Sum KA-glycosides includes KA, KA-19-monoglucoside, KA-19-diglucoside and KA-19-triglucoside.

We observed that the amount of steviol glycosides increases when the KAH4_p20 is expressed, resulting in 20% higher production of total steviol glycosides. In addition the amount of KA-glycosides decreases, with more than 35%. When KAH4_p21 is expressed the reduction in KA-glycosides is even higher, with more than 60% reduction. As a result, with KAH4_p20 or with KAH4_p21 expression, the ratio of steviol glycosides over KA-glycosides is increased dramatically compared to the strain expressing KAH4_m4. Use of KAH4_p20 or KAH4_p21 will have a positive effect on the production and purification of steviol glycosides.

The invention claimed is:

1. A method for converting steviol or a first steviol glycoside into a second steviol glycoside, which method comprises:

contacting steviol or first steviol glycoside with a recombinant host, a cell free extract derived from the recombinant host, or an enzyme preparation derived from either thereof;

thereby to convert the steviol or first steviol glycoside into the second steviol glycoside;

wherein the recombinant host comprises a nucleic acid comprising a sequence encoding a polypeptide having kaurenoic acid 13-hydroxylase activity, which polypeptide comprises an amino acid sequence having at least 90% sequence identity with SEQ ID NO:1 and which, when aligned with SEQ ID NO:1, comprises at least one substitution of an amino acid corresponding to any of amino acids at positions 136, 248, 336 or 403, said positions being defined with reference to SEQ ID NO:1, and wherein the polypeptide has one or more modified properties as compared with a reference polypeptide having kaurenoic acid 13-hydroxylase activity.

2. The method according to claim 1, wherein the modified property is modified kaurenoic acid 13-hydroxylase activity.

3. The method according to claim 1, wherein the reference polypeptide comprises the kaurenoic acid 13-hydroxylase of SEQ ID NO:1.

4. The method according to claim 1, wherein:
(i) a methionine or valine is present at position 136;
(ii) an asparagine is present at position 248;
(iii) a serine is present at position 336; and/or
(iv) a glycine is present at position 403,
said positions being defined with reference to SEQ ID NO:1.

5. The method of claim 1, wherein the recombinant host further comprises one or more recombinant nucleotide sequence(s) encoding:
a polypeptide having ent-copalyl pyrophosphate synthase activity;
a polypeptide having ent-Kaurene synthase activity; and
a polypeptide having ent-Kaurene oxidase activity; and, optionally,
a polypeptide having kaurenoic acid 13-hydroxylase activity which is different from said polypeptide having kaurenoic acid 13-hydroxylase activity.

6. The method of claim 1, wherein the recombinant host further comprises a recombinant nucleic acid sequence encoding a polypeptide having NADPH-cytochrome p450 reductase activity.

7. The method of claim 1, wherein the recombinant host further comprises a recombinant nucleic acid sequence encoding one or more of:
(i) a polypeptide having UGT74G1 activity;
(ii) a polypeptide having UGT2 activity;
(iii) a polypeptide having UGT85C2 activity; and
(iv) a polypeptide having UGT76G1 activity.

8. The method according to claim 1, wherein the recombinant host belongs to one of the genera *Saccharomyces, Aspergillus, Pichia, Kluyveromyces, Candida, Hansenula, Humicola, Issatchenkia, Trichosporon, Brettanomyces, Pachysolen, Yarrowia, Yamadazyma* or *Escherichia*, optionally a *Saccharomyces cerevisiae* cell, a *Yarrowia lipolytica* cell, a *Candida krusei* cell, an *Issatchenkia orientalis* cell or an *Escherichia coli* cell.

* * * * *